(12) United States Patent
Flaherty et al.

(10) Patent No.: US 6,960,192 B1
(45) Date of Patent: Nov. 1, 2005

(54) TRANSCUTANEOUS FLUID DELIVERY SYSTEM

(75) Inventors: J. Christopher Flaherty, Topsfield, MA (US); William Gorman, South Hamilton, MA (US); John Garibotto, Charlestown, MA (US); Timothy Wood, Wilmington, MA (US); Patick Gutelius, Monroe, CT (US)

(73) Assignee: Insulet Corporation, Bedford, MA (US)

( * ) Notice: Subject to any disclaimer, the term of this patent is extended or adjusted under 35 U.S.C. 154(b) by 450 days.

(21) Appl. No.: 10/128,206

(22) Filed: Apr. 23, 2002

(51) Int. Cl.[7] .......................... A61M 5/00; A61M 37/00; A61M 5/178

(52) U.S. Cl. ....................... 604/181; 604/131; 604/134; 604/185

(58) Field of Search ........................ 604/181, 183–185, 604/131, 132, 187, 133, 134, 136

(56) References Cited

U.S. PATENT DOCUMENTS

| | | | |
|---|---|---|---|
| 3,631,847 A | 1/1972 | Hobbs | |
| 3,812,843 A | 5/1974 | Wootten et al. | |

(Continued)

FOREIGN PATENT DOCUMENTS

| | | |
|---|---|---|
| DE | 4200595 | 7/1993 |
| DE | 19920896 | 9/2000 |
| EP | 0342947 | 5/1989 |
| EP | 0763369 | 3/1997 |
| EP | 0867196 | 3/1998 |
| EP | 0937475 | 8/1999 |
| WO | WO81/01658 | 6/1981 |
| WO | WO86/06796 | 11/1986 |
| WO | WO98/00193 | 1/1998 |
| WO | WO98/01071 | 1/1998 |
| WO | WO99/10040 | 3/1999 |
| WO | WO00/19887 | 9/1999 |
| WO | WO99/62576 | 9/1999 |
| WO | WO99/56803 | 11/1999 |
| WO | WO0010628 | 3/2000 |
| WO | WO00/29047 | 5/2000 |
| WO | WO00/29049 | 5/2000 |
| WO | WO00/74752 | 5/2000 |
| WO | WO00/30705 | 6/2000 |
| WO | WO00/78210 | 6/2000 |
| WO | WO00/48112 | 8/2000 |
| WO | WO00/61215 | 10/2000 |
| WO | WO01/52727 | 1/2001 |
| WO | WO01/5663 | 8/2001 |
| WO | WO01/76684 | 10/2001 |
| WO | WO02/20073 | 3/2002 |
| WO | WO02/26282 | 4/2002 |

OTHER PUBLICATIONS

US 5,954,699, 9/1999, Jost et al. (withdrawn)
International Search Report (PCT/US03/12370).

(Continued)

*Primary Examiner*—Sharon Kennedy

(57) ABSTRACT

A device for delivering fluid to a person includes a reservoir for containing a fluid to be delivered to the person; a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device; a housing containing the reservoir and the fluid transport device, the housing including an exit port for receiving the distal end of the fluid transport device upon injection of the distal end into the person and means for securing a first wall of the housing to the skin of the person; and an injection activation device including a driving mechanism contacting the fluid transport device for driving the penetrating member from a first position within the housing, through the exit port to a second position, external to the housing and into the skin of the person.

172 Claims, 32 Drawing Sheets

U.S. PATENT DOCUMENTS

| | | |
|---|---|---|
| 4,067,000 A | 1/1978 | Carlson |
| 4,108,177 A | 8/1978 | Pistor |
| 4,151,845 A | 5/1979 | Clemens |
| 4,193,397 A | 3/1980 | Tucker et al. |
| 4,211,998 A | 7/1980 | Junginger et al. |
| 4,231,019 A | 10/1980 | Junginger et al. |
| 4,268,150 A | 5/1981 | Chen |
| 4,364,385 A | 12/1982 | Lossef |
| 4,373,527 A | 2/1983 | Fischell |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,514,732 A | 4/1985 | Hayes, Jr. |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,560,979 A | 12/1985 | Rosskopk |
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| D303,013 S | 8/1989 | Konopka |
| 4,855,746 A | 8/1989 | Stacy |
| 4,871,351 A | 10/1989 | Feingold |
| 4,882,600 A | 11/1989 | Van de Moere |
| 4,886,499 A | 12/1989 | Cirelli et al. |
| 4,898,579 A | 2/1990 | Groshong et al. |
| D306,691 S | 3/1990 | Arai |
| 4,944,659 A | 7/1990 | Labbe et al. |
| D311,735 S | 10/1990 | Arai et al. |
| 4,969,874 A | 11/1990 | Michel et al. |
| 4,973,998 A | 11/1990 | Gates |
| D315,727 S | 3/1991 | Arai et al. |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,176,662 A | 1/1993 | Bartholomew et al. |
| 5,178,609 A | 1/1993 | Ishikawa |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,242,406 A | 9/1993 | Gross et al. |
| 5,244,463 A | 9/1993 | Cordner, Jr. et al. |
| 5,254,096 A | 10/1993 | Rondelet et al. |
| 5,257,980 A | 11/1993 | Van Antwerp et al. |
| 5,281,202 A | 1/1994 | Weber et al. |
| 5,308,335 A | 5/1994 | Ross et al. |
| 5,312,337 A | 5/1994 | Flaherty et al. |
| 5,318,540 A | 6/1994 | Athayde et al. |
| 5,342,313 A | 8/1994 | Campbell et al. |
| 5,346,476 A | 9/1994 | Elson |
| 5,364,342 A | 11/1994 | Beuchat et al. |
| 5,411,480 A | 5/1995 | Kriesel |
| 5,433,710 A | 7/1995 | Van Antwerp et al. |
| 5,452,033 A | 9/1995 | Balling et al. |
| 5,492,534 A | 2/1996 | Athayde et al. |
| 5,505,709 A | 4/1996 | Funderburk et al. |
| 5,507,288 A | 4/1996 | Bocker et al. ............... 128/633 |
| 5,514,096 A | 5/1996 | Hiejima |
| 5,533,389 A | 7/1996 | Kamen |
| 5,545,152 A | 8/1996 | Funderburk et al. |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,660,728 A | 8/1997 | Saaski et al. |
| 5,665,065 A | 9/1997 | Colman et al. |
| 5,665,070 A | 9/1997 | McPhee |
| 5,695,490 A | 12/1997 | Flaherty et al. |
| 5,702,363 A | 12/1997 | Flaherty |
| 5,704,520 A | 1/1998 | Gross |
| 5,726,404 A | 3/1998 | Brody |
| 5,726,751 A | 3/1998 | Altendorf et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson |
| 5,800,405 A | 9/1998 | McPhee |
| 5,810,015 A | 9/1998 | Flaherty |
| 5,814,020 A | 9/1998 | Gross |
| 5,839,467 A | 11/1998 | Saaski et al. |
| 5,840,063 A | 11/1998 | Flaherty |
| 5,845,218 A | 12/1998 | Altschul |
| 5,848,991 A | 12/1998 | Gross et al. |
| 5,851,197 A | 12/1998 | Marano et al. |
| 5,858,005 A | 1/1999 | Kriesel |
| D405,524 S | 2/1999 | Falk et al. |
| 5,865,806 A | 2/1999 | Howell |
| 5,871,470 A | 2/1999 | McWha |
| 5,875,393 A | 2/1999 | Altschul et al. |
| 5,886,647 A | 3/1999 | Badger et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,931,814 A | 8/1999 | Alex et al. |
| 5,935,099 A | 8/1999 | Peterson et al. |
| 5,954,058 A | 9/1999 | Flaherty |
| 5,957,890 A | 9/1999 | Mann et al. |
| 5,957,895 A | 9/1999 | Sage et al. ................... 604/181 |
| 5,961,492 A | 10/1999 | Kriesel et al. |
| 5,965,848 A | 10/1999 | Altschul et al. |
| 5,983,094 A | 11/1999 | Altschul et al. |
| 5,993,423 A | 11/1999 | Choi |
| 5,997,501 A | 12/1999 | Gross et al. |
| 6,019,747 A | 2/2000 | McPhee |
| 6,024,539 A | 2/2000 | Blomquist |
| 6,061,580 A | 5/2000 | Altschul et al. |
| 6,071,292 A | 6/2000 | Makower et al. |
| 6,144,847 A | 11/2000 | Altschul et al. |
| 6,152,898 A | 11/2000 | Olsen |
| 6,174,300 B1 | 1/2001 | Kriesel et al. |
| 6,190,359 B1 | 2/2001 | Heruth |

| | | |
|---|---|---|
| 6,206,850 B1 | 3/2001 | O'Neil |
| 6,375,638 B2 | 4/2002 | Nason et al. |
| 6,520,936 B1 | 2/2003 | Mann |
| 6,527,744 B1 | 3/2003 | Kriesel et al. |

OTHER PUBLICATIONS

International Search Report (PCT/US03/16640).

Web-Site Brochure dated Jan. 4, 2000. MiniMed 508. "Doing its job. Naturally." www.minimed.com/tiles/mm_113.htm.

Web-Site Brochure dated Dec. 20, 1999. Applied Medical Technology. "508 Pump Information". www.applied-medical.co.uk/508.htm.

Web-Site Brochure dated Jan. 4, 2000. "The Glucose Sensor". www.animascorp.com/sensor_f.html.

Web-Site Brochure dated Dec. 20, 1999. "The Animas R-1000 Insulin Pump", www.animascorp.com/pump_f_s.html.

Web-Site Brochure dated Dec. 20, 1999. "The Animas R-1000 Insulin Pump". www.animascorp.com/pump_f_f.html.

Web-Site Brochure dated Jan. 4, 2000. SOOIL-Homepage. "Portable Insulin Pump". www.sooil.com/intro2.htm.

Web-Site Brochure dated Jan. 4, 2000. SOOIL-Homepage. "Portable Insulin Pump". www.sooil.com/product2.htm.

Web-Site Brochure dated Jan. 4, 2000. SOOIL-Homepage. "Portable Insulin Pump". www.sooil.com/product3.htm.

Web-Site Brochure dated Jan. 4, 2000. SOOIL-Homepage. "Portable Insulin Pump". www.sooil.com/product4.htm.

User's Guide for Model 508 Insulin Pump, MiniMed, Aug. 2000, 145 pages.

Copy of PCT International Search Report dated Mar. 4, 2002; 5pp.

International Search Report (PCT/US03/12370).

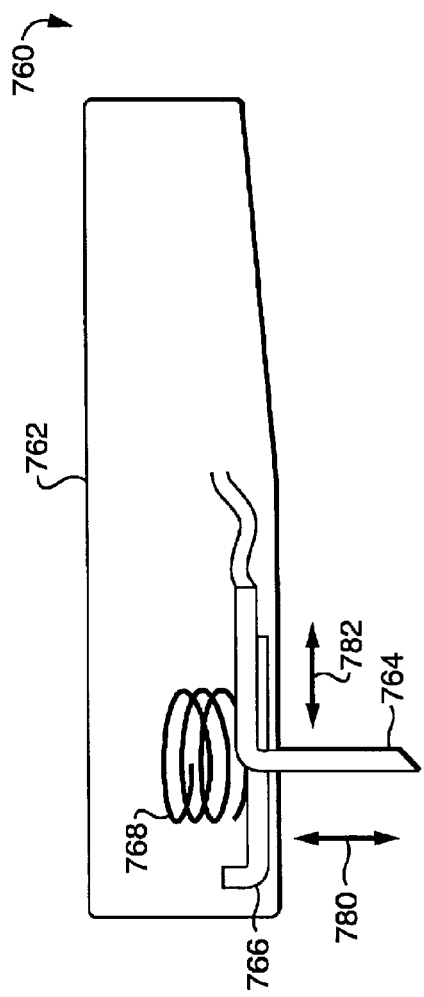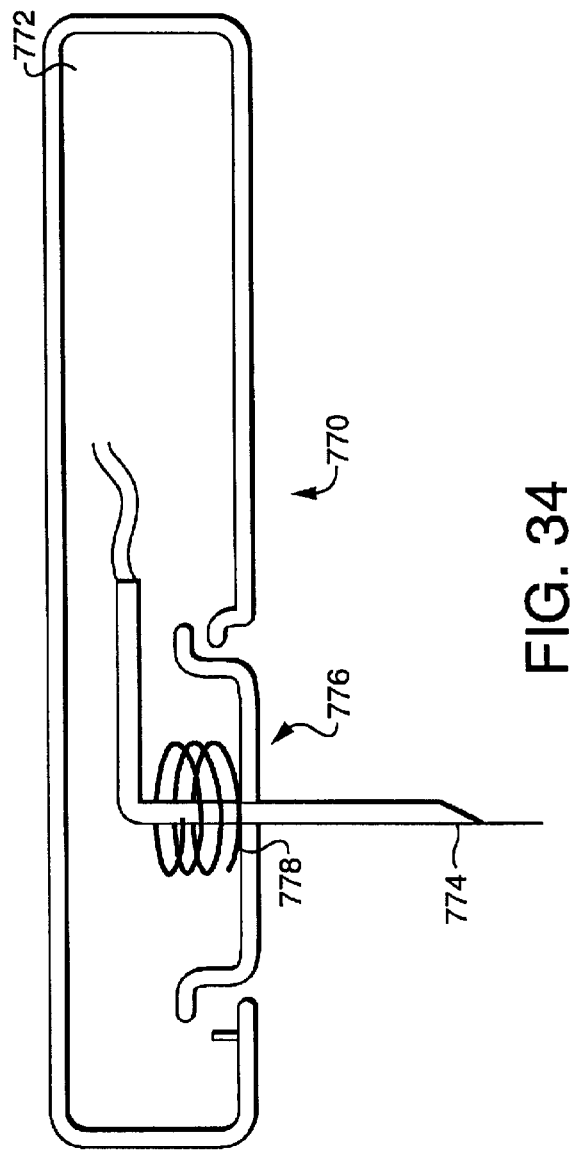

TRANSCUTANEOUS FLUID DELIVERY SYSTEM

FIELD OF THE INVENTION

The present invention relates generally to devices for delivering therapeutic fluids and more particularly to small, disposable, portion infusion devices and methods that can be used to transcutaneously deliver these fluids safely and simply to a mammalian patient. Even more particularly, the present invention relates a transcutaneous infusion assembly that allows transcutaneous placement of a soft cannula safely and automatically, and does not require the disposal of a sharp, contaminated needle.

BACKGROUND OF THE INVENTION

Today, there are numerous diseases and other physical ailments that are treated by various medicines including pharmaceuticals, nutritional formulas, biologically derived or active agents, hormonal and gene-based material and other substances in both solid or liquid form. In the delivery of these medicines, it is often desirable to bypass the digestive system of a mammalian patient to avoid degradation of the active ingredients caused by the catalytic enzymes in the digestive tract and liver. Delivery of a medicine other than by way of the intestines is known as parenteral delivery. Parenteral delivery of various drugs in liquid form is often desired to enhance the effect of the substance being delivered, insured that the unaltered medicine reaches its intended site at a significant concentration. Also, undesired side effects associated with other routes of delivery, such as systemic toxicity, can potentially be avoided. Often, a medicine may only be available in a liquid form, or the liquid version may have desirable characteristics that cannot be achieved with solid or pill form. Delivery of liquid medicines may best be accomplished by infusing directly into the cardiovascular system via veins or arteries, into the subcutaneous tissues or directly into organs, tumors, cavities, bones or other site-specific locations within the body.

Parenteral delivery of liquid medicines into the body is often accomplished by administering bolus injection using a needle and reservoir, or continuously by gravity driven dispensers or transdermal patch technologies. Bolus injections often imperfectly match the clinical needs of the patient, and usually require larger individual doses than are desired at the specific time they are given. Continuous delivery of medicine through gravity feed systems compromise the patient's mobility and lifestyle, and limit the therapy to simplistic flow rates and profiles. Transdermal patches have special requirements of the medicine being delivered, particularly as it relates to the molecular structure, and similar to gravity feed systems, the control of the drug administration is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. An example of a use of an ambulatory infusion pump is for the delivery of insulin for the treatment of diabetes mellitus. These pumps can deliver insulin on a continuous basal basis as well as a bolus basis as is disclosed in U.S. Pat. No. 4,498,843 to Schneider et al. The ambulatory pumps often work with a storage device to contain the liquid medicine, such as a cartridge or reservoir, and use electro-mechanical pumping or metering technology to deliver the medication to the patient via tubing from the infusion device to needle that is inserted transcutaneously, or through the skin of the patient. The devices allow control and programming via electromechanical buttons or switches located on the housing of the device, and accessed by the patient or clinician. The devices include visual feedback via text or graphic screens, such as liquid crystal displays known as LCD's, and may include alert or warning lights and audio or vibration signals and alarms. The device can be worn in a harness or pocket or strapped to the body of the patient.

Currently available ambulatory infusion devices are expensive, difficult to program and prepare for infusion, and tend to be bulky, heavy and very fragile. Filling these devices can be difficult and require the patient to carry both the intended medication as well as filing accessories. The devices require specialized care, maintenance, and cleaning to assure proper functionality and safety for their intended long-term use. Due to the high cost of existing devices, healthcare providers limit the patient populations approved to use the devices and therapies for which the devices can be used.

Clearly, therefore, there is a need for a programmable and adjustable infusion system that is precise and reliable and can offer clinicians and patients a small, low cost, light weight, simple to use alternative for parenteral delivery of liquid medicines.

In response, the applicant of the present application provides a small, low cost, lightweight, easy to use device for delivery liquid medicines to a patient, which is described in co-pending U.S. application Ser. No. 09/943,992, filed on Aug. 3, 2001. The device includes an exit port, a dispenser for causing fluid from a reservoir to flow to the exit port, a local processor programmed to cause a flow of fluid to the exit port based on flow instructions from a separate, remote control device, and a wireless receiver connected to the local processor for receiving the flow instructions. To reduce the size, complexity and costs of the device, the device is provided with a housing that is free of user input components, such as a keypad, for providing flow instructions to the local processor.

What is still desired, however, are new and improved devices for delivering fluid to a patient.

SUMMARY OF THE INVENTION

The applicant has determined that a sophisticated ambulatory infusion device that can be programmed to reliably deliver variable flow profiles of liquid medications, yet is small, lightweight and low cost, is needed. Avoiding the general upkeep and maintenance required by expensive, long-term use devices is necessary for broader acceptance of ambulatory infusion therapy. Smaller and lighter devices are easier to carry and are more comfortable for the patient even allowing the device to attach with adhesive to the patient's skin similar to a transdermal patch.

The fluid delivery devices of the present invention are simple in design, and inexpensive and easy to manufacture, to further reduce the size, complexity and costs of the devices, such that the devices or portions thereof lend themselves to being small and disposable in nature. In addition, the fluid delivery devices may include a transcutaneous infusion assembly that allows transcutaneous placement of a soft cannula safely and automatically, and does not require the disposal of sharp, contaminated needle.

An inexpensive device allows greater flexibility in prescribing the device for use by reducing the financial burden on healthcare insurance providers, hospital and patient care centers as well as patients themselves. In addition, low cost devices make it more practical for a patient to have one or more replacement devices readily available. If the primary devices is lost or becomes dysfunctional, availability of the replacement eliminates costly expedited repair and avoids periods of discontinued ambulatory therapy.

According to one embodiment of the invention, a device for delivery fluid to a person includes a reservoir for containing a fluid to be delivered to the person; a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device; a housing containing the reservoir and the fluid transport device, the housing including an exit port for receiving the distal end of the fluid transport device upon injection of the distal end into the person and means for securing a first wall of the housing to the skin of the person; and an injection activation device including a driving mechanism contacting the fluid transport device for driving the penetrating member from a first position within the housing, through the exit port to a second position, external to the housing and into the skin of the person.

The driving mechanism of the injection activation device may include a plunger having a body portion extending through an aperture in a second wall of the housing and in frictional contact with the distal end of the fluid transport device, such that the application of a longitudinal force to the plunger devices the penetrating member from the first position to the second position. The plunger may include a friction member disposed on the body portion, the friction member causing the body portion of the plunger to have a width dimension which is slightly large than a width dimension of the aperture of the housing, thus requiring a specific longitudinal force to be applied to the plunger to enable the friction member to pass through the aperture, the specific force being translated to the distal end of the fluid transport device. The friction member may be an annular flange. The plunger may further include a head portion for stopping travel of the plunger by contacting the housing. The plunger may be removable from the housing after the penetrating member is driven to the second position. The driving mechanism of the injection activation device may include a plunger contained within the housing, the plunger having a first end including a lateral protrusion and a second end in frictional contact with the distal end of the fluid transport device, the injection activation device further including a biasing spring for biasing the plunger for driving the penetrating member from the first position to the second position, and the lateral protrusion being in contact with an internal ridge of the housing, with the penetrating member in the first position, thereby preventing the plunger from driving the penetrating member from the first position to the second position; the housing including an actuator for urging the lateral protrusion from the internal ridge, thereby causing the plunger to drive the penetrating member from the first position to the second position. The actuator may include a finger coupled to an inside surface of a flexible wall portion of the housing, a distal end of the finger being in contact with the lateral protrusion such that an application of pressure to the flexible wall portion causes the finger to urge the lateral protrusion from the ridge, thereby causing the plunger to drive the penetrating member from the first position to the second position. The distal end of the finger, upon the application of pressure to the flexible wall portion, may move in same the direction as the flexible wall portion. The distal end of the finger, upon the application of pressure to the flexible wall portion, may move in a substantially opposite direction as the flexible wall portion. The finger may include a pivot which causes the distal end of the finger to move in a direction substantially opposite that of the flexible wall portion. The driving mechanism of the injection activation device may include a pivoting arm and the injection activation device further includes a latch assembly, the pivoting arm having a proximal end pivotally coupled to an inside surface of a wall of the housing and a distal end in contact with the latch assembly integral with a side wall of the housing, the fluid transport device being coupled to the arm such that when the distal end of the arm is in contact with the latch assembly, the penetrating member is in the first position; the injection activation device further includes a biasing spring attached between the proximal and distal ends of the arm and a wall of the housing, the biasing spring urging the arm to drive the penetrating member to the second position; and the latch assembly includes a latch for contacting the distal end of the pivoting arm to prevent the pivoting arm from driving the penetrating member from the first position to the second position under the influence of the biasing spring and a latch release mechanism for moving the latch out of contact with the distal end of the pivoting arm, thereby enabling the pivoting arm to drive the penetrating member from the first position to the second position under the influence of the biasing spring. The latch release mechanism may include an electrically driven actuator coupled between the latch and the side wall of the housing, such that, upon the application of a charge to the electrically driven actuator, the electrically driven actuator activates to pull the latch out of contact with the distal end of the pivoting arm. The electrically driven actuator may include one of a shape memory alloy, a shape memory polymer, a piezo electric actuator and a solenoid. The device may further include a local processor connected to the latch release mechanism and programmed to apply to charge to the electrically driven actuator based on injection instructions; and a wireless receiver connected to the local processor for receiving injection instructions from a separate, remote control device and delivering the injection instructions to the local processor. The housing may be free of user input components for providing injection instructions to the local processor. The device may further include a remote control device separate from the fluid delivery device, the remote control device including a remote processor; user interface components connected to the remote processor for transmitting the injection instructions to the remote processor; and a transmitter connected to the remote processor for transmitting the injection instructions to the receiver of the fluid delivery device. The latch release mechanism may include a mechanical lever coupled to the latch and protruding through the side wall, such that, upon the lever being pulled away from the housing, the latch is pulled out of contact with the distal end of the pivoting arm. The injection activation device may include a discrete secondary housing, the plunger including a first end having a lateral protrusion and a second end in frictional contact with the distal end of the fluid transport device, the second end of the plunger extending from within the secondary housing, out of a distal end thereof into the aperture of the housing and into frictional contact with the distal end of the fluid transport device; the injection activation device may further include a biasing spring coupled between the first end of the plunger and a proximal end of the secondary housing within the secondary housing for biasing the plunger for driving the penetrating member from the first position to the second position, the lateral protrusion being in contact with an internal ridge of the secondary housing, with the penetrating member in the first position, thereby preventing the plunger from driving the penetrating member from the first position to the second position; the secondary housing including an actuator for urging the lateral protrusion from the internal ridge, thereby causing the plunger to drive the penetrating member from the first position to the second position. The injection activation device may include a discrete secondary housing, the plunger including a first end having a lateral protrusion and a second end in frictional contact with the distal end of the fluid transport device, the second end of the plunger extending from within the secondary housing, out of a distal end thereof into the aperture of the housing and into frictional contact with the distal end of the fluid transport device. The injection activation device may further include a biasing spring coupled between the first end of the plunger and a proximal end of the secondary housing within the secondary housing for biasing the plunger for driving the penetrating member from the first position to the second position, the lateral protrusion being in contact with a latch assembly of the secondary housing, with the penetration member in the first position, thereby providing the plunger from driving the penetrating member from the first position to the second position. The latch assembly may include a latch for contacting the lateral protrusion of the plunger to prevent the plunger from driving the penetrating member from the first position to the second position under the influence of the biasing spring and a latch release mechanism coupled to the housing for moving the latch out of contact with the lateral protrusion, thereby enabling the plunger to drive the penetrating member from the first position to the second position under the influence of the biasing spring. The latch release mechanism may include an electrically driven actuator coupled between the latch and the side wall of the housing, such that, upon the application of a charge to the electrically driven actuator, the electrically driven actuator activates to pull the latch out of contact with the distal end of the pivoting arm. The latch release mechanism may include a mechanical lever coupled to the latch and protruding through the side wall, such that, upon an application of force to the lever, the latch is moved out of contact with the distal end of the pivoting arm. The driving mechanism may include a plunger having a first end in frictional contact with the distal end of the fluid transport device, the plunger being biased to drive the penetrating member from the first position to the second position, the injection activation device further comprising a latch for contacting the plunger to maintain the penetrating member in the first position, the latch including an electrically driven actuator coupled to the latch, such that, upon the application of a charge to the electrically driven actuator, the electrically driven actuator activates to pull the latch of contact with the plunger, thereby enabling the plunger to drive the penetrating means from the first position to the second position.

According to another embodiment of the invention, a device for delivering fluid to a person includes a reservoir for containing a fluid to be delivered to the person; a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device, the proximal end being connected to the distal end by a medical portion of the fluid transport device; a housing containing the reservoir and the fluid transport device, the housing including an exit port for receiving the distal end of the fluid transport device upon injection of the penetrating member into the person and means for securing a first wall of the housing to the skin of the person; and an injection activation device including a driving mechanism contacting the fluid transport device for driving the penetrating member from a first position within the housing, through the exit port to a second position, external to the housing and into the skin of the person. The medial portion is disposed substantially parallel to the first wall of the housing and includes a lateral protrusion which, with the penetrating member in the first position, is biased against a latch assembly of the injection activation device by a biasing spring of the injection activation device, which is coupled between the lateral protrusion and an internal ridge of the housing, the biasing spring being in an energized state such that, upon activating the latch assembly, the biasing spring devices the fluid transport device in a direction of travel substantially parallel to the first wall, resulting in the penetrating member being driven from the first position to the second position.

The distal end of the fluid transport device may be flexible and the housing may include a deflecting device in the path of travel of the fluid transport device, wherein, upon activating the latch assembly, the distal end of the fluid transport device contacts the deflecting device which causes the distal end of the fluid transport device to the deflected from the direction to travel substantially parallel to the first wall of the housing to a second direction of travel at an angle of at least 15. The second direction of travel may be up to 90. The latch assembly may include a latch for contacting the lateral protrusion of the fluid transport device to prevent the biasing spring from driving the penetrating member from the first position to the second position and a latch release mechanism coupled to the housing for moving the latch out of contact with the lateral protrusion, thereby enabling the biasing spring to drive the penetrating member from the first position to the second position. The latch release mechanism may include an electrically driven actuator coupled between the latch and the housing, such that, upon the application of a charge to the electrically driven actuator, the shape memory alloy wire contracts, pulling the latch out of contact with the lateral position of the fluid transport device. The electrically driven actuator may include one of a shape memory alloy, a shape memory polymer, a piezo electric actuator and a solenoid. The device may further include a local processor connected to the latch release mechanism and programmed to apply a charge to the electrically driven actuator based on injection instructions and a wireless receiver connected to the local processor for receiving injection instructions from a separate, remote control device and delivering the injection instructions to the local processor. The housing may be free of user input components for providing injection instructions to the local processor. The device may further include a remote control device separate from the fluid delivery device and including a remote processor, user interface components connected to the remote processor for transmitting the injection instructions to the remote processor; and a transmitter connected to the remote processor for transmitting the injection instructions to the receiver of the fluid delivery device. The latch release mechanism may include a mechanical lever coupled to the latch and protruding through the side wall, such that, upon an application of force to the lever, the latch is moved out of contact with the distal end of the pivoting arm. The biasing spring may include one of a torsional spring, a coil spring, a helical spring, a compression spring, an air spring, a wave spring, a conical spring, a constant force spring, a belleville spring and a behave spring.

According to another embodiment of the invention, a device for delivering fluid to a person includes a reservoir for containing a fluid to be delivered to the person; a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device; a housing containing the reservoir and the fluid transport device, the housing including an exit port for receiving the distal end of the fluid transport device upon injection of the distal end into the person and means for securing a first wall of the housing to the skin of the person; and an injection activation device including a driving mechanism contacting the fluid transport device for driving the penetrating member from a first position within the housing, through the exit port to a second position, external to the housing and into the skin of the person. The driving mechanism includes a layer having a first portion coupled to a drive axle and a second portion, opposite the first portion, contacting the fluid transport device. The injection activation device further comprising driving means operatively coupled to the drive axle for rotating the drive axle upon activation of the driving means, the second portion of the lever driving the penetrating member from the first position to the second position upon rotation of the drive axle.

The lever may include a disk and the driving means may include a motor. The driving means may include an energized coil spring disposed about the drive axle which, when deenergized, causes the drive axle to rotate.

According to another embodiment of the invention, a device for delivering fluid to a person includes a reservoir for containing a fluid to be delivered to the person; a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device, the proximal end being connected to the distal end by a medical portion of the fluid transport device; a housing containing the reservoir and the fluid transport device, the housing including an exit port of receiving the distal end of the fluid transport device upon injection of the distal end into the person and means for securing a first wall of the housing to the skin of the person; and an injection activation device including a driving mechanism contacting the fluid transport device for driving the penetrating member from a first position within the housing, through the exit port to a second position, external to the housing and into the skin of the person. The medical portion is disposed substantially parallel to the first wall of the housing and includes a lateral protrusion. The driving mechanism includes an urging device disposed on one side of the lateral protrusion, the urging device being movable into contact with the lateral protrusion to urge the lateral protrusion downward, relative to the urging device, causing the penetrating member to be driven from the first position to the second position.

According to another embodiment of the invention, a device for delivery fluid to a person includes a reservoir for containing a fluid to be delivered to the person; a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device; a housing containing the reservoir and the fluid transport device, the housing including an exit port for receiving the distal end of the fluid transport device upon injection of the distal end into the person and means for securing a first wall of the housing to the skin of the person; and an injection activation device containing the fluid transport device for driving the penetrating member from a first position within the housing, through the exit port to a second position, external to the housing and into the skin of the person. The fluid transport device includes a needle housed within a flexible cannula, the penetrating member being disposed at a distal end of the needle, the flexible cannula including a bellows portion proximate a distal end thereof, wherein, when the fluid transport device is in the first position, the bellows portion of the soft cannula is in a compressed state and the penetrating member extends beyond the distal end of the flexible cannula. The injection activation device includes a plunger having a body portion coupled to the fluid transport device between the proximal end and the bellows portion of the flexible cannula, such that the application of a first force in a first direction to the plunger drives the fluid transport device from the first position to the second position, wherein the penetrating member of the needle and the distal end of the flexible cannula extend through the exit port and into the skin of the person.

Upon application of a second force to the plunger in a second direction substantially opposite the first direction, the penetrating member of the needle may be retracted to a third position, and the bellows portion of the flexible cannula is extended, thereby enabling the distal end of the flexible cannula to remain in the second position. The plunger may extend through a second wall of the housing and includes a head portion exterior to the housing, the first force being applied directly to the head portion by a person to drive the fluid transport device from the first position to the second position. The second force may be applied directly to the head portion by person to move the penetrating member of the needle to the third position. The injection activation device may include a spring coupled between the plunger and an interior wall of the housing, the spring being in a deenergized state when the fluid transport device is in the first position and in an energized state when the fluid transport device is in the second position, wherein, upon a termination of the application of the first force, the spring applies the second force to the plunger, thereby causing the penetrating member to move to the third position. The plunger may include a lateral protrusion and the injection activation device includes a first spring in an energized state and positioned relative to the lateral protrusion to impart the first force upon releasing its energy and a second spring in an energized state and positioned relative to the lateral protrusion to impart the second force upon releasing its energy and the injection activation device includes a latch assembly for maintaining the first spring in its energized state and the second spring in its energized state. The latch assembly may include a first latch arm movable between a closed position, in which the first spring is maintained in the energized state and an open position, in which the first spring is released from the energized state, thereby imparting the first force to the lateral protrusion to drive the fluid transport device from the first position to the second position. The first latch arm may be held in the closed position by contact with the first spring and wherein the first latch arm is moved to the open state by a first latch activation device. The first latch activation device may include a first electrically driven actuator coupled to the latch arm, such that, upon the application of a charge to the first electrically driven actuator, the first electrically driven actuator activates, causing the latch arm to move from the closed position to the open position. The device of claim latch assembly may include a second latch arm movable between a closed position, in which the second spring is maintained in the energized state and an open position, in which the second spring is released from energized state, thereby imparting the second force to the lateral protrusion to drive the fluid transport device from the second position to the third position. The second latch arm may be held in the closed position by contact with the second spring and wherein the second latch arm is moved to the open state by a second latch activation device. The second latch activation device may include a second electrically driven actuator coupled between the second latch arm and the housing, such that, upon the application of a charge to the second electrically driven actuator, the second electrically driven actuator activates, causing the second latch arm to move from the closed position to the open position. The third position may be the first position. The third position may be within the housing and further away from the exit port than a first position. The third position may be between the first and second positions, such that the penetrating member is located between the distal end of the flexible cannula and the exit port of the housing. The fluid transport device may be constructed and arranged such that, upon activation of the first force, a medial portion of the needle, between the approximal and distal ends, travels in a direction substantially parallel to the first wall. The housing may further include a deflector located along a path of travel of the fluid transport device for imparting a bend of at least 15 to the distal end of the fluid transport device, thereby directing the distal end through the exit port as the fluid transport device is driven from the first position to the second position. The second latch activation device may include an urging device disposed on the lateral protrusion wherein, upon the first spring imparting the first force on the lateral protrusion, the urging device contacts the second latch arm and urges the second latch arm into its open position, thereby imparting the second force to the lateral protrusion.

According to another embodiment of the invention, a device for delivering fluid to a person includes a reservoir for containing a fluid to be delivered to the person; a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device, a housing containing the reservoir and the fluid transport device, the housing including an exit port for receiving the distal end of the fluid transport device upon injection of the distal end into the person and means for securing a first wall of the housing to the skin of the person; and an injection activation device containing the fluid transport device for driving the penetrating member from a first position within the housing, through the exit port to a second position, external to the housing and into the skin of the person. The fluid transport device includes a needle housed within a flexible cannula, the penetrating member being disposed at a distal end of the needle, the flexible cannula including a retraction prevention mechanism proximate a distal end thereof, wherein, when the fluid transport device is in the first position, the retraction prevention mechanism of the soft cannula is within the housing and the penetrating member extends beyond the distal end of the flexible cannula. The injection activation device includes a plunger having a body portion coupled to the fluid transport device, such that the application of a first force in a first direction to the plunger drives the fluid transport device from the first position to the second position, wherein the penetrating member of the needle and the distal end of the flexible cannula extend through the exit port and into the skin of the person and the retraction prevention mechanism of the flexible cannula is in contact with the exit port of the housing.

The retracting prevention mechanism may include a protrusion disposed on the flexible cannula, the protrusion causing the flexible cannula to have a width dimension greater than a width dimension of the exit port. The retraction prevention mechanism may include an annular ring disposed on the flexible cannula and having a greater diameter than a diameter of the exit port. The retraction prevention mechanism may include an externally roughened portion of the flexible cannula. The retraction prevention mechanism may include one or more barbs disposed on an exterior surface of the flexible cannula. Upon application of a second force to the plunger in a second direction substantially opposite the first direction, the penetrating member of the needle may be retracted to a third position, and the retraction prevention mechanism of the flexible cannula may remain in contact with the exit port, thereby forcing the distal end of the flexible cannula to remain in the second position. The plunger may extend through a second wall of the housing and includes a head portion exterior to the housing, the first force being applied directly to the head portion by a person to drive the fluid transport device from the first position to the second position. The second force may be applied directly to the head portion by a person to move the penetrating member of the needle to the third position. The injection activation device may include a spring coupled between the plunger and an interior wall of the housing, the spring being in a deenergized state when the fluid transport device is in the first position and in an energized state when the fluid transport device is in the second position, wherein, upon a termination of the application of the first force, the spring applies the second force to the plunger, thereby causing the penetrating member to move to the third position. The plunger may include a lateral protrusion and the injection activation device includes a first spring in an energized state and positioned relative to the lateral protrusion to impart the first force upon releasing its energy and a second spring in an energized state and positioned relative to the lateral protrusion to impart the second force upon releasing its energy and the injection activation device includes a latch assembly for maintaining the first spring in its energized state and the second spring in its energized state. The latch assembly may include a first latch arm movable between a closed position, in which the first spring is maintained in the energized state and an open position, in which the first spring is released from the energized state, thereby imparting the first force to the lateral position to drive the fluid transport device from the first position to the second position. The first latch arm may be held in the closed position by contact with the first spring and wherein the first latch arm is moved to the open state by a first latch activation device. The first latch activation device may include a first electrically driven actuator coupled between the latch arm and the housing, such that, upon the application of a charge to the first electrically driven actuator, the first electrically driven actuator activates, causing the latch arm to move from the closed position to the open position. The latch assembly may include a second latch arm movable between a closed position, in which the second spring is maintained in the energized state and an open position, in which the second spring is released from the energized state, thereby imparting the second force to the lateral protrusion to drive the fluid transport device from the second position to the third position. The second latch arm is held in the closed position by contact with the second spring and wherein the second latch arm is moved to the open state by a second latch activation device. The second latch activation device comprises a second electrically driven actuator coupled between the second latch arm and the housing, such that, upon the application of a charge to the second electrically driven actuator, the second electrically driven actuator activates, causing the second latch arm to move from the closed position to the open position. The fluid transport device may be constructed and arranged such that, upon activation of the first force, a medical portion of the needle, between the proximal and distal ends, travels in a direction substantially parallel to the first wall. The housing may further include a deflector located along a path of travel of the fluid transport device for imparting a bend of at least 15 to the distal end of the fluid transport device, thereby directing the distal end through the exit port as the fluid transport device is driven from the first position to the second position. The second latch activation device may include an urging device disposed on the lateral protrusion wherein, upon the first spring imparting the first force on the lateral protrusion, the urging device contacts the second latch arm and urges the second latch arm into its open position, thereby imparting the second force. The housing may include a transparent portion disposed proximate the exit port, for providing a new of an entry site of the fluid transport device in the person's skin.

According to another embodiment of the invention, a device for delivering fluid to a person includes a reservoir for containing a fluid to be delivered to the person; a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device; a housing containing the reservoir and the fluid transport device, the housing including an exit port for receiving the distal end of the fluid transport device upon injection of the distal end into the person, means for securing a first wall of the housing to the skin of the person and a retraction prevention mechanism proximate the exit port; and an injection activation device contacting the fluid transport device for driving the penetrating member from a first position within the housing, through the exit port to a second position, external to the housing and into the skin of the person. The fluid transport device includes a needle housed within a flexible cannula, the penetrating member being disposed at a distal end of the needle. The injection activation device includes a plunger having a body portion coupled to the fluid transport device, such that the application of a first force in a first direction to the plunger drives the fluid transport device from the first position to the second position, wherein the penetrating member of the needle and the distal end of the flexible cannula extend through the exit port and into the skin of the person, the distal end of the flexible cannula being in frictional contact with the retraction prevention mechanism of the housing.

Upon application of a second force to the plunger in a second direction substantially opposite the first direction, the penetrating member of the needle may be retracted to a third position, and the retraction prevention mechanism of the housing maintains the distal end of the flexible cannula in the second position. The retraction prevention mechanism may include an externally roughened portion of the exit port. The retraction prevention mechanism may include one or more barbs disposed on a cannula-contacting surface of the exit port.

According to another embodiment of the invention, a device for delivering fluid to a person includes a reservoir for containing a fluid to be delivered to the person; a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device; a housing containing the reservoir and the fluid transport device, the housing including an exit port for receiving the distal end of the fluid transport device upon injection of the distal end into the person and means for securing a first wall of the housing to the skin of the person; and an injection activation device contacting the fluid transport device for driving the penetrating member from a first position within the housing, through the exit port to a second position, external to the housing and into the skin of the person. The fluid transport device includes a needle housed within a flexible cannula, the penetrating member being disposed at a distal end of the needles, beyond a distal end of the flexible cannula, the flexible cannula having a length that is less than a length of the needle, wherein a proximal end of the flexible cannula, opposite the distal end of the needle, is constructed and arranged to provide a frictional seal between the flexible cannula and the needle, the frictional seal preventing an escape of the fluid from between the distal end of the cannula and the needle, while allowing the distal end of the cannula to slide along the needle. The injection activation device includes a plunger coupled to the fluid transport device, such that the application of a first force in a first direction to the plunger drives the fluid transport device from the first position to the second position, wherein the penetrating member of the needle and the distal end of the flexible cannula extend through the exit port and into the skin of the person.

The plunger may include a first body portion coupled to the flexible cannula and a second body portion coupled to the needle and in contact with the first body portion, wherein, upon the application of the first force, the second body portion drives the needle, the first body portion and the flexible cannula from the first position to the second position. Upon the application of a second force to the second body portion, in a direction substantially opposite the first direction, the second body portion and the needle may be retracted to a third position. The injection activation device may further include a retention member for contacting the flexible cannula to retain the cannula in the second position prior to the application of the second force, thereby enabling the needle to be driven to the third position independent of the flexible cannula. The injection activation device may further include a first latch mechanism for maintaining the fluid transport device in the first position prior to the application of the first force According to another embodiment of the invention, a device for delivering fluid to a person includes a reservoir for containing a fluid to be delivered to the person; a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device; a housing containing the reservoir and the fluid transport device, the housing including an exit port for receiving the distal end of the fluid transport device upon injection of the distal end into the person and means for securing a first wall of the housing to the skin of the person; and an injection activation device including a driving mechanism contacting the fluid transport device for driving the penetrating member from a first position within the housing, through the exit port to a second position, external to the housing and into the skin of the person. The fluid transport device includes a needle housed within a flexible cannula, the penetrating member being disposed at a distal end of the needle, the flexible cannula including a retraction prevention mechanism proximate a distal end thereof, wherein, when the fluid transport device is in the first position, the retraction prevention mechanism of the soft cannula is within the housing and the penetrating member extends beyond the distal end of the flexible cannula. The driving mechanism includes a rotational-to-linear motion converter coupled between rotational driving means of the injection activation device and the fluid transport device for converting rotational motion imparted on a drive shaft of the rotational-to-linear motion converter by the rotational drive means to linear motion which causes the driving mechanism to drive the penetrating member from the first position to the second position during a first portion of rotational travel of the drive shaft.

The rotational-to-linear motion converter may be operative for retracting the penetrating member to a third position during a second portion of rotational travel of the drive shaft. The rotational-to-linear motion converter may further include a crank coupled to the drive shaft, the crank including an urging rod; and the injection activation device including a force translator coupled to the fluid transport device, the force translator having a longitudinal slot for receiving the urging rod such that, upon rotation of the drive shaft and crank, the force translator converts rotational motion of the urging rod to a linear motion imparted on the fluid transport device to drive the penetrating member from the first position to the second and third positions. The driving means may include a motor. The driving means may include a spring in an energized state disposed about the drive axle which, when deenergized, causes the drive axle to rotate. The injection activation device further comprising a latch arm movable between a closed position, maintaining the spring in the energized state, and an open position, in which the spring is released from the energized state, thereby causing the drive axle to rotate. The latch arm may be held in the closed position by contact with the crank and wherein the latch arm is moved to the open state by a latch activation device. The latch activation device may include an electrically driven actuator coupled to the latch arm such that, upon the application of a charge to the first electrically driven actuator, the first electrically driven actuator activates, causing the latch arm to move from the closed position to the open position.

According to another embodiment of the invention, a device for delivering fluid to a person includes a reservoir for containing a fluid to be delivered to the person; a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device; a housing containing the reservoir and the fluid transport device, the housing including an exit port for receiving the distal end of the fluid transport device upon injection of the distal end into the person and means for securing a first wall of the housing to the skin of the person; and an injection activation device contacting the fluid transport device for driving the penetrating member from a first position within the housing, through the exit port to a second position, external to the housing and into the skin of the person. The fluid transport device includes a needle housed within a flexible cannula, the penetrating member being disposed at a distal end of the needle, the flexible cannula including a retraction prevention mechanism proximate a distal end thereof, wherein, when the fluid transport device is in the first position, the retraction prevention mechanism of the soft cannula is within the housing and the penetrating member extends beyond the distal end of the flexible cannula. The injection activation device includes a latch arm for maintaining the fluid transport device in the first position when the latch arm is in a closed state and a first spring in an energized state coupled to the fluid transport device, such that, upon releasing the latch arm, the first spring deenergizes causing the penetrating member to be driven from the first position to the second position, wherein the penetrating member of the needle and the distal end of the flexible cannula extend through the exit port and into the skin of the person and the retraction prevention mechanism of the flexible cannula is in contact with the exit port of the housing.

The first spring may include a leaf spring having a distal end in contact with the fluid transport device which, upon the penetrating member being driven to the second position, falls out of contact with the fluid transport device. The injection activation device may further include a second spring coupled to the fluid transport device which is in a deenergized state when the penetrating member is in the first position and which becomes energized as the penetrating member is driven from the first position to the second position upon release of the latch arm, such that, when the penetrating member reaches the second position, the second spring is energized such that, when the first spring falls out of contact with the fluid transport device, the second spring retracts the penetrating member to a third position, while the retraction prevention mechanism of the flexible cannula remains in contact with the exit port, thereby forcing the distal end of the flexible cannula to remain in the second position. The latch arm may be maintained in the closed position by contact with the fluid transport device and wherein the latch is released by a latch activation device. The latch activation device may include an electrically driven actuator coupled to the latch arm such that, upon the application of a charge to the first electrically driven actuator, the first electrically driven actuator activates, causing the latch arm to move from the closed state to the open state. The driving mechanism may include a sliding device disposed in a ramp portion of the injection activation device and in contact with the fluid transport device, the ramp portion being disposed relative to the fluid transport device such that, as the sliding device is moved along the ramp portion, an urging member of the sliding device slides between the ramp portion and the fluid transport device, causing the fluid transport device to be driven from the first position to the second position. The sliding device may further include a handle portion external of the housing, for enabling a user of the device to manually slide the urging member along the ramp portion to drive the fluid transport device from the first position to the second position. The plunger may include a body portion coupled to the needle and in contact with the proximal end of the flexible cannula, wherein upon the application of the first force in the first direction, the body portion drives the needle and the flexible cannula from the first position to the second position. Upon the application of a second force to the second body portion, in a direction substantially opposite the first direction, the body portion and the needle are retracted to a third position. The injection activation device may further include a retention member for contacting the flexible cannula to retain the cannula in the second position prior to the application of the second force, thereby enabling the needle to be driven to the third position independent of the flexible cannula. The injection activation may further include a spring which is in an energized state while the fluid transport device is the first position. When the spring is deenergized, the spring may apply the first force to the plunger during a first portion of deenergization, driving the fluid transport device from the first position to the second position. During a second portion of the deenergization, the spring may drive the plunger in the second direction, substantially opposite the first direction, thereby retracting the body portion and the needle to the third position. The injection activation device may further include a latch arm which, when in a closed state, maintains the fluid transport device in the first position and the spring in the energized state. The latch arm may be maintained in the closed position by contact with the fluid transport device and wherein the latch is released by a latch activation device. The latch activation device may include an electrically driven actuator coupled to the latch arm such that, upon the application of a charge to the first electrically driven actuator, the first electrically driven actuator activates, causing the latch arm to move from the closed state to the open state.

According to another embodiment of the invention, a device for delivering fluid to a person includes a reservoir for containing a fluid to be delivered to the person; a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device; a housing containing the reservoir and the fluid transport device, the housing including an exit port for receiving the distal end of the fluid transport device upon injection of the distal end into the person and means for securing a first wall of the housing to the skin of the person; and an injection activation device contacting the fluid transport device for driving the penetrating member from a first position within the housing through the exit port to a second position, external to the housing and into the skin of the person. The fluid transport device includes a needle housed within a flexible cannula, the penetrating member being disposed at a distal end of the needle, the flexible cannula including a retraction prevention mechanism proximate a distal end thereof, wherein, when the fluid transport device is in the first position, the retraction prevention mechanism of the soft cannula is within the housing and the penetrating member extends beyond the distal end of the flexible cannula. The injection activation device includes a cam and a follower portion slidably coupled to the fluid transport device, the cam including a first cam portion and a second cam portion, the fluid transport device being in the first position when the follower portion is in contact with the first cam portion and in the second position when the follower portion is in contact with the second cam portion, wherein the penetrating member of the needle and the distal end of the flexible cannula extend through the exit port and into the skin of the person and the retraction prevention mechanism of the flexible cannula is in contact with the exit port of the housing; and driving means for driving the follower portion from the first cam portion to the second cam portion.

The injection activation device may further include a third cam portion, the driving means driving the follower portion from the second cam portion to the third cam portion, such that, as the follower portion is driven from the second cam portion to the third cam portion, the needle is retracted to a third position. The driving means may include a spring biased for driving the following portion from the first cam portion through the second cam portion to the third cam portion. When the follower portion is in contact with the first cam portion, the spring may be in an energized state. The injection activation device may further include a latch arm which, when in a closed state, maintains the spring in the energized state. The latch arm may be maintained in the closed position by contact with the spring and wherein the latch is released by a latch activation device. The latch activation device includes an electrically driven actuator coupled to the latch arm such that, upon the application of a charge to the first electrically driven actuator, the first electrically driven actuator activates, causing the latch arm to move from the closed state to the open state. The first force may be imparted to the fluid transport device by a first spring and the second force is imparted to the fluid transport device by a spring; the first spring having a proximal end coupled to the needle and in contact with the flexible cannula and a distal end coupled to a distal end of the second spring; the second spring having a proximal end which is in a fixed position with respect to the housing; the first and second springs being in an energized state when the fluid transport device in the first position. The injection activation device may further include a unitary control mechanism which contacts the first and second springs to maintain them in the energized states, the control mechanism having a first finger contacting the proximal end of the first spring and as second finger contacting the distal end of the second spring, the first finger being shorter than the second finger. Upon moving the control mechanism away from the first and second springs, the first finger releases the proximal end of the first spring, causing the fluid transport device to be driven from the first position to the second position by the first force; and after the application of the first force, the second finger releases the distal end of the second spring, causing the needle to be retracted from the second position to the third position by the second force.

According to another embodiment of the invention, a device for delivering fluid to a person includes a reservoir for containing a fluid to be delivered to the person; a fluid transport device for dispensing fluid from the reservoir to the person, the fluid transport device including a proximal end in fluid communication with the reservoir and a distal end having a means for facilitating the delivery of fluid to the person through the fluid transport device when inserted into the skin of the person; a housing containing the reservoir and the fluid transport device, the housing including an exit port for receiving the distal end of the fluid transport device upon injection of the distal end into the person and means for securing the first wall of the housing to the skin of the person; and a motion isolation device for isolating motion of the housing from the fluid transport device when the penetrating member is external to the housing and within the skin of the person.

The motion isolation device may include a spring mechanism coupled between the fluid transport device and the housing, the spring mechanism enabling the housing to move independently of the fluid transport device. The fluid transport device may include a flexible cannula and the motion isolation device comprises a loop in the flexible cannula between the distal end of the flexible cannula and a medial portion of the flexible cannula which is fixed to the housing, the loop portion enabling the housing to move independently of the flexible cannula.

The plunger may be formed from a transparent material for providing a view of an injection site of the penetrating member. The plunger may provide a magnified view of the injection site. The device may further include illumination means for directing light to the injection site through the plunger.

According to another embodiment of the invention, a device for delivering fluid to a person includes a reservoir for containing a fluid to be delivered to the person; a fluid transport device for dispensing fluid from the reservoir to the person, the fluid transport device including a proximal end in fluid communication with the reservoir and a distal end having a penetrating member for piercing the skin of the person to facilitate the delivery of fluid to the person through the fluid transport device; a housing containing the reservoir and the fluid transport device, the housing including an exit port for receiving the distal end of the fluid transport device upon injection of the distal end into the skin of the person; and an injection activation device contacting the fluid transport device for driving the penetrating member from a first position within the housing, through the exit port to a second position, external to the housing and into the skin of the person. The fluid transport device comprising a needle housed within a flexible cannula, the penetrating member being disposed at a distal end of the needle, wherein when the fluid transport device is in the first position, the penetrating member extends beyond the distal end of the flexible cannula. The injection activation device includes a plunger device coupled to the fluid transport device; a latch mechanism comprising a first latch arm for maintaining a first spring in an energized state and a second latch arm for maintaining a second spring in an energized state. Upon releasing the first latch arm, the first spring deenergizes and forces the plunger device and the fluid transport device from the first position to the second position and, upon the plunger and fluid transport device reaching the second position, the second latch arm is released, causing the second spring to deenergize and to force the plunger device from the second position to a third position.

The latch mechanism may include an electrically driven actuator coupled to the first latch arm such that, upon the application of a charge to the electrically driven actuator, the electrically driven actuator activates, causing the first latch arm to be released. The plunger device may include means for releasing the second latch arm, the releasing means contacting the second latch arm as the plunger device reaches the second position, thereby causing the second latch arm to be released.

BRIEF DESCRIPTION OF THE DRAWINGS

FIG. 33 is a cutaway view of another embodiment of a fluid delivery device in accordance with the present invention;

FIG. 34 is a cutaway view of another embodiment of a fluid delivery device in accordance with the present invention;

DETAILED DESCRIPTION

Figure 1:
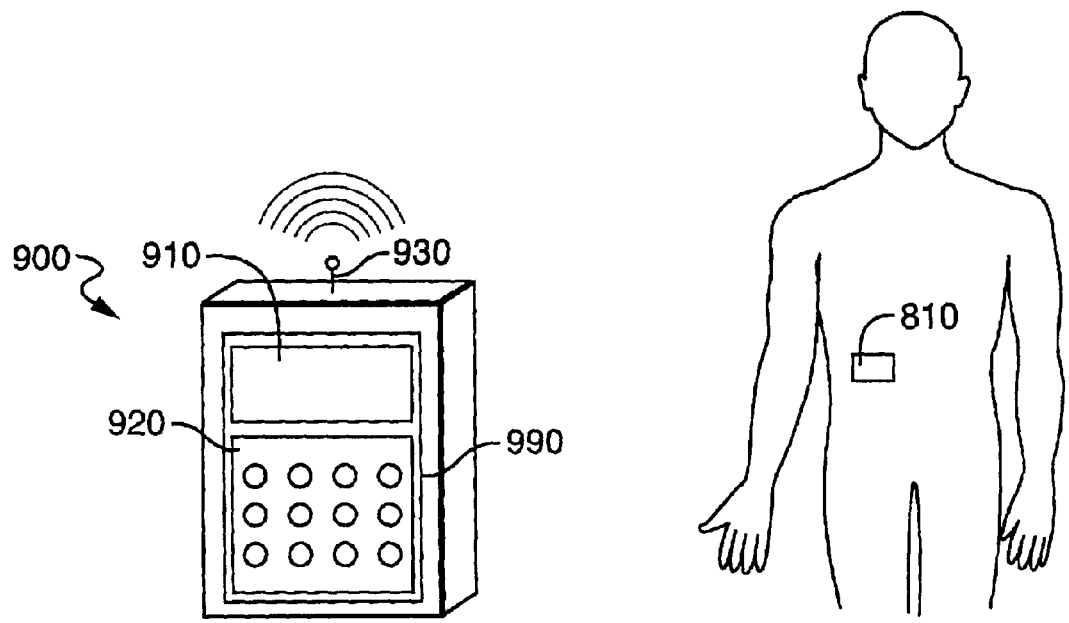
FIG. 1 is a perspective view of a first exemplary embodiment of a fluid delivery device constructed in accordance with the present invention and shown secured on a patient, and a remote control device for use with the fluid delivery device (the remote control device being enlarged with respect to the patient and the fluid delivery device for purposes of illustration)
Figure 2:
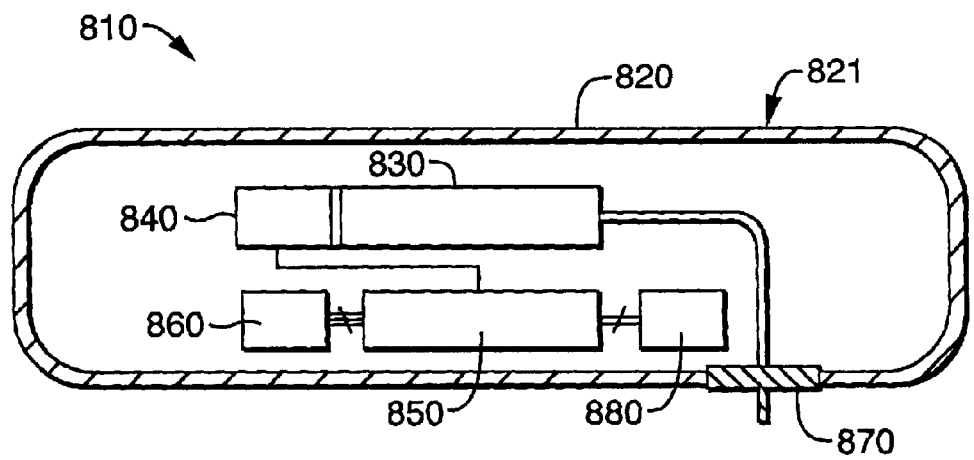
FIG. 2 is a sectional view of the fluid delivery device of FIG. 1, with a slidably movable penetrating member shown deploying a subcutaneous infusion cannula.

Referring to FIGS. 1 and 2, there is illustrated the various embodiment of a fluid delivery device constructed in accordance with the present invention. The types of liquids that can be delivered by the fluid delivery of the present invention include, but are not limited to, insulin, antibiotics, nutritional fluids, total parenteral nutrition or TPN, analgesics, morphine, hormones or hormonal drugs, gene therapy drugs, anticoagulants, cardiovascular medications, AZT or chemotherapeutics. The types of medical conditions that the fluid delivery device of the present invention might be used to treat include, but are not limited to, diabetes, cardiovascular disease, pain, chronic pain, cancer, AIDS, neurological diseases, Alzheimer's disease, ALS, hepatitis, Parkinson's disease or spasticity.

Referring to FIG. 2, the device 810 generally includes an exit port assembly 870 including a transcutaneous patient access tool, a dispenser 840 for causing fluid from a reservoir 830 to flow to the exit port assembly 870, and a processor or electronic microcontroller (hereinafter referred to as the "local" processor) 850 connected to the dispenser 840.

The local processor 850 is programmed to cause a flow of fluid to the exit port assembly 870 based on flow instructions from a separate, remote control device 900, an example of which is shown in FIG. 1. Referring to FIG. 2, the fluid delivery device 810 further includes a wireless receiver 860 connected to the local processor 850 for receiving the flow instructions from the separate, remote control device 900 and delivering the flow instructions to the local processor. The device 810 also includes a housing 820 containing the exit port assembly 870, the reservoir 830, the dispenser 840, the local processor 850, and the wireless receiver 860.

As shown, the housing 820 is free of user input components for providing flow instructions to the local processor 850, such as electromechanical switches or buttons on an outer surface 821 of the housing, or interfaces otherwise accessible to a user to adjust the programmed flow rate through the local processor 850. The lack of user input components allows the size, complexity and costs of the device 810 to be substantially reduced so that the device 810 lends itself to being small and disposable in nature.

In order to program, adjust the programming of, or otherwise communicate user inputs to the local processor 850, the fluid delivery device 810 includes the wireless communication element, or receiver 860 for receiving the user inputs from the separate, remote control deviced 900 of FIG. 1. Signals can be sent via a communication element (not shown) of the remote control device 900, which can include or be connected to an antenna 930, shown in FIG. 1 as being external to the device 900.

Referring to FIGS. 1 and 2, the remote control device 900 has user input components, including an array of electromechanical switches, such as the membrane keypad 920 shown. The control device 900 also includes user output components, including a visual display, such as a liquid crystal display (LCD) 910. Alternatively, the control device can be provided with a touch screen for both user input and output. Although not shown in FIG. 1, the remote control device 900 has its own processor (hereinafter referred to as the "remote" processor) connected to the membrane keypad 920 and the LCD 910. The remote processor receives the user inputs from the membrane keypad 920 and provides "flow" instructions for transmission to the fluid delivery device 810, and provides information to the LCD 910. Since the remote control device 900 also includes a visual display 910, the fluid delivery device 810 can be void of an information screen, further reducing the size, complexity and costs of the device 810.

The communication element 860 of the device 810 preferably receives electronic communication from the remote control device 900 using radio frequency or other wireless communication standards and protocols. In a preferred embodiment, the communication element 860 is a two-way communication element, including a receiver and a transmitter, for allowing the fluid delivery device 810 to send information back to the remote control device 900. In such an embodiment, the remote control device 900 also includes an integral communication element 860 comprising a receiver and a transmitter, for allowing the remote control device 900 to receive the information sent by the fluid delivery device 810.

The local processor 850 of the device 810 contains all the computer programs and electronic circuitry needed to allow a user to program the desired flow patterns and adjust the program as necessary. Such circuitry can include one or more microprocessors, digital and analog integrated circuits, resistors, capacitors, transistors and other semiconductors and other electronic components known to those skilled in the art. The local processor 850 also includes programming, electronic circuitry and memory to properly activate the dispenser 840 at the needed time intervals.

In the exemplary embodiment of FIG. 2, the device 810 includes a power supply 880, such as a battery or capacitor, for supplying power to the local processor 850. The power supply 880 is preferably integrated into the fluid delivery device 810, but can be provided as replaceable, e.g., a replaceable battery.

Although not shown, the device can include sensors or transducers such as a reservoir volume transducer or a reservoir pressure transducer, for transmitting information to the local processor 850 to indicate how and when to activate the dispenser 840, or to indicate other parameters determining flow, pump flowpath prime condition, blockage in flowpath, contact sensors, rotary motion or other motion indicators, as well as conditions such as the reservoir 830 being empty or leaking, or the dispensing of too much or too little fluid from the reservoir, etc.

The volume of the reservoir 830 is chosen to best suit the therapeutic application of the fluid delivery device 810 impacted by such factors as available concentrations of medicinal fluids to delivered, acceptable times between refills or disposal of the fluid delivery device 810, size constraints and other factors. The reservoir 830 may be prefilled by the device manufacturer or a cooperating drug manufacturer, or may include external filling means, such as a fill port having needle insertion septum or a Luer connector, for example. In addition, the device 810 can be provided with a removable reservoir.

Although not shown, the device 810 can also be provided with an adhesive layer on the outer surface of the housing 820 for securing the device 810 directly to the skin of a patient. The adhesive layer is preferably provided in a continuous ring encircling the exit port assembly 870 in order to provide a protective seal around the penetrated skin. The housing 820 can be made from flexible material, or can be provided with flexible hinged sections that allow the fluids delivery device 810 to flex during patient movement to prevent detachment and aid in patient comfort.

The dispenser 840 is connected in fluid communication with the reservoir 830, as shown in FIG. 2, and controlled by the local processor 850, which includes electronic programming, controls and circuitry to allow sophisticated fluid delivery programming and control of the dispenser 840. When the device 810 is provided with a pressurized reservoir 830 (i.e., fluid maintained within the reservoir at a pressure above atmospheric), the dispenser 840 is configured to act as a metering device, allowing pulses of fluid to pass from the pressurized reservoir 830, through the dispenser 840, to the exit port assembly 870 at atmospheric pressure. When the device 810 is provided with a non-pressurized reservoir 830, the dispenser 840 is configured to create a driving or pumping force on the fluid passing therethrough.

Figure 3A:
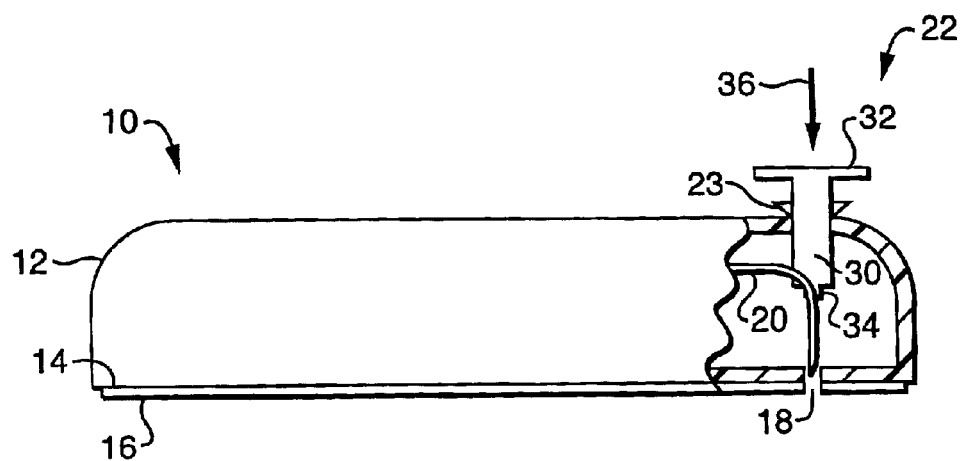
FIGS. 3A–3C are various views of one embodiment of a fluid delivery device in accordance with the present invention.
Figure 3B:
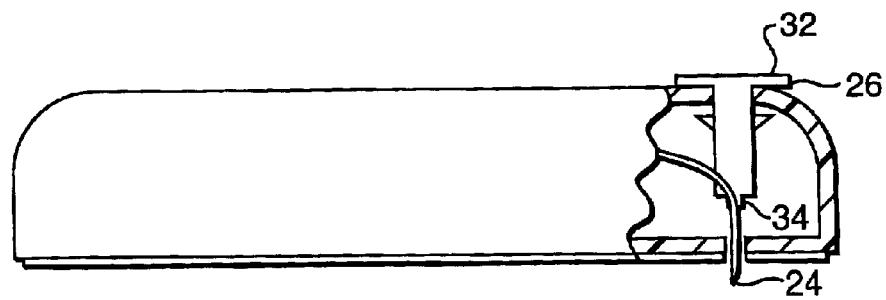
Figure 3C:
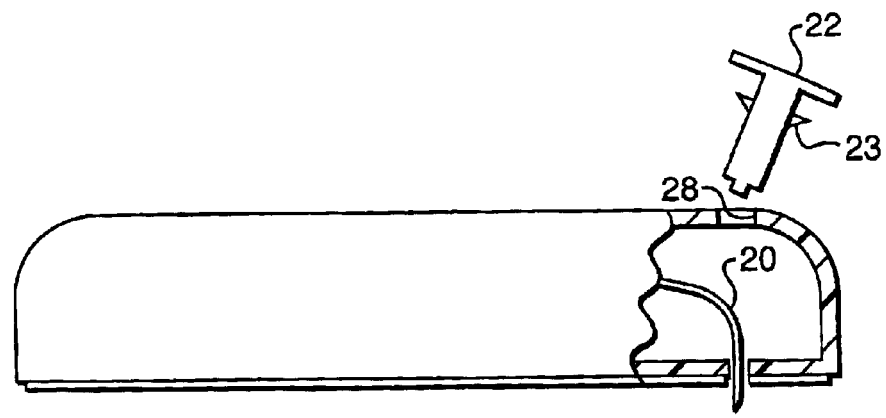

Referring now to FIGS. 3A–3C, a first embodiment of the fluid delivery device of the present invention includes a housing 12 for containing the reservoir and other control devices. The footprint of the housing 12 may be square, rectangular, oval or other geometry, depending on the size requirements for containing the reservoir and other control elements as well as the comfort requirements of the user. Housing 12 includes a first wall 14 having, preferably, an adhesive material 16 attached thereto for enabling the housing 12 to be adhered to the skin of the patient, thereby facilitating secured delivery of fluid to the person. While, in the preferred embodiment, the attachment means, as shown in FIG. 3, is an adhesive tape attached to the first wall 14 of the housing 12, it will be understood that any means for securing the housing 12 to the patient, such as simply taping the housing 12 to the skin of the patient, or securing the housing to the patient by means of a strap or other similar device.

Housing 12 further includes an exit port 18, disposed in the first wall 14, for enabling cannula 20 which, in this embodiment, is in the form of a rigid hollow needle having a penetrating portion 24, such as a sharpened point of the cannula 20 for penetrating the skin of the patient upon deployment of the cannula as described below. A plunger device 22 includes a body portion 30 which extends through an aperture 28 in a second wall of the housing 12, a head portion 32 and a cannula engagement portion 34 which maintains a frictional engagement with the cannula 20 when the cannula 20 is in the predeployment stage, or first position, shown in FIG. 3A. Plunger device 22 further includes one or more flanges 23 disposed along the body portion 30 thereof. As shown in FIG. 3A, flanges 23 are initially exterior to the housing 12 in the predeployment stage and cause the plunger device 22 to have a diameter at the point of the flanges 23 which is greater than the diameter of the aperture 28 of the housing 12. After the housing 12 has been attached to the patient, the cannula is deployed into the skin of the patient by applying manual pressure to the head 32 of the plunger device 22 in the direction shown by arrow 36 of FIG. 3A. Since the flanges 23 cause the body portion 30 to have a larger diameter at the point of the flanges 23 than the diameter of the aperture 28, a specific force is required to compress the flanges to a point where they will pass through the aperture 28. This force, once applied, is great enough to cause the plunger device 22 to force the cannula through the exit port 18 of the first wall 14 and into the skin of the patient, such as is shown in FIG. 3B.

The head 32 of plunger device 22 is formed such that when the plunger device is in the deployed stage, or second position, such as shown in FIG. 3B, a peripheral edge 26 of the head portion 32 is disposed relative to the housing 12 so as to expose an underside of the head 32 along the edge for facilitating the removal of the plunger device 22 by prying the plunger device 22 away from the housing 12 upon the application of pressure to the underside of the head portion 32. Cannula engagement portion 34 of the plunger device 22 is constructed to enable the plunger to force the cannula through the exit port 18 and into the skin of the patient, while allowing the plunger device 22 to be removed from the housing 12 such as is shown in FIG. 3C, and allowing the cannula 20 to remain in the deployed position shown in FIG. 3C. Once the cannula 20 is deployed into the skin of the patient, fluid delivery may be commenced.

Figure 4A:
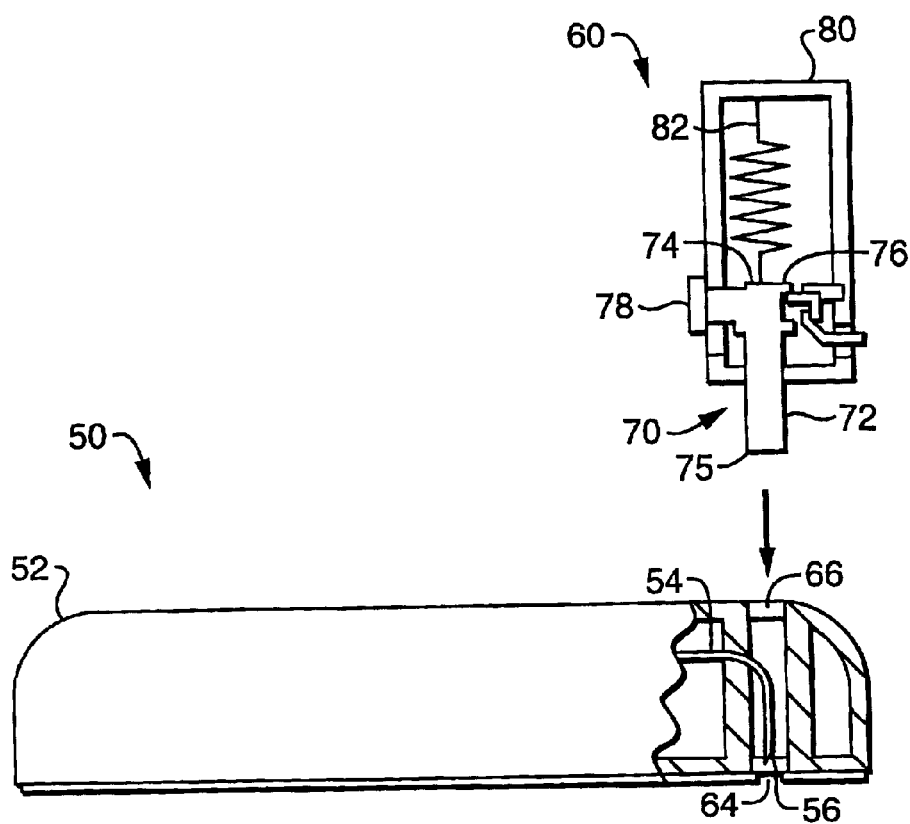
FIGS. 4A–4D are various views of another embodiment of a fluid delivery device in accordance with the present invention.
Figure 4B:
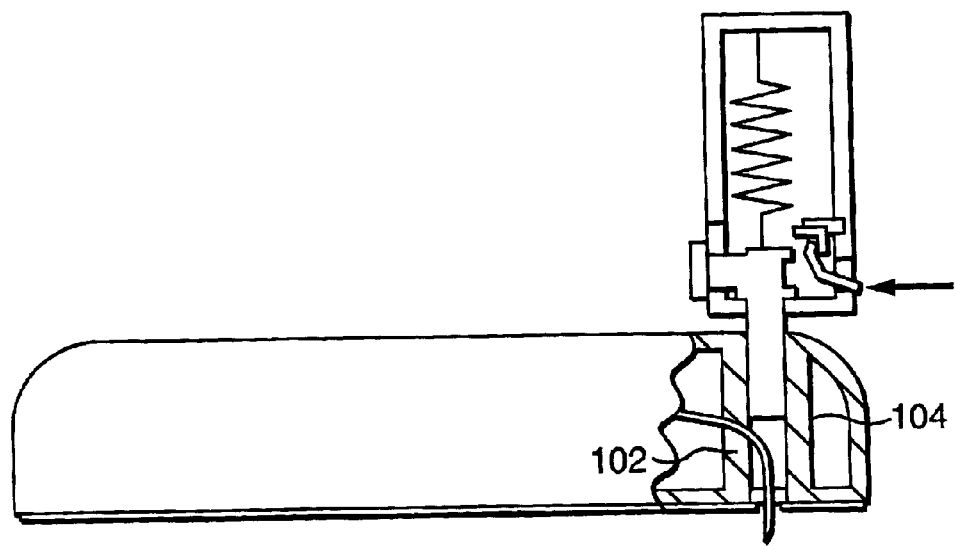

Referring now to FIGS. 4A and 4B, a second embodiment 50 of the present invention includes a housing 52 including a cannula 54 having a penetrating member 56 at a distal end thereof. Fluid delivery device 50 further includes a discrete injection actuator device 60. As shown in FIG. 4A, housing 52 includes an exit port 64 disposed to enable the cannula 54 to be deployed therethrough, and an actuator port 66 disposed opposite the exit port 64. Injection actuator 60 includes a plunger device 70, including a body portion 72, a head portion 74, a cannula engagement portion 75, a lateral protrusion 76 extending from the body portion 72 proximate the head portion 74 and a reset knob 78. Plunger device 70 is contained within a secondary housing 80 along with a spring 82 which is in a compressed state when the plunger device 70 is in the predeployment position shown in FIG. 4A. Referring now to FIG. 4C, which is a more detailed view of the injection actuator 60, the operation of device 50 will be described. As shown in FIG. 4C, actuator 60 includes a latch mechanism 84 including a latch 86 and a deployment lever 88. Latch 86 is spring biased such that protrusion 76 is in contact with latch 86, thereby preventing the plunger device 70 from deploying. Deployment lever 88 includes a first end 90 in contact with latch 86 and a second end 92 which is external to the housing 80. Deployment lever 94 further includes a pivot point 94 at which it is attached to the housing 80, the pivot point 94 enabling the first end 90 of the lever 88 to move in an opposite direction of the second end 92 of the lever 88 when a force is applied to the second end 92 of lever 88 in the direction of arrow 96. Such a force, when applied to the second end 92 of the lever 88 causes the first end 90 of the lever 88 to move in a direction opposite that shown by arrow 96, causing latch 86 to be driven away from the body portion 72 of the plunger device 70, thereby releasing protrusion 76. Once protrusion 76 is released, energy stored in spring 82 is released, causing plunger 70 to be driven in the direction shown by arrow 98.

Referring back to FIGS. 4A and 4B, prior to deployment, the injection actuator 60 is inserted into aperture 66 of housing 52 such that the cannula engagement portion 75 of plunger device 70 is in contact with the cannula 54 while the plunger device 70 is frictionally engaged with sidewalls 102, 104 of housing 52, thereby holding actuator 60 in place relative to the housing 52. Upon actuating the actuator 60 by applying the force to the second end 92 of lever 88, thereby releasing latch 86 from protrusion 76, a plunger device 70 applies a force in the direction of arrow 98 to the cannula 54, thereby driving the cannula through the exit port 64 into the skin of the patient, as shown in FIG. 4B. At this point, the actuator 60 may be removed from the housing 52 and the reset knob 78 may be pushed in a direction opposite that shown by arrow 98 causing the latch 86 to again engage protrusion 76 with the aid of ramp 106 of protrusion 76, which urges latch 86 away from protrusion 76 while the plunger device 70 is pushed back into the predeployment position shown in FIG. 4C.

Figure 4D:
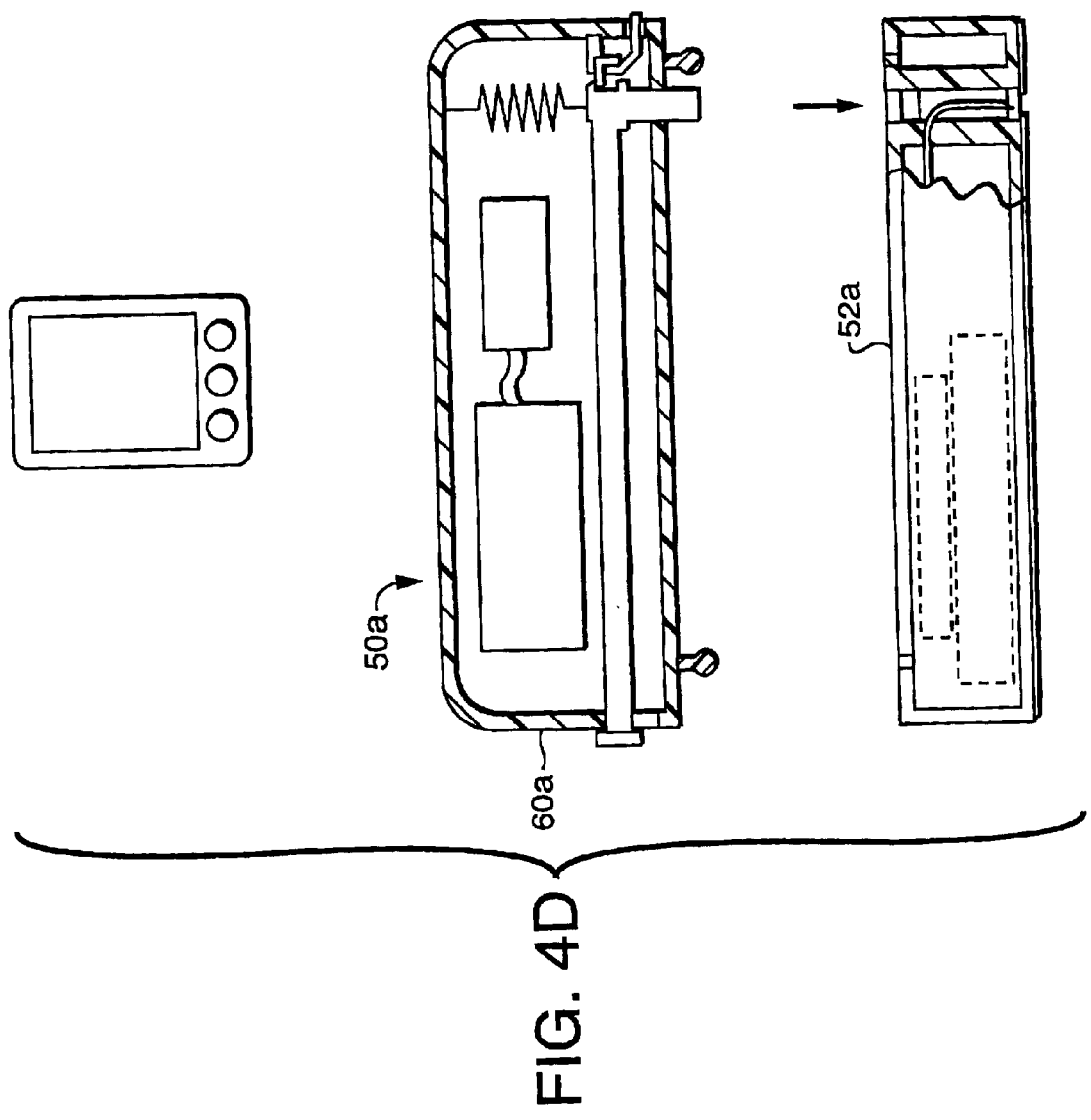
Figure 4C:
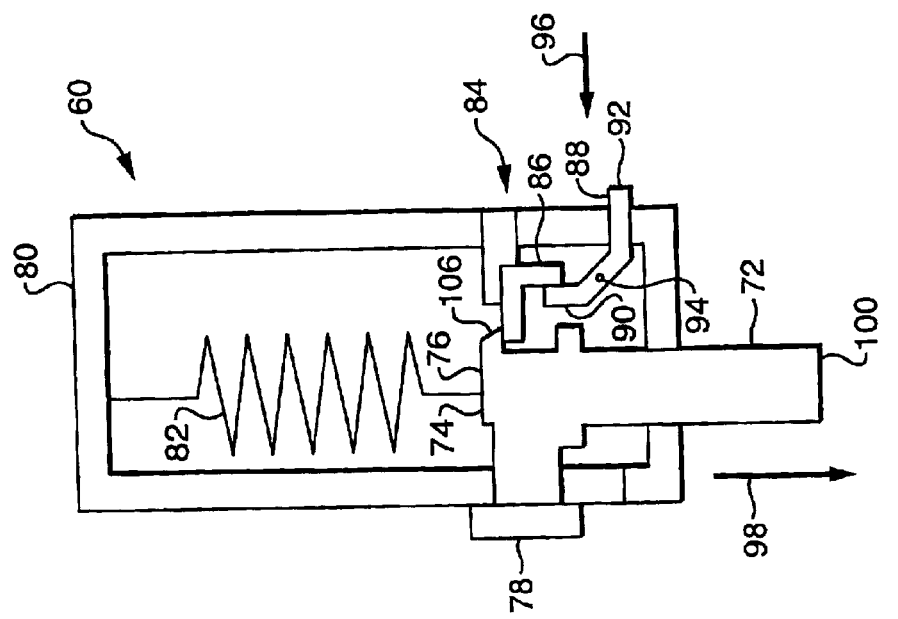
Figure 5A:
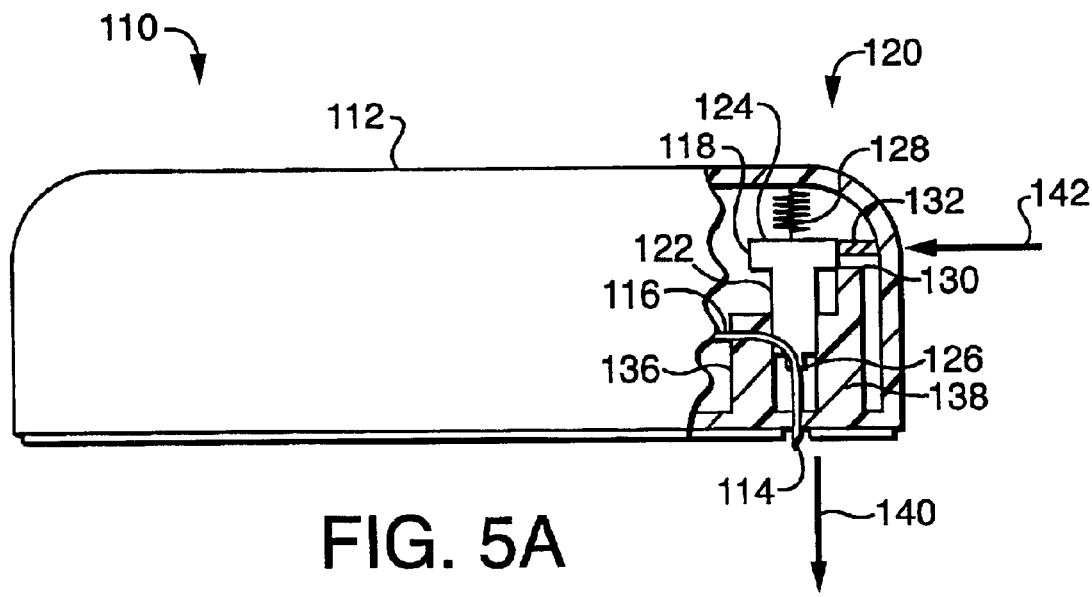
FIGS. 5A–5B are various views of another embodiment of a fluid delivery device in accordance with the present invention.
Figure 5B:
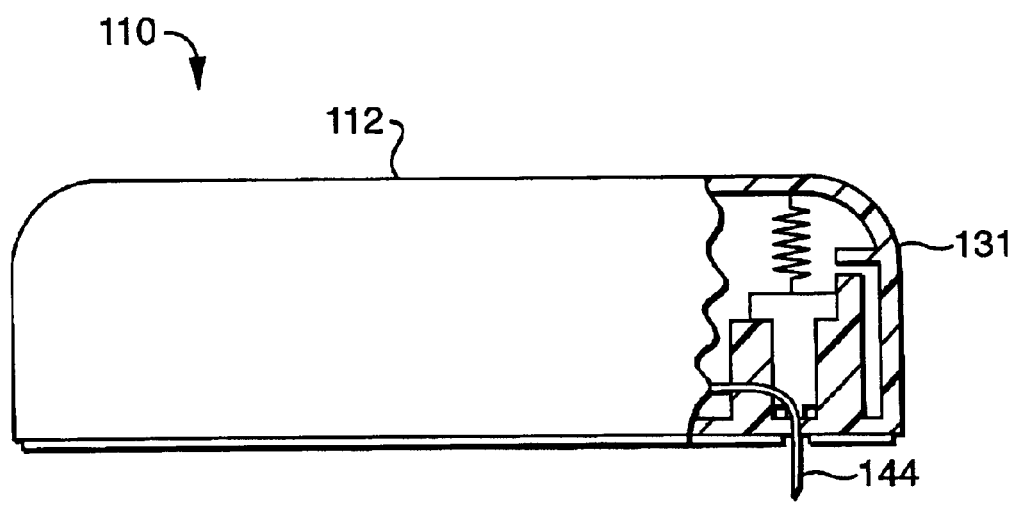

FIG. 4D shows an alternative embodiment 50a of the fluid delivery device 50, in which actuator 60a, includes, in addition to the elements described with reference to FIGS. 4A–4C, the fluid delivery device electronics and wireless receiver, which enables the primary housing 52a to have a smaller size and to enable the overall cost of fluid delivery device 50a to be greatly reduced. The actuator 60a is attached to the housing 52a for deployment of the cannula into the skin of the patient, and can be removed for use with another fluid delivery device. Other disposable and semi-reusable configurations of the multiple housings are disclosed in copending and commonly-owned U.S. Ser. No. 10/081,394, filed Feb. 22, 2002 and entitled MODULAR INFUSION DEVICE AND METHOD. Referring now to FIGS. 5A and 5B, a further embodiment 110 of the present invention will be described. Fluid delivering device 110 includes a housing 112 having an exit port 114 through which cannula 116 is driven upon actuation of plunger device 118, which is one part of injection actuator 120. Plunger device 118 includes a body portion 122 having a head portion 124 at a first end thereof and a cannula engagement portion 126 at a second end thereof, the cannula engagement portion 126 being frictionally engaged with cannula 116 when the actuator 120 is in the predeployment stage shown in FIG. 5A. Actuator 120 further includes a bias spring coupled between the head portion 124 of plunger device 118 and a wall of the housing 112 opposite the head portion 124. As shown in the figures, plunger device 118 is frictionally engaged between walls 136 and 138 of actuator 120. Wall 138 includes a protrusion 130 which engages head portion 124 of plunger device 118 so as to prevent plunger device 118 from being driven in the direction shown by arrow 140 under the force of spring 128. Actuator 120 further includes an urging device 132 extending inwardly from a wall of the housing 112 and in contact with the head portion 124 of plunger device 118.

In this embodiment, at least the wall portion 131 of housing 112 proximate urging device 132 is constructed of a deformable material, such that upon the application of a force to the wall portion 131 to which the urging device 132 is coupled, the force being in the direction shown by arrow 142, urging device 132 applies a similar force in the direction of arrow 142 to the head portion 124 of plunger device 118, thereby urging the head portion 124 away from the protrusion 130 and enabling spring 128 to deenergize, thereby driving the plunger device 118 and the cannula 116 in the direction shown by arrow 140, causing the penetrating member 144 to be driven into the skin of the patient as shown in FIG. 5B.

Figure 6:
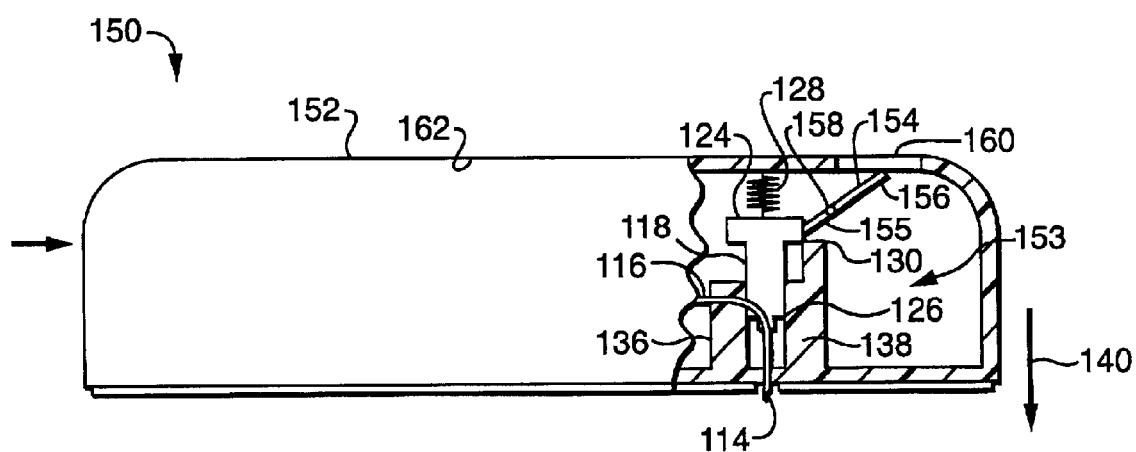
FIG. 6 is a cutaway view of another embodiment of a fluid delivery device in accordance with the present invention.

FIG. 6 shows a further embodiment 150 of the present invention. Fluid delivery device 150 includes a housing 152 and actuator 153, which is similar to the actuator 120 described with reference to FIGS. 5A and 5B. Accordingly, elements of actuator 153 which are the same as elements of actuator 120 will be described using the same reference numerals used in FIGS. 5A and 5B. As shown in FIG. 6, actuator 153 includes plunger device 118 including a head portion 124 and a cannula engagement portion 126. Plunger device 118 is frictionally engaged between walls 136 and 138, and wall 138 includes protrusion 130 which engages head portion 124 of plunger device 118 to prevent plunger device 118 from being driven in the direction shown by arrow 140 by biasing spring 128 which, as shown in FIG. 6, is in its compressed, energized state. Actuator 153 includes a lever 154 having a first end 155 in contact with the head portion 124 of plunger device 118 and a second end 156 which is in contact with a deformable portion 160 of wall 162 of housing 152. Lever 154 is pivotally attached to the housing 152 at a pivot point 158, such that when a force is applied to deformable portion 160 of housing 152 in the direction shown by arrow 140, first end 155 of lever 154 urges head portion 124 of plunger device 118 away from protrusion 130 of wall 138, thereby enabling biasing spring 128 to drive plunger device 118 in the direction of arrow 140, thereby driving the cannula 116 through exit port 114 and into the skin of the point.

Figure 7A:
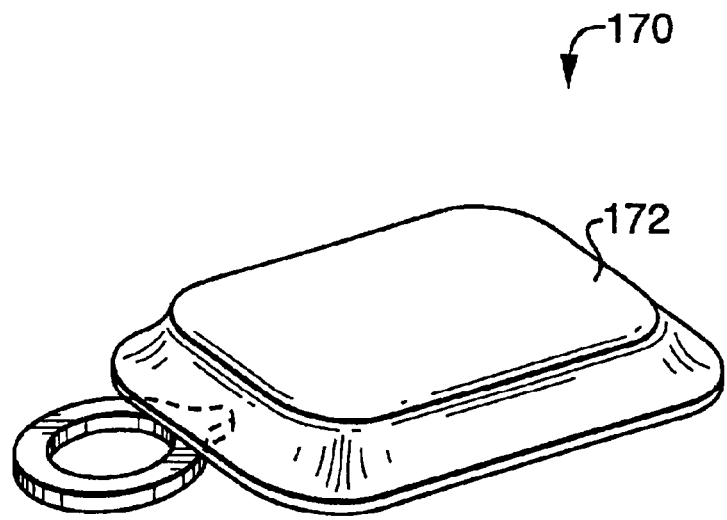
FIGS. 7A–7D are various views of another embodiment of a fluid delivery device in accordance with the present invention.
Figure 7B:
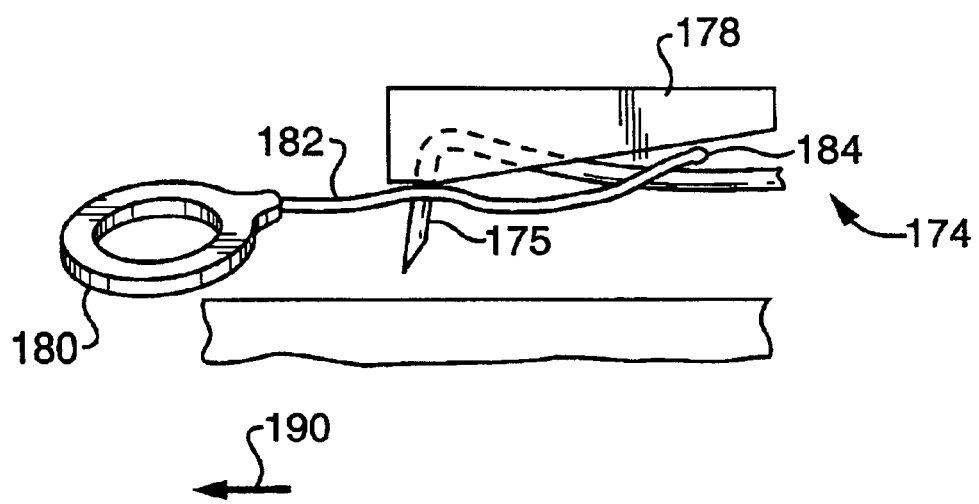
Figure 7C:
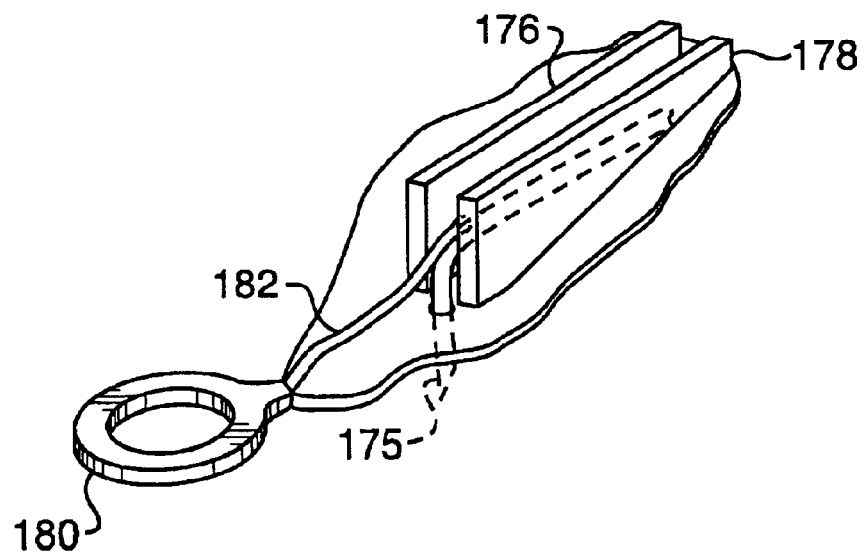
Figure 7D:
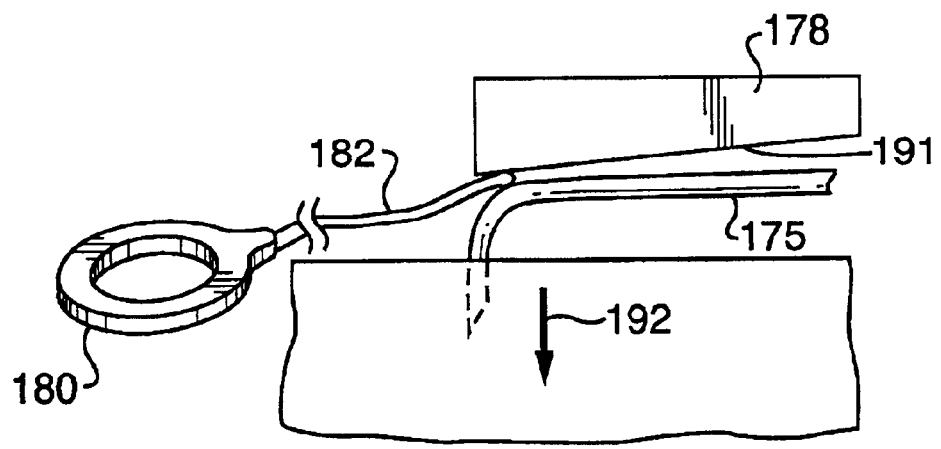

FIG. 7A shows another embodiment 170 of the present invention including a housing 172 and an injection actuator 174 shown in FIG. 7B. As shown in the figures, fluid delivery device 170 includes a cannula 175 which is disposed between two walls 176 and 178 of housing 172. Injection actuator 174 includes a pull tab 180 which is coupled to an urging device 184 by a connection element 182. Urging device 184 has a width which is wider than the distance between walls 176 and 178, thereby preventing urging device 184 from entering or becoming lodged between walls 176 and 178. When pull tab 180 is pulled in the direction of the arrow shown at 190, connection device 182 pulls urging device 184 along the outer ramped portion 191 of walls 176 and 178, causing the cannula 175, which initially rides between the walls 176 and 178, to be driven in the direction shown by arrow 192, FIG. 7D, through the exit port (not shown) and into the skin of the patient.

Figure 8A:
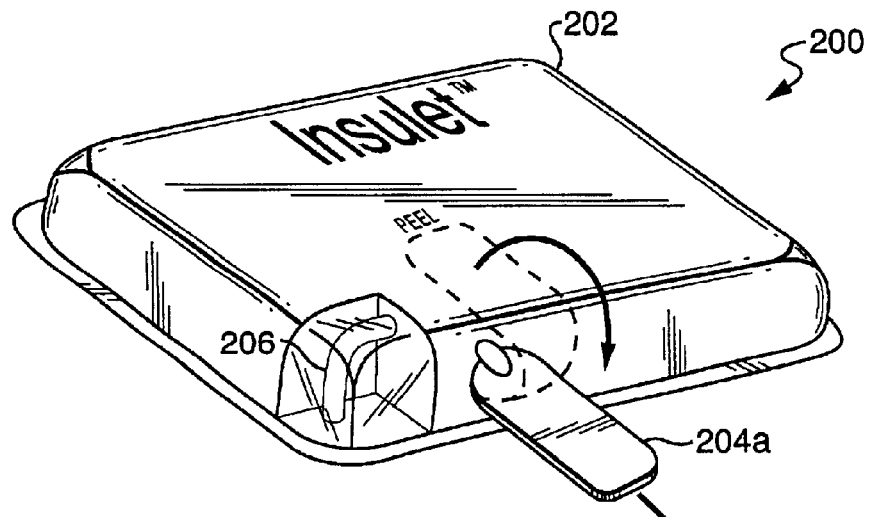
FIGS. 8A–8E are various views of another embodiment of a fluid delivery device in accordance with the present invention.
Figure 8B:
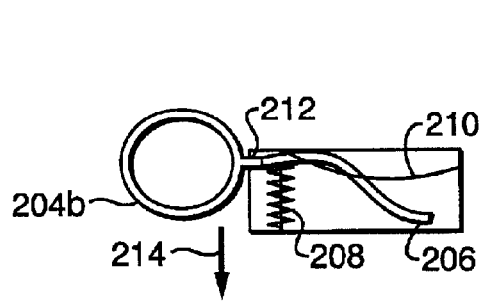
Figure 8C:
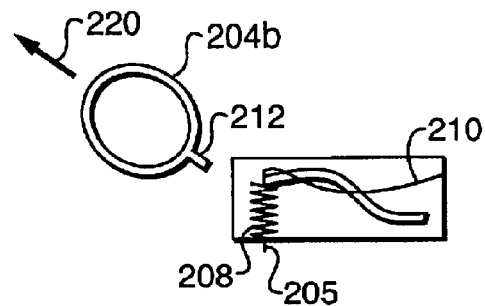
Figure 8D:
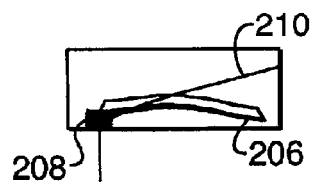
Figure 8E:
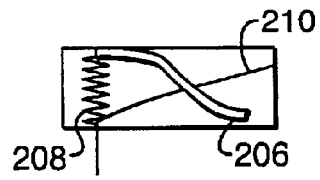

FIGS. 8A–8E show yet another embodiment 200 of the fluid delivery device in accordance with the present invention. Device 200 includes a housing 202 and a pull tab which is shown as a flat strip 204a in FIG. 8A and as a ring in 204b in FIG. 8B. It will be understood that any type of pull tab may be used in connection with the current invention in order to deploy the cannula as described herein. Device 200 further includes a cannula 206 having a distal end including a penetrating member for piercing the skin of the patient upon activation of the device 200, a coil compression spring 208, which biases the cannula 206 in the position shown in FIG. 8B and a leaf spring 210 which is affixed to the housing at a first end and which has a second end in contact with the cannula 206, the leaf spring 210 being biased to apply a force to the cannula 206 in the direction of arrow 214. Pull tab 204B includes an extension member 212 which, as shown in FIG. 8B in its initial state holds the leaf spring 210 in the position shown in FIG. 8B thereby maintaining cannula 206 in its first position shown under the bias force of spring 208. In order to activate the injection of the cannula into the skin of the patient, pull tab 204B is pulled in the direction indicated by arrow 220, causing extension member 212 to release leaf spring 210, causing the leaf spring to release its energy and drive the cannula in the direction of arrow 214 resulting in the penetrating member 205 of cannula 206 being driven into the skin of the patient. Leaf spring 210 has a biasing force which is greater than the biasing force of coil spring 208 such that leaf spring 210 is able to drive the cannula 206 in the direction of arrow 214 while compressing spring 208. As shown in FIG. 8D, when cannula 206 is fully inserted into the skin of the patient, coil spring 208 is fully compressed. At this point, leaf spring 210 reaches the end of its travel and, because the length of the leaf spring 210 is less than the distance between the first end of the leaf spring and the former connection point between the second end of the leaf spring and the, the leaf spring to loses contact with the cannula 206. The release of the cannula 206 by leaf spring 210 causes spring 208 to release its energy resulting in the cannula 206 being driven in a direction opposite arrow 214 back to the first position. This embodiment is useful in applications which will be described in further detail below in which a soft flexible cannula is disposed about the rigid cannula 206 such that when the rigid cannula 206 is forced back into its first position by coil spring 208, the flexible cannula remains within the skin of the patient.

Figure 9A:
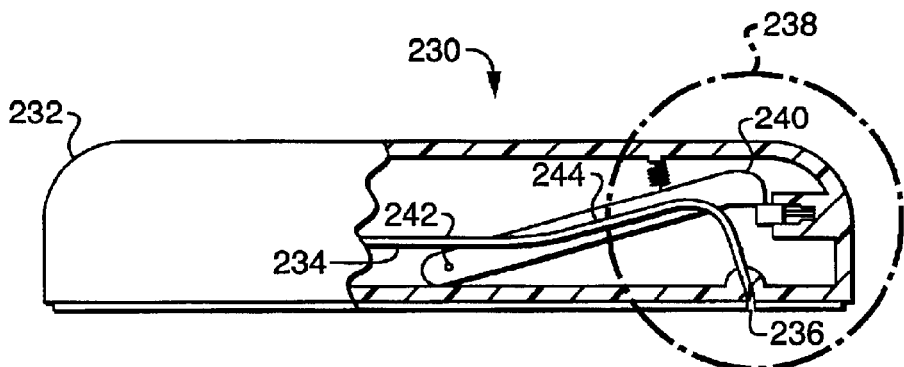
FIGS. 9A–9C are various views of another embodiment of a fluid delivery device in accordance with the present invention.
Figure 9B:
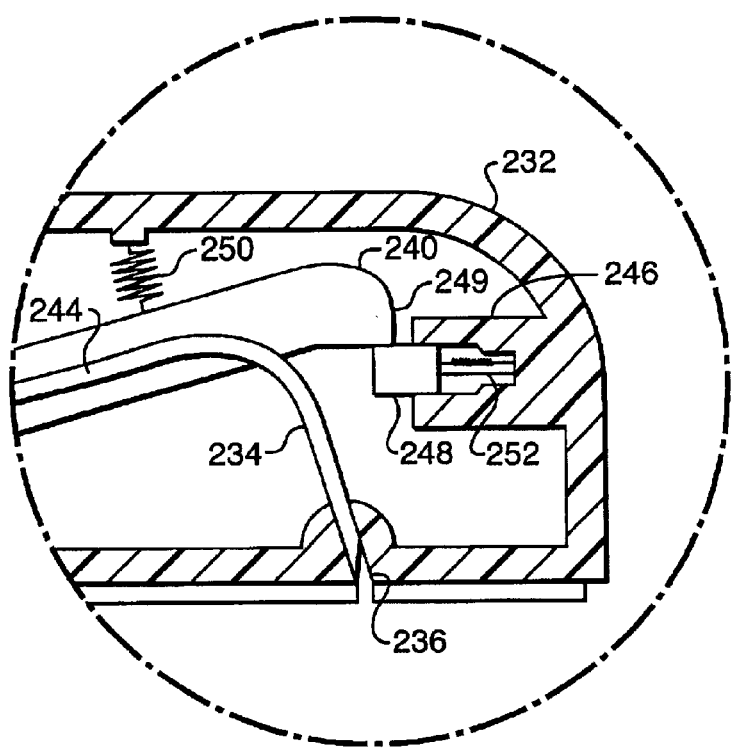
Figure 9C:
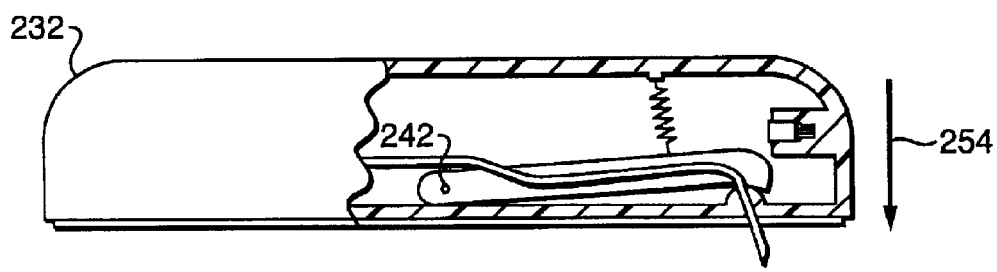

Referring now to FIGS. 9A–9C, a further embodiment 230 of the present invention will be described. Fluid delivery device 230 includes a housing 232 having an exit port 236. Cannula 234 is enclosed within the housing 232 in the first position shown in FIG. 9A and in the inset 238 shown in FIG. 9B. Fluid delivery device 230 further includes a rod 240 which is attached to the housing 232 at a pivot point 242 and which is attached to the cannula 234 along its length at 244. An injection actuation device includes a latch mechanism 246 having a latch 248 which contacts the end 249 of rod 240 for maintaining the rod 240 in the first position shown in FIG. 9A. A biasing spring is coupled between rod 240 and the housing 242. Biasing spring 250 is in a compressed, energized state when the rod 240 is in the first position, and thus forces the rod against latch 248. Latch mechanism 246 further includes an electrically driven latch actuator 252 which, upon the application of an electrical charge to the latch actuator 252, causes the latch 248 to be moved away from end 249 of rod 240, resulting in the rod 240 and cannula 234 being driven in the direction of arrow 254 under the biasing force of spring 250 to the second position shown in FIG. 9C. Latch actuator 252 receives the electrical charge based on common signals from the local processor, preferably initiated by instructions from the remote processor as described above. In the preferred embodiment, latch actuator 252 is a shape memory alloy or polymer which contracts under the influence of an electrical charge. However, other devices may be utilized for the latch actuator 252, such as a piezo electric actuator and a solenoid.

Figure 10:
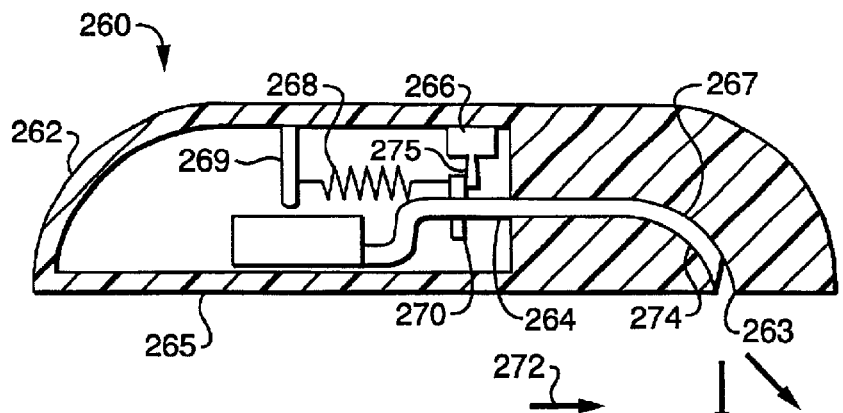
FIG. 10 is a cutaway view of another embodiment of a fluid delivery device in accordance with the present invention.

FIG. 10 shows another embodiment 262 of the present invention. Fluid delivery device 260 includes a housing 262, exit port 263 and cannula 264. In this embodiment, cannula 264 is constructed of a semi-rigid material which enables it to flex as it id driven from the housing 263. Housing 262 includes a cannula guide portion 267 which deflects the cannula 264 from the orientation shown with respect to the housing 262 by approximately 15 to 90 degrees as the cannula 264 passes through the exit port 263. As shown in FIG. 10, the main body portion of the cannula 264 is disposed substantially parallel to the first wall 265 of the housing 262. Device 260 further includes a latch assembly 266 including a latch 275 and a biasing spring 268 coupled between a first protrusion 269 of housing 262 and a flange 270 of cannula 264. In the predeployment state shown in FIG. 10, biasing spring 268 is in a compressed, energized state, which maintains the flange 270 of cannula 264 in contact with the latch 275. Latch assembly 266 may include a manual activation device, such as described with reference to FIG. 4A, or an electrical activation device, such as described with reference to FIG. 9A. In either case, upon activation of the latch mechanism 266, latch 275 is moved out of contact with the flange 270, causing biasing spring 268 to release its energy and drive cannula 264 through exit port 263 and into the skin of the patient. As the biasing spring 268 is deenergized, the main body portion of the cannula 264 travels in the direction indicated by arrow 272, while distal end 274 of the cannula is directed toward first wall 265 by cannula guide portion 267 of housing 262. As set forth above, cannula guide portion 267 translates the substantially parallel (to first wall 265) motion of cannula 264 to a direction approximately 15 to 90 degrees relative to the parallel motion to cause the distal end 274 of cannula 264 to be directed out of the housing 262 through exit port 263. While the cannula guide portion 267 of FIG. 10, is shown as a curved channel for deflecting the cannula while guiding it out of the housing 260, it will be understood that it could be in the form of one or more angled planar deflecting surfaces or any suitable combination of guiding components. Furthermore, while, in the preferred embodiment, the cannula may be deflected 15 to 90 degrees relative to the initial parallel motion, it will be understood that the cannula guide portion of the fluid delivery device may be constructed to deflect the cannula to an angle less than 15 degrees or more than 90 degrees relative to the initial parallel motion. In many applications of the fluid delivery device of the present invention, it is preferred to deliver the fluid from the device to the patient via a flexible cannula which is inserted into the skin of the patient. The flexible cannula is more comfortable when maintained in the skin of the patient than a rigid needle, particularly in the case of an active patient whose movements may cause discomfort or pain with a rigid cannula in place in the patient's skin. However, because the flexible cannula cannot be injected into the skin by itself, the flexible cannula is mated with a rigid cannula to facilitate the injection of the flexible cannula into the skin of the patient.

The following fluid delivery devices include both a rigid or semi rigid cannula having a sharpened penetrating member coupled with a flexible cannula, which may be constructed from medical grade silicon, PVC or other suitable materials. In these embodiments, the rigid cannula is disposed within the lumen of the flexible cannula. The rigid cannula may be hollow, for delivering the fluid therethrough, or it may be solid, wherein the fluid is delivered around the rigid cannula through the lumen of the flexible cannula.

In these embodiments, the penetrating member of the rigid cannula is first driven into the skin of the patient and the flexible cannula follows the rigid cannula into the skin after the skin has been punctured by the penetrating member. The penetrating member of the rigid cannula is then retracted into the flexible cannula so that the flexible cannula acts as a cushion between the patient and the penetrating member. The penetrating member may be retracted to its original position within the housing, to a position between its original position and its deployed position, or to a position further away from its deployed position than its original position. The position of the rigid cannula between the original position and the deployed position is preferred because the rigid cannula helps to prevent any kinking that may occur in the flexible cannula between the housing and the patient's skin.

Figure 11A:
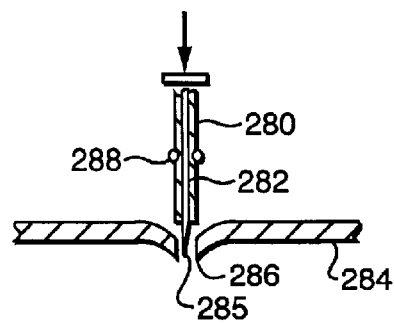
FIGS. 11A–11C are various views of another embodiment of a fluid delivery device in accordance with the present invention.
Figure 11B:
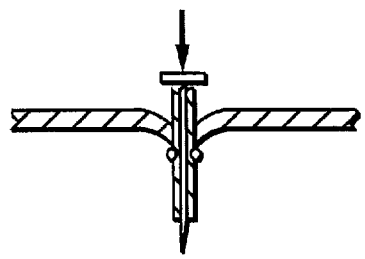
Figure 11C:
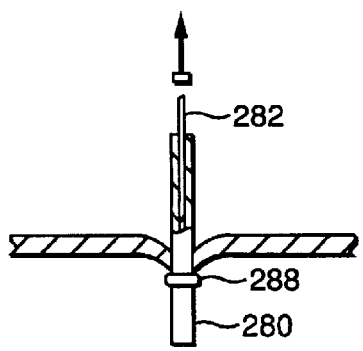

In order to insure that then flexible cannula does not retract along with the rigid cannula, a retention device may be built into either the flexible cannula or the exit port to retain the flexible cannula in its fully deployed position when the rigid cannula is retracted. An example of an embodiment wherein the flexible cannula includes a retention device is shown in FIGS. 11A–11C. In these figures, only the relevant portions of the fluid delivery device pertaining to the retention device are shown.

FIG. 11A shows a flexible cannula 280 and a rigid cannula 282 disposed within the lumen of the flexible cannula 280. As shown in FIG. 11A, penetrating member 285 is disposed proximate exit port 286 of first wall 284. As shown, exit port 286 is tapered outwardly of the fluid delivery device. In this embodiment, flexible cannula 280 includes retention device 288, which, in this embodiment, is in the form of an annular ring. When the rigid cannula 282 and the flexible cannula 280 are driven through the exit port 286, the retention member 288 is also driven through the exit port 286. As can be seen in the figures, retention device 288 causes the flexible cannula 280 to have a width which is greater than the width of the exit port 286. When the rigid cannula 282 is retracted in the direction indicated by arrow 290, FIG. 11C, the flexible cannula 280 is prevented from retracting with the rigid cannula 282 because the retention device 288 comes into contact with the exit port 286, causing the flexible cannula to be retained in the deployed position shown in FIG. 11C. As set forth above, the rigid cannula 282 may be retracted back to its original predeployment position, as shown in FIG. 11C. Alternatively, it may be retracted to a position between the deployed position and the predeployment position or to a position further away from the deployed position than the predeployment position.

Alternatively, the retention device may include one or more barbs located on the flexible cannula, one or more barbs located directly within the exit port or one or more barbs located on both the flexible cannula and the exit port.

Figure 12A:
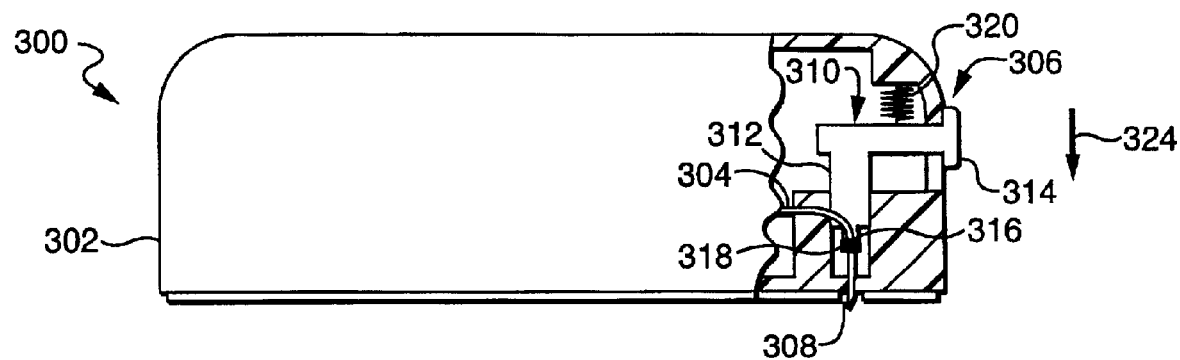
FIGS. 12A–12B are various views of another embodiment of a fluid delivery device in accordance with the present invention.
Figure 12B:
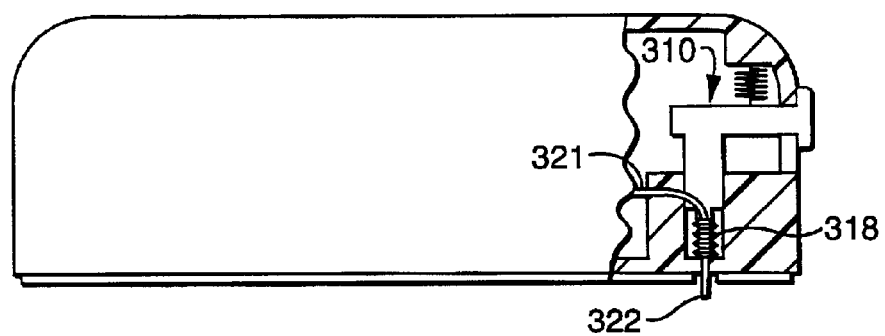

FIGS. 12A and 12B show a further embodiment 300 of the present invention. Fluid delivery device 300 includes a housing 302, cannula assembly 304, injection actuator 306 and exit port 308. Injection actuator 306 includes a plunger device 310 having a body portion 312, a deployment knob 314 and a cannula engagement portion 316. A biasing spring 320 is coupled between the body portion 312 and the housing 302. In the predeployment stage shown in FIG. 12A, the biasing spring is in an unenergized state. Although not explicitly shown in FIG. 12A, cannula assembly 304 includes a rigid cannula disposed within the lumen of flexible cannula 321. Flexible cannula 321 includes a bellows portion 318 which enables the distal end 322 of the flexible cannula to extend from the housing independent of the rest of the flexible cannula 321. In the predeployment stage shown in FIG. 12A, the bellows portion is compressed and the distal end 322 of flexible cannula 321 is within the housing 302.

Deployment of the flexible cannula into the patient's skin takes place as follows. After the housing is attached to the patient, the patient or other person pushes knob 314 of injection actuator 306 in the direction indicated by arrow 324. This causes the cannula assembly 304 to be driven into the skin of the patient through exit port 308, as described above with reference to FIGS. 11A–11C. Once the plunger device 310 has reached the end of its travel and both the rigid cannula and the flexible cannula 321 have been injected into the skin of the person, biasing spring 320 is extended and energized such that when the knob 314 is released, biasing spring 320 deenergizes, causing the cannula assembly 304 to be retracted into the housing 302. However, because of the retention device disposed either on the flexible cannula or within the exit port 308, the distal end 322 of the flexible cannula 321 is retained in the deployed position shown in FIG. 12B and the bellows portion 318 is fully expanded, which enables the rigid cannula to be retracted without also retracting the distal end 322 of the flexible cannula 321. Depending on the particular design of the fluid delivery device, in the deployed position, the rigid cannula may be retracted to position that is the same as its predeployment position, to a position that is between the predeployment position and the deployment position, or to a position that is further away from the deployment position than the predeployment position.

Figure 13A:
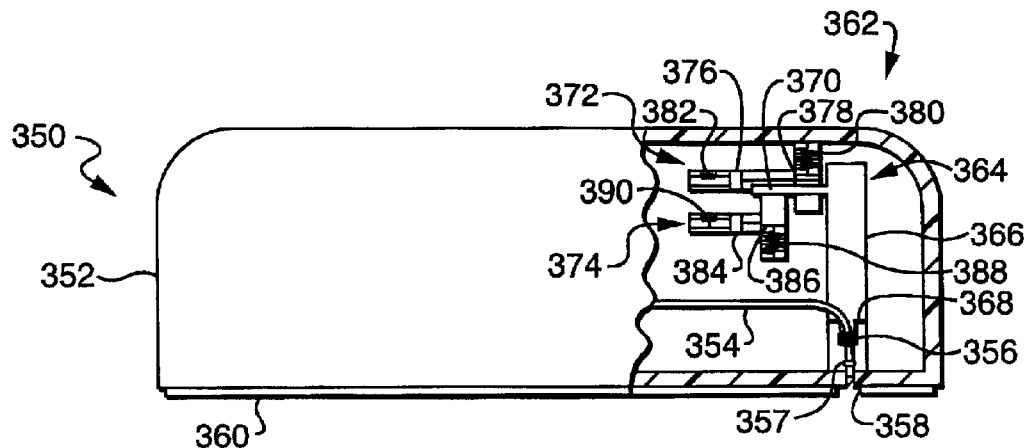
FIGS. 13A–13C are various views of another embodiment of a fluid delivery device in accordance with the present invention.
Figure 13B:
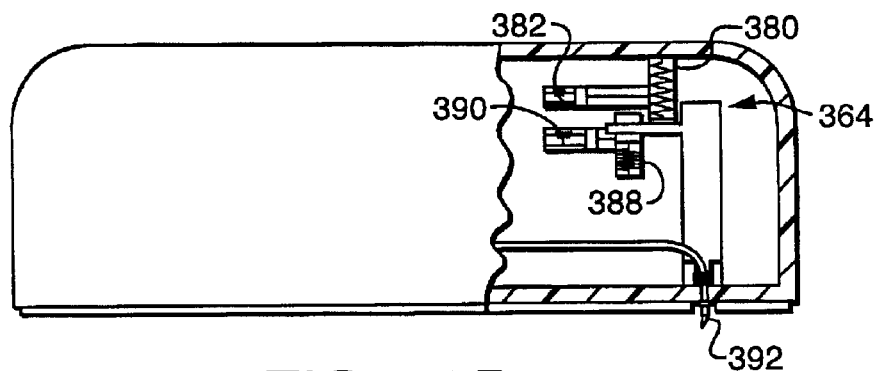
Figure 13C:
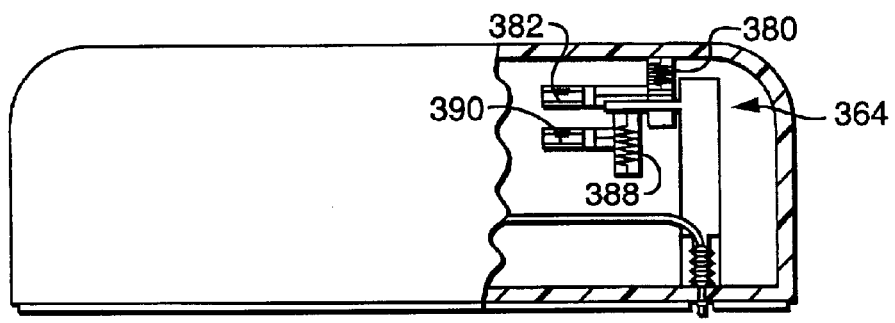

FIGS. 13A–13C show a further embodiment 350 of the present invention. Fluid delivery device 350 includes a housing 352 having an exit port 358 in first wall 360, a cannula assembly including a flexible cannula 354 having a bellow portion 356 and retention device 357 and a rigid cannula (not visible) disposed within the lumen of the flexible cannula 354 and an injection actuator 362. Injection actuator 362 includes a plunger device 364 including a body portion 366, a cannula engagement portion 368 and a lateral protrusion 370. Injection actuator 362 further includes deployment latch mechanism 372 and retraction latch mechanism 374. Retraction latch mechanism 372 includes a latch 376 for maintaining a deployment member 378 in a predeployment position against the bias force of deployment spring 380. Deployment latch mechanism 372 further includes an activation device 382, which is preferably in the form of a shape memory alloy or polymer, as described above. Retraction latch mechanism 374 includes a latch 384 for maintaining a retraction member 384 in a predeployment position against the bias force of retraction spring 388. Retraction latch mechanism 374 further includes an activation device 390, which is preferably in the form of a shape memory alloy or polymer.

As shown in FIG. 13B, upon the application of a charge to activation device 382, latch 376 is pulled out of contact with deployment member 378, causing deployment spring 380 to release its energy as it pushes deployment member 378 against lateral protrusion 370, thereby forcing plunger device 364 into the deployment position. In the deployment position, shown in FIG. 13B, both the flexible cannula 354 and the rigid cannula, including penetrating member 392, are injected into the skin of the person. In this position, retention device 357 is either driven beyond the exit port 358 or is lodged within exit port 258.

Shortly after the cannula reaches the deployment position shown in FIG. 13B, a charge is applied to activation device 382 of retraction latch mechanism 374 and latch 384 is pulled out of contact with retraction member 384, causing retraction spring 388 to release its energy as it pushes deployment member 378 against lateral protrusion 370, thereby forcing plunger device 364 from the deployment position to the post-deployment position shown in FIG. 13C. Retention device 357 maintains the flexible cannula 354 in the deployment position, such that, in the post-deployment position, shown in FIG. 13C, the bellows portion 356 of the flexible cannula 354 is extended and the rigid cannula is retracted to its predeployment position.

As is shown in FIG. 13C, bellows portion 356, by expanding, enables the rigid cannula to be retracted while allowing the flexible cannula to remain in place. Accordingly, in alternative embodiments, bellows portion 356 may be replaced by any type of construction that will enable the rigid penetrator to be retracted without jeopardizing the position of the flexible cannula in the post-deployment position. One example of such a construction is a sliding joint between the outside diameter of the rigid cannula and the inside diameter of the flexible cannula. Other constructions will be apparent to those skilled in the art.

FIGS. 14A–14D show an embodiment 400 which is similar to the device 350 of FIGS. 13A–13C, but in which the retraction latch mechanism is activated automatically and therefore does not require the second activation device. Accordingly, elements of this embodiment which are the same as the fluid delivery device 350 of FIGS. 13A–13C, are referenced with the same reference numerals used in connection with the description of fluid delivery device 350. Fluid delivery device 400 includes a housing 352 having an exit port 358 in first wall 360, a cannula assembly including a flexible cannula 354 having a bellows portion 356 and retention device 357 and a rigid cannula (not visible) disposed within the lumen of the flexible cannula 354 and an injection actuator 362. Injection actuator 362 includes a plunger device 364 including a body portion 366, a cannula engagement portion 368 and a lateral protrusion 370. Injection actuator 362 further includes deployment latch mechanism 372 and retraction latch metabolism 402. Retraction latch mechanism 372 includes a latch 376 for maintaining a deployment member 378 in a predeployment position against the bias force of deployment spring 380. Deployment latch mechanism 372 further includes an activation device 382, which is preferably in the form of a shape memory allow or polymer, as described above. Retraction latch mechanism 402 includes a latch 404 for maintaining a retraction member 406 in a predeployment position against the bias force of retraction spring 408. Retraction latch mechanism 402 further includes a latch spring 410, for biasing latch 404 in the position shown in FIG. 14A, wherein latch 404 contacts retraction member 406.

Figure 14A:
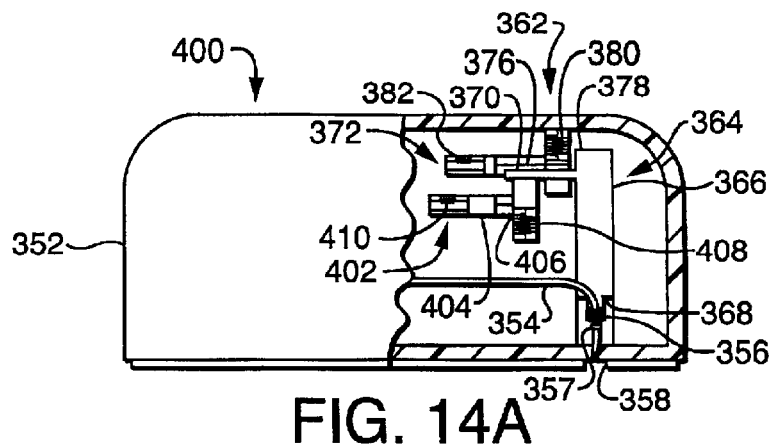
FIGS. 14A–14D are various views of another embodiment of a fluid delivery device in accordance with the present invention.
Figure 14B:
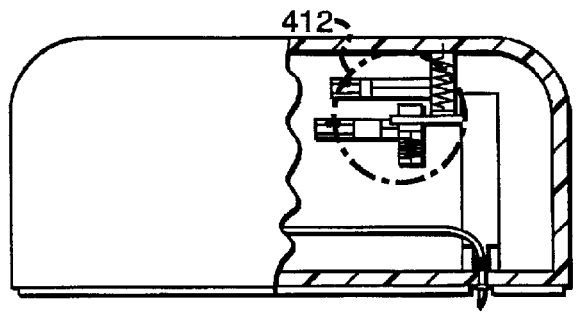

As shown in FIG. 14B, upon the application of a charge to activation device 382, latch 376 is pulled out of contact with deployment member 378, causing development spring 380 to release its energy as it pushes deployment member 378 against lateral protrusion 370, thereby forcing plunger device 364 into the deployment position. In the deployment position, shown in FIG. 13B, both the flexible cannula 354 and the rigid cannula, including penetrating member 392, are injected into the skin of the person. In this position, retention device 357 is either driven beyond the exit port 358 or is lodged within exit port 258.

Figure 14C:
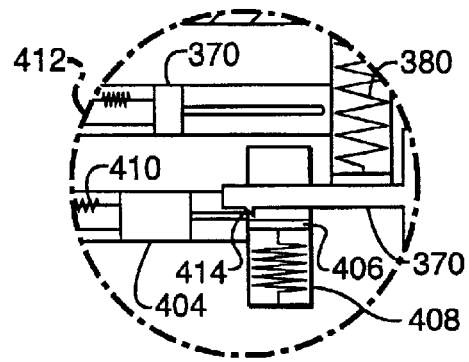
Figure 14D:
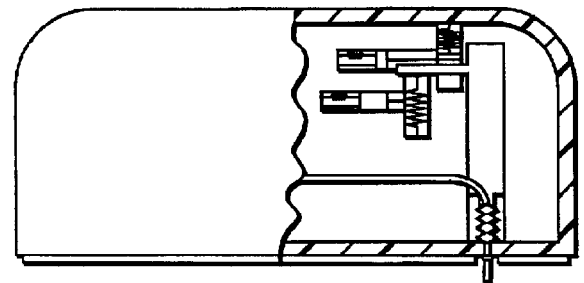

FIG. 14C shows detailed portion 412 of FIG. 14B. As shown in FIG. 14C, lateral protrusion 370 of plunger device 364 includes a ramp portion 414 positioned thereon such that, when the plunger device 364 reaches the deployment position shown in FIG. 14B, ramp portion 414 urges latch 404 out of contact with retraction member 406, thereby enabling retraction spring 4081380 to deenergize and retract the plunger device to the post-deployment position shown in FIG. 14D. Retention device 357 maintains the flexible cannula 354 in the deployment position, such that, in the post-deployment position, shown in FIG. 14D, the bellows portion 356 of the flexible cannula 354 is extended and the rigid cannula is retracted to its predeployment position.

Again, alternative constructions of the bellows portion that will enable the rigid penetrator to be retracted without jeopardizing the position of the flexible cannula in the post-deployment position, such as the sliding point joint, may be utilized in these embodiments. Other constructions will be apparent to those skilled in the art.

Figure 15:
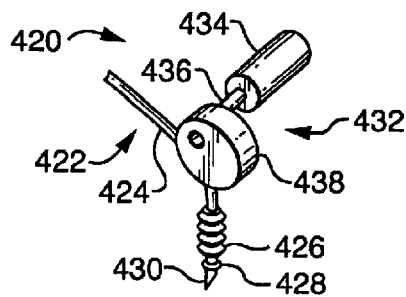
FIG. 15 is a perspective view of another embodiment of a fluid delivery device in accordance with the present invention.

FIG. 15 shows yet another embodiment 420 of the present invention. In convention with this embodiment, and the several embodiments that follow, only the injection actuator and cannula assembly are shown and described. It will be understood that the injection actuator and cannula assembly described in connection with these embodiments will be housed in a housing similar to those previously described. Cannula assembly 422 includes a flexible cannula 424 having a bellows portion 426 and a retention device 428. A rigid cannula having a penetrating member 430 is disposed within the lumen of the flexible cannula 424. Injection actuator 432 includes a driving mechanism 434 for driving axle 436 which is coupled to urging devices 438. Driving mechanism 434 may comprise a motor, spring or any device that is capable of causing axle 436 to rotate at least one revolution. In this embodiment, urging device 438 is in the form of a disk and axle 436 is coupled thereto at a point offset from the center of the disk. When the driving mechanism 434 is activated and causes the axle 436 to rotate, the portion of urging device 438 opposite the axle 436 pushes the cannula assembly 422 to the deployment position described above. In the preferred embodiment, the cannula assembly 422 is biased in the predeployment position shown in FIG. 15 such that, after the urging device pushes the cannula assembly 422 into the deployment position and continues to rotate, the cannula assembly returns to the predeployment position under the force of the biasing means coupled to the assembly. As described above, the bellows portion 426 and retention device 428 enable the flexible cannula 422 to remain in the deployed position while the rigid cannula and penetrating member 430 are retracted.

Figure 16:
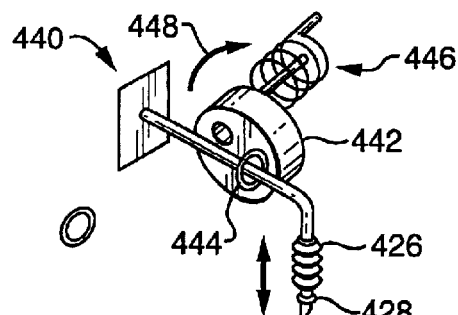
FIG. 16 is a perspective view of another embodiment of a fluid delivery device in accordance with the present invention.

FIG. 16 shows an embodiment 440 which is similar to the device 420 of FIG. 15. However, urging member 442 includes a retention device 444 for retaining the cannula assembly in contact with the urging device 442. Rather than rotating the axle a complete revolution, driving mechanism 446, which may be a prewound spring, as shown, a bidirectional motor, or other driving means, rotates the urging member one quarter turn in the direction indicated by arrow 448, to drive the cannula assembly to the deployment position, and one quarter turn in the direction opposite that indicated by arrow 448, to retract the cannula assembly to the post-deployment position. As described above, the bellows portion 426 and retention device 428 enable the flexible cannula 422 to remain in the deployed position while the rigid cannula and penetrating member 430 are retracted.

Figure 17A:
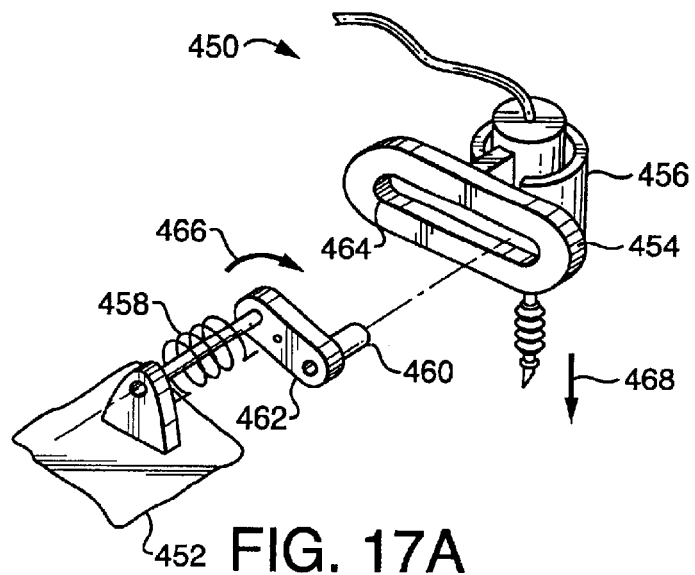
FIGS. 17A–17B are various views of another embodiment of a fluid delivery device in accordance with the present invention.
Figure 17B:
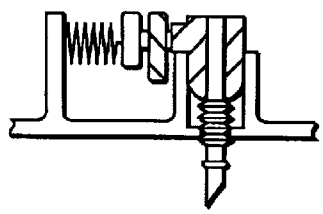

FIGS. 17A and 17B show an embodiment 450 which includes a driving mechanism 452 which is coupled to a force translator 454 which in turn is coupled to cannula assembly 456. In the preferred embodiment, driving mechanism 452 includes a torsion spring which is energized before protrusion 460 of lever arm 462 is inserted into slot 464 of force translator 454. FIG. 17B is a side view of embodiment 450 in such a configuration. When the torsion spring 458 is released, it lever arm 462 and protrusion 460 to rotate in the direction indicated by arrow 466, causing protrusion 460 to drive the force translator 454 and cannula assembly 456 in the direction indicated by arrow 468 during the first 45 degrees of rotation, thereby injecting the rigid cannula and flexible cannula into the skin of the person, and then to drive the force translator 454 and cannula assembly 456 in the direction opposite that indicated by arrow 468 during the second 45 degrees of rotation, thereby retracting the rigid cannula. The flexible cannula maintains its deployment position with the aid of the bellows portion and the retention device.

Figure 18A:
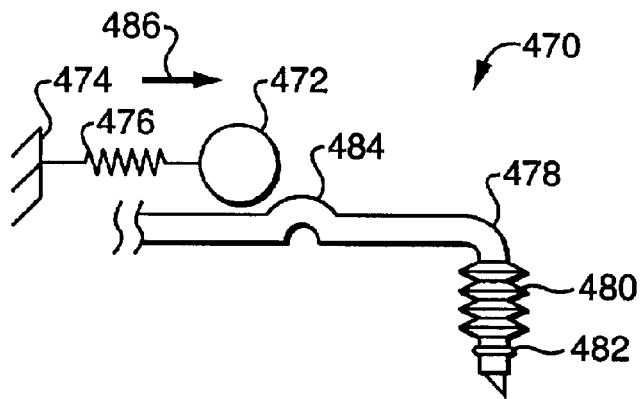
FIGS. 18A–18C are various views of another embodiment of a fluid delivery device in accordance with the present invention.
Figure 18B:
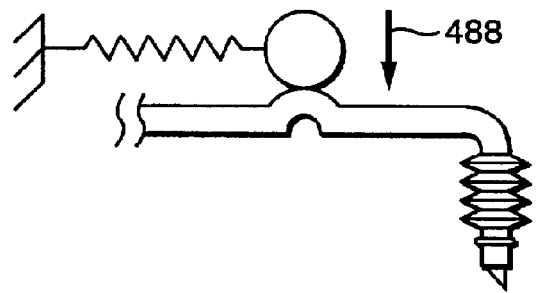
Figure 18C:
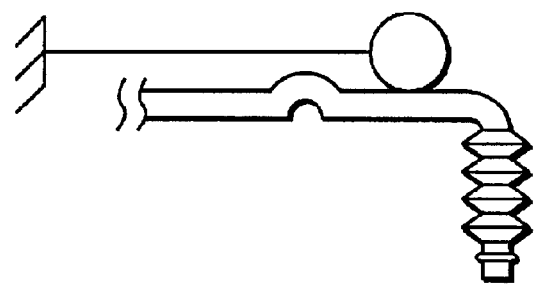

FIG. 18 shows another embodiment 470 of the invention including an urging device 472 which is coupled to a portion 474 of the housing of the associated fluid delivery device by a spring 476. Cannula assembly 478 includes a flexible cannula having a bellows portion 480 and preferably a retention device 482. A rigid cannula is disposed within the lumen of the flexible cannula. Cannula assembly 478 includes a protrusion 484, which may comprise a bend in the rigid and flexible cannulas, as shown in the figure, or a ramp portion mounted on that cannula assembly. In the predeployment position shown in FIG. 18A, the spring 476 is maintained in an energized state by a latch assembly (not shown) such that the urging device 472 is positioned one side of the protrusion 472. Upon deenergization of the spring 476, the urging device 472 is driven in the direction indicated by arrow 486. Urging member 472 is constructed and mounted within the housing such that it is maintained in its plane of travel as the spring 476 is deenergized. Upon contacting protrusion 484, urging device 472 exerts a force thereon, causing cannula assembly 478 to be driven in the direction indicated by arrow 488 from the predeployment position to the deployed position. As the urging member 472 passes over the protrusion 484, the cannula assembly, which is biased in the predeployment position, travels in the direction opposite that indicated by arrow 488 from the deployed position to the predeployment position, as shown in FIG. 18C. The flexible cannula maintains its deployment position with the aid of the bellows portion and the retention device.

In further embodiments of the invention, in order to enable the flexible cannula to remain in the deployed position while retracting the rigid cannula, the end of the flexible cannula opposite the end that is injected into the person is constructed of a sealing portion which forms a fluid seal with the rigid cannula that allows the flexible cannula to move within the flexible cannula while maintaining the fluid integrity of the fluid delivery device and while enabling the retention device to hold the flexible cannula in the deployed position.

Figure 19:
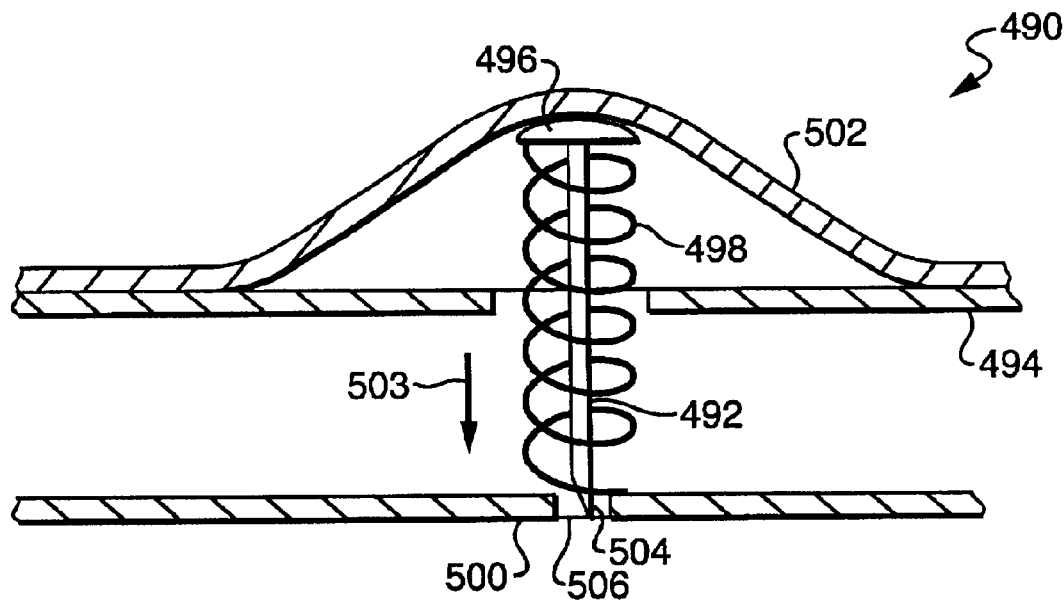
FIG. 19 is a cutaway view of another embodiment of a fluid delivery device in accordance with the present invention.
Figure 20:
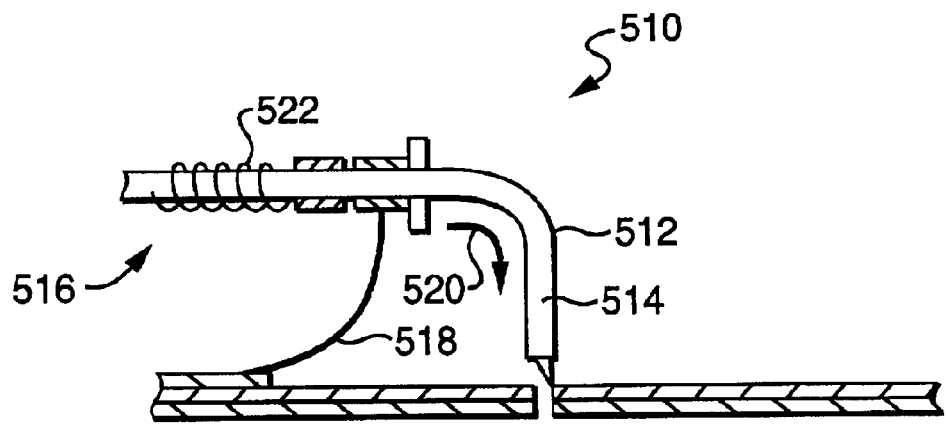
FIG. 20 is a perspective view of another embodiment of a fluid delivery device in accordance with the present invention.

FIGS. 19 and 20 show two embodiments that utilize this type of cannula assembly. Embodiment 490 of FIG. 19 includes a cannula assembly 492 having a rigid cannula within a flexible cannula. Both are mounted within a housing 494 of a fluid delivery device. The rigid cannula includes a head portion 496 which extends from the housing 494. A return spring is mounted between the head portion 496 of the rigid cannula and the wall 500 of housing 494 to bias the cannula assembly in the position shown in figure, which is the predeployment position. An optional membrane 502 may be mounted over the cannula assembly to protect the integrity of the housing 494. In operation, the head portion of the cannula assembly is pushed in the direction indicated by arrow 503 to cause the flexible cannula and the penetrating member 504 of the rigid cannula to be driven out of exit port 506 and into the skin of the person. When the head portion 496 is released, spring 492 is deenergized, causing the rigid cannula to be driven in the direction opposite that indicated by arrow 503. However, the flexible cannula, with the aid of a retention device mounted thereon or on the exit port, is held in place in the deployed position while the rigid cannula is retracted.

FIG. 20 shows an embodiment 512 having a cannula assembly 514 disposed within a cannula guide 512. Injection actuator 516 includes a deployment spring 518 for driving the cannula assembly 514 through guide 512 in the direction indicated by arrow 520 and a retraction spring 522, which is coupled between the housing (not shown) and the rigid cannula. When deployment spring 518 reaches the end of its travel, it loses contact with the cannula assembly 514 and retraction spring 522, which is now energized, deenergizes, causing the rigid cannula to be pulled in the direction opposite that indicated by arrow 520. A retention device associated with the fluid delivery device maintains the flexible cannula in the deployed position while the rigid cannula is retracted.

Figure 21D:
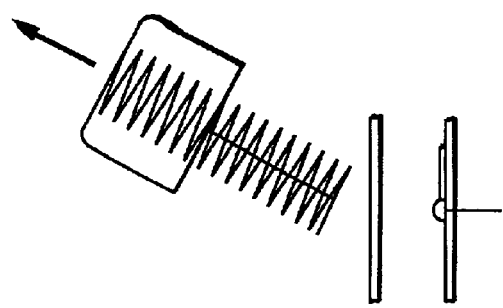
FIGS. 21A–21D are various views of another embodiment of a fluid delivery device in accordance with the present invention.
Figure 21C:
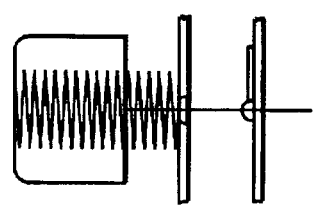
Figure 21B:
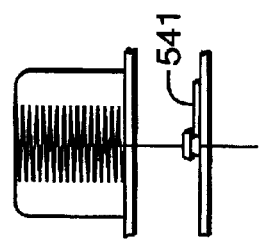
Figure 21A:
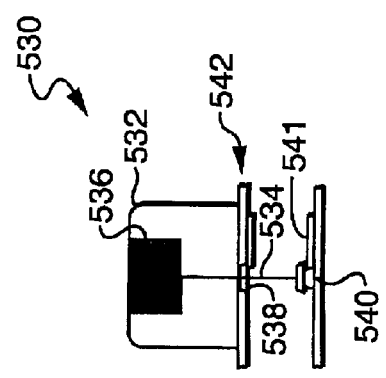

FIGS. 21A–21D show an embodiment 530 including a secondary housing 532 including a cannula assembly 534 and a deployment spring 536. In the predeployment position, spring 536 is compressed and energized, and held in this state by a latch mechanism (not shown). The flexible cannula 541 of the cannula assembly is housed within the housing 542 and the rigid cannula is inserted into the housing 542 and into flexible cannula 541 through a port 538 such that the penetrating member of the rigid cannula and the distal end of the flexible cannula are proximate exit port 540. Upon releasing the latch mechanism, deployment spring 536 deenergizes and drives the cannula assembly, including the flexible cannula 541, through the exit port 540 and into the skin of the person. This deployment position is shown in FIG. 21B. The secondary housing can then be removed from the housing 542 and discarded, FIGS. 21C and 21D, or reloaded for the next use.

Figure 22A:
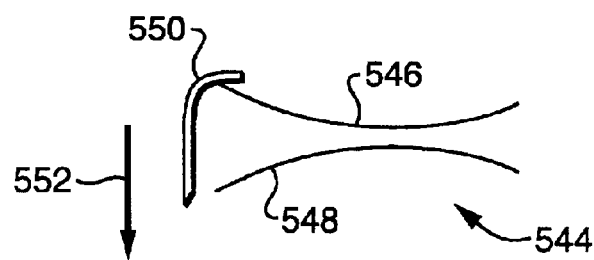
FIGS. 22A–22C are various views of another embodiment of a fluid delivery device in accordance with the present invention.
Figure 22B:
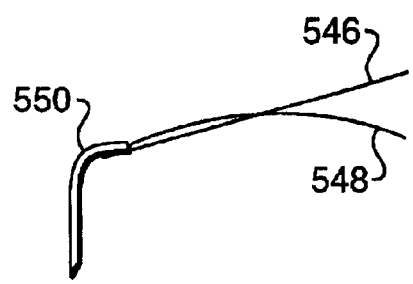
Figure 22C:
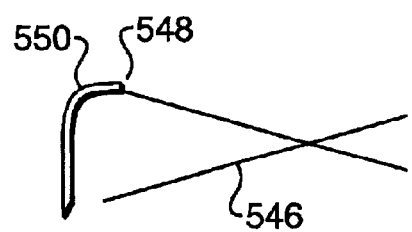

FIGS. 22A–22C shown yet another embodiment 544 of the injection actuator. This embodiment 544 includes a deployment spring 546 coupled between the cannula assembly 550 and the housing (not shown) and a retraction spring 548 in a preloaded state, FIG. 22A. When the deployment spring 546 is released, it drives the cannula assembly in the direction indicated by arrow 552 into the skin of the person. At the end of the travel of the deployment spring 546, cannula assembly 550 comes into contact with retraction spring 548 while deployment spring 546 loses contact with the cannula assembly 550, FIG. 22B. Retraction spring 548 is then activated, thereby driving cannula assembly 550 in the direction opposite the indicated by arrow 552 to retract the rigid cannula, FIG. 22C, while the flexible cannula remains in the deployed position.

Figure 23A:
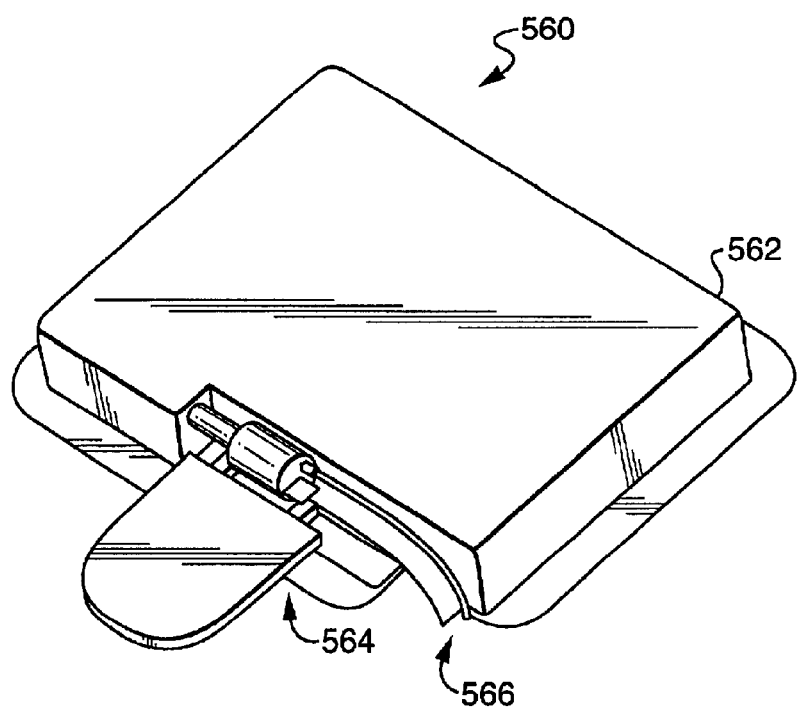
FIGS. 23A–23H are various views of another embodiment of a fluid delivery device in accordance with the present invention.
Figure 23B:
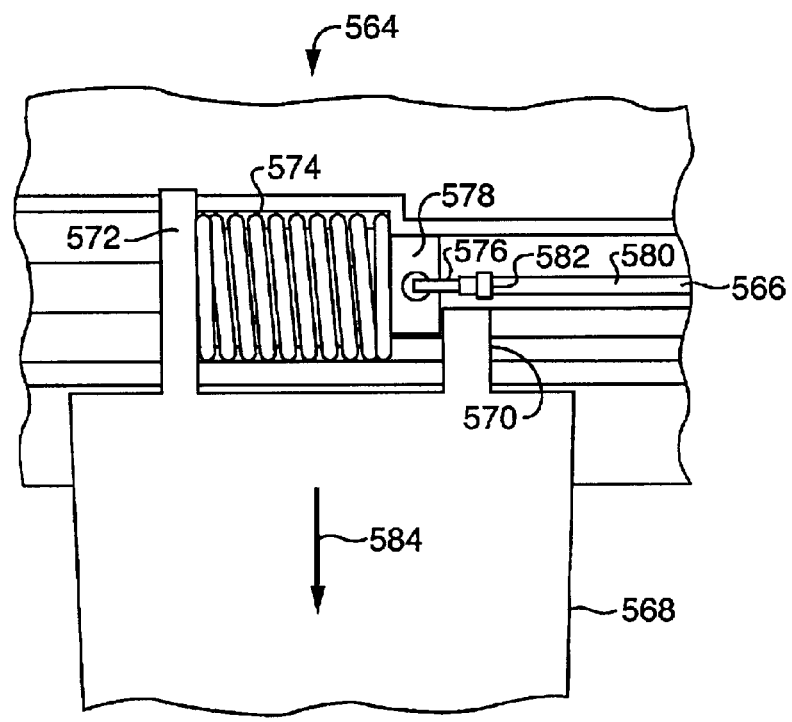
Figure 23C:
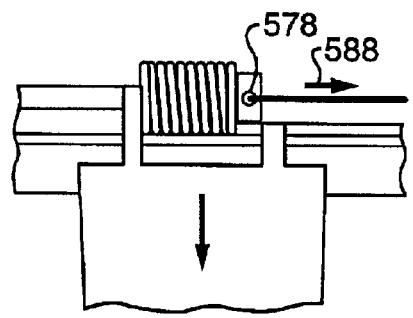
Figure 23D:
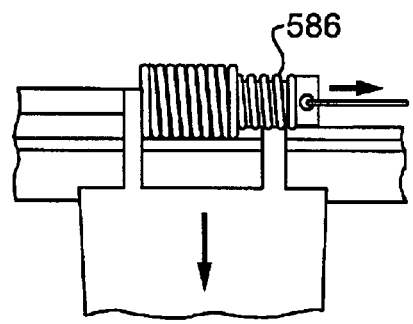
Figure 23E:
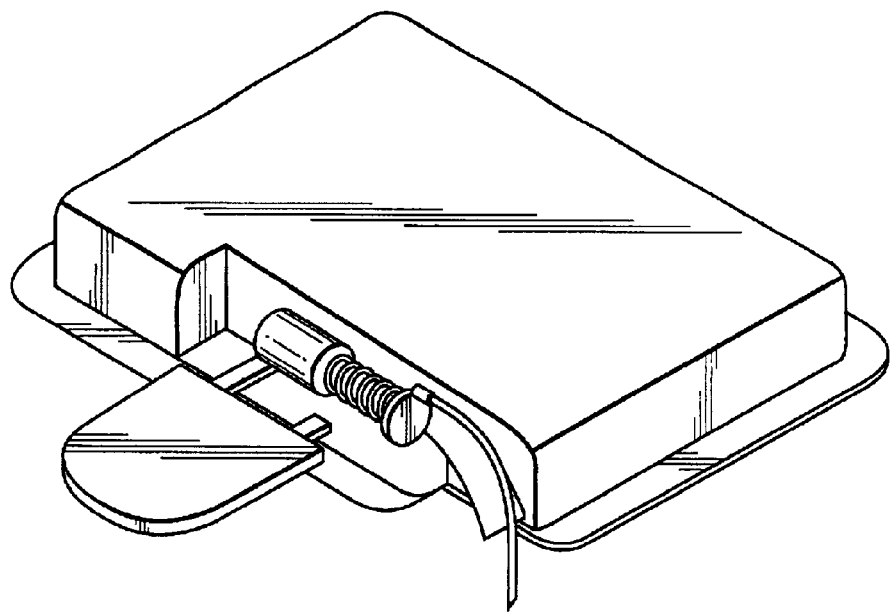
Figure 23F:
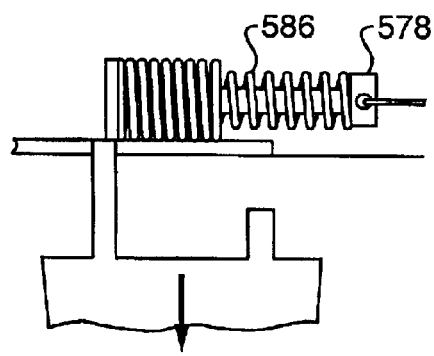
Figure 23G:
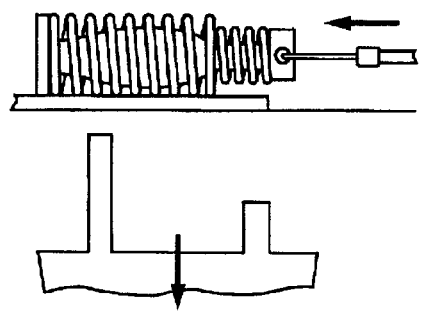

FIGS. 23A–23H show another embodiment 560 of the present invention. Fluid delivery device 560 includes a housing 562, an injection actuator 564 and a cannula assembly 566, FIG. 23A. As shown in FIG. 23B, injection actuator 564 includes an activation tab 568 having a deployment protrusion 570 and a retraction protrusion 570 and a retraction protrusion 572. A deployment spring, which is not visible in FIG. 23B, is disposed within a retraction spring 574 such that a longitudinal axis of the deployment spring coincides with a longitudinal axis of the retraction spring 574. Cannula assembly 566 includes a rigid cannula 576 coupled to a proximate end thereof to a head portion 578. A flexible cannula 580 is disposed on the rigid cannula 576 and includes a sliding seal portion which, as described above, enables the rigid cannula 576 to move relative to the flexible cannula while maintaining a fluid seal therebetween. The deployment spring and retraction spring 574 are coupled together at their ends proximate the retraction protrusion 572. The other, distal end of retraction spring 574 is prevented from moving toward the cannula assembly by a retaining member (not shown). Alternatively, in place of the sliding seal portion, flexible cannula 580 may include a bellows portion, as described above, for enabling the rigid cannula 576 to be retracted independent of the flexible cannula 580. Other embodiments that will enable independent movement between the rigid and flexible cannulas will be apparent to those skilled in the art.

The operation of fluid delivery device 560 begins when tab 568 is pulled in the direction indicated by arrow 584. Since deployment protrusion 570 is shorter than retraction protrusion 572, deployment spring 586, FIG. 23D, which was held in an energized state by the deployment protrusion 570, is allowed to deenergize and drive the head portion 578 of cannula assembly 566 in the direction indicated by arrow 588. This causes the head portion 578 to drive the rigid and flexible cannulas through the exit port of the housing 562 and into the skin of the person.

Figure 23H:
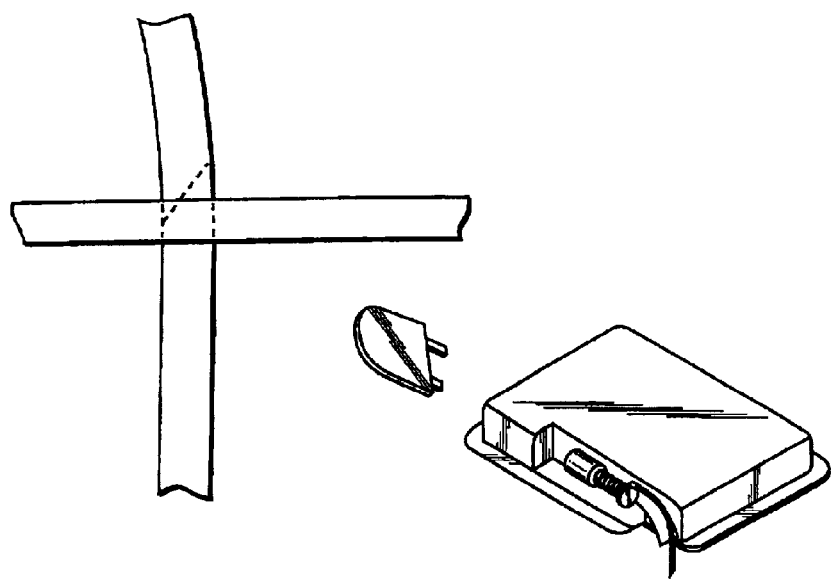

The difference in length between the deployment protrusion 570 and the retraction protrusion 572 is such that the deployment spring 586 is allowed to substantially fully deenergize before the retraction spring 574 is released by refraction protrusion 572. When retraction spring 574 is released by the retraction protrusion 572, FIGS. 23F–23G, retraction spring deenergizes by exerting a force on the end of deployment spring 586 to which it is coupled. The presence of the retaining member causes the retraction spring to drive the head portion 578 and rigid cannula 576 in the direction opposite that indicated by arrow 588. As shown in FIG. 23H, after both the deployment spring 586 and retraction string 574 have both been deenergized as described above, the flexible cannula 580 is injected into the skin of the person and the rigid cannula 576 and its penetrating member are retracted within the flexible cannula 580 to a position which may be anywhere between the deployed position of the flexible cannula 580 and the predeployed position shown in FIG. 23B. Alternatively, the rigid cannula 576 may be retracted to a position which is further away from the deployed position than the predeployment position. Flexible cannula 580 is held in the deployment position by the retention device, which may be one or more barbs disposed on either or both of the flexible cannula 580 and the exit port, as described below.

Figure 24:
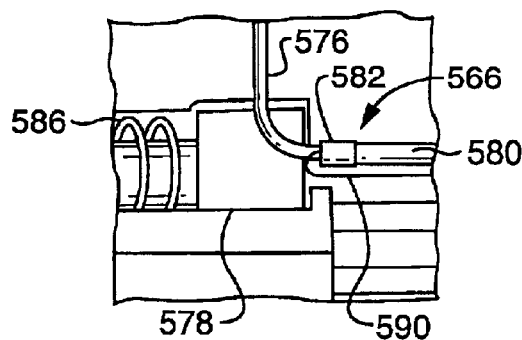
FIG. 24 is a cutaway view of another embodiment of a fluid delivery device in accordance with the present invention.
Figure 25A:
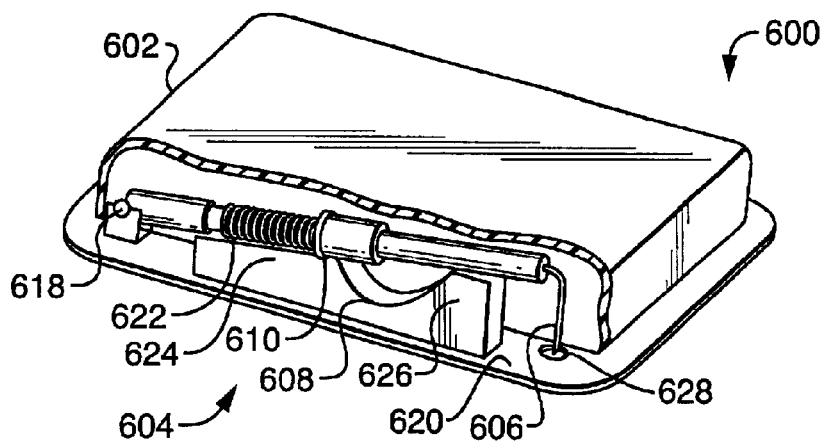
FIGS. 25A–25E are various views of another embodiment of a fluid delivery device in accordance with the present invention.
Figure 25B:
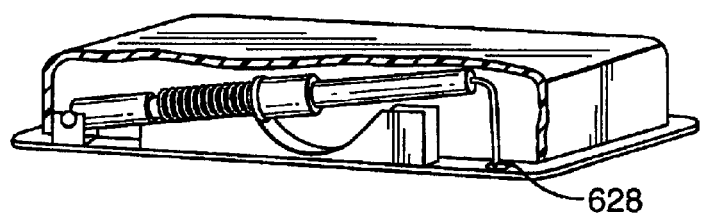
Figure 25C:
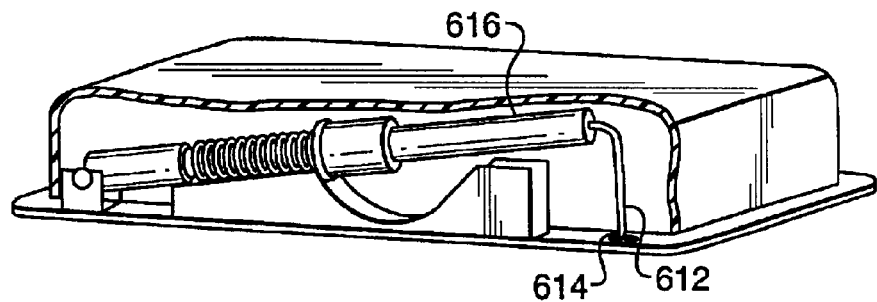
Figure 25D:
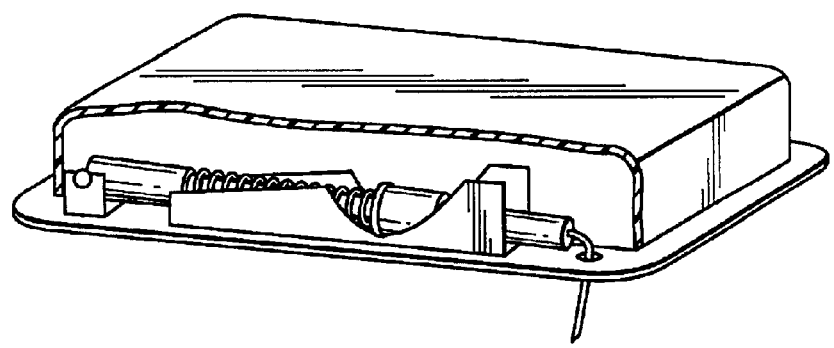
Figure 25E:
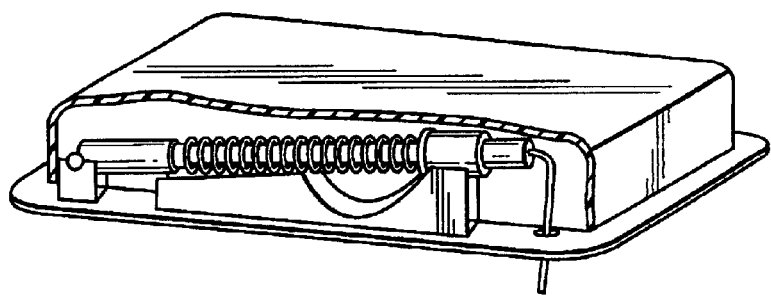
Figure 26A:
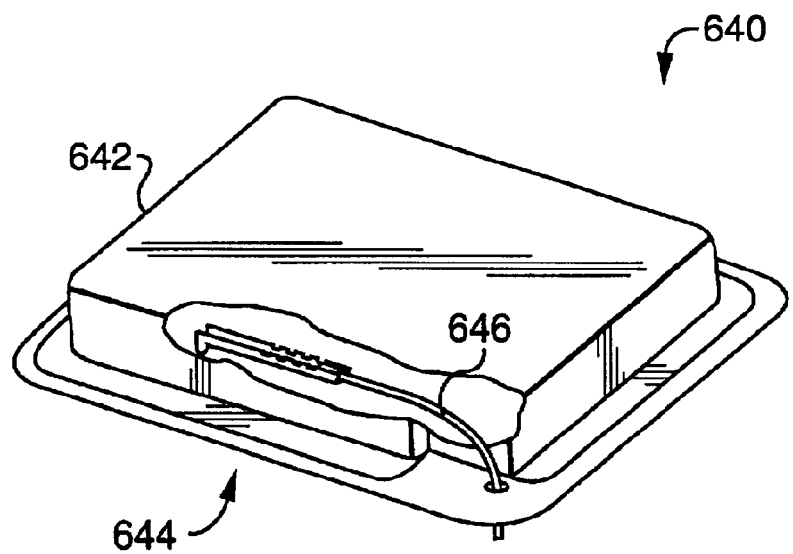
FIGS. 26A–26E are various views of another embodiment of a fluid delivery device in accordance with the present invention.
Figure 26B:
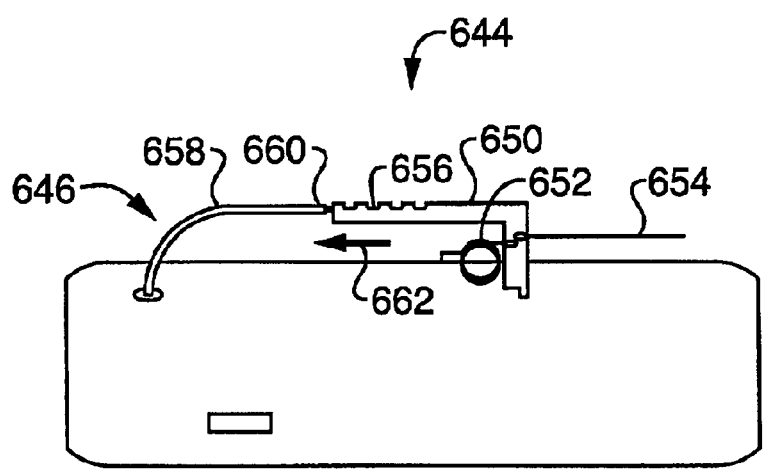
Figure 26C:
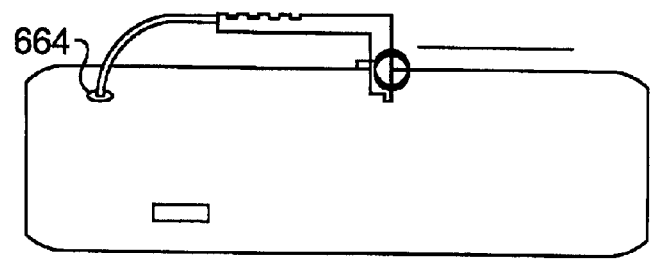
Figure 26D:
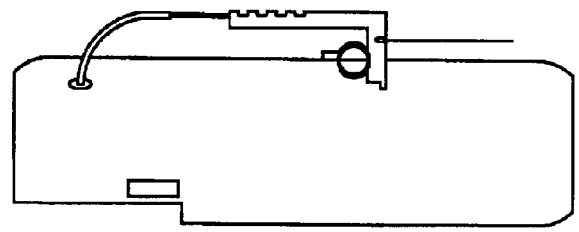
Figure 26E:
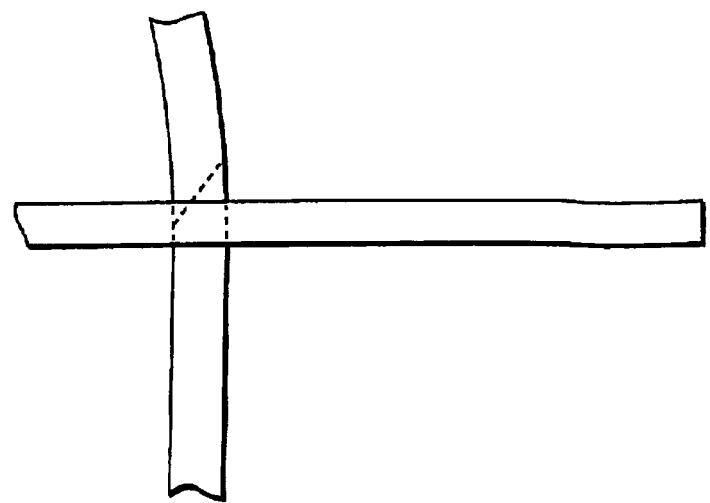

Alternatively, the retention device may include an interference member with which the sealing portion 582 of the flexible cannula comes into contact when the flexible cannula reaches the deployed position, wherein the interference member maintains the flexible cannula 580 in the deployed position when the rigid cannula 576 is retracted. Such a configuration is shown in FIG. 24, which depicts the deployment spring 586, head portion 578 and flexible cannula 580. As the cannula assembly 566 reaches the deployed position, interference member 590 contacts the sealing portion 582 of flexible cannula, thereby retaining the flexible cannula 580 in the deployed portion while the rigid cannula 576 and head portion 578 are retracted.

FIGS. 25A–25E show another embodiment 600 of the present invention. Fluid delivery device 600 includes a housing 602, an injection actuator 604 and a cannula assembly 606. Injection actuator 604 includes a cam follower assembly having a cam portion 60 and follower portion 610. Cannula assembly 606 includes a rigid cannula 614 disposed within a flexible cannula 612, both of which being disposed within a sleeve 616 along which cam follower portion 610 travels. Sleeve 616 is mounting to housing 602 at a pivot 618 and is biased toward the first wall 620. Injection actuator 604 further includes a spring 622 which is mounted between pivot 618 and cam follower 610. In the predeployment position shown in FIG. 25A and 25B, cam follower 610 is disposed on first ramp portion 624 of injection actuator device 604 and maintained in the position shown relative to the pivot 618 by a latch mechanism (not shown). In this position, spring 622 is in a compressed, energized state. Upon releasing the latch mechanism, spring 622 deenergizes and drives cam follower 610 along first ramp portion 624 and into cam portion 608, FIG. 25C. As cam follower portion slides into the cam, the cannula assembly 606 is driven toward first wall 620, out of the housing 602 through exit port 628 and into the skin of the person, FIG. 25D. As cam follower portion 610 continues to be driven by spring 622, it follows cam portion 608 up onto second ramp portion 626, which causes cannula assembly 606 to be lifted away from first wall 620, thereby retracting rigid cannula 604. Flexible cannula 612 is maintained in the deployed position shown in FIG. 25E, while rigid cannula 604 is retracted by the interference fit between the exit port 628 and a retraction prevention device (not shown), such as is described above. A bellows portion or sliding joint, both described above, may be utilized in connection with the flexible cannula to allow the rigid cannula to be retracted independently of the flexible cannula FIGS. 26A–26E show yet another embodiment 640 of the present invention. Fluid delivery device 640 includes a housing 642, an injection actuator 604 and a cannula assembly 646, FIG. 26A. Injection actuator 644 includes a deployment yoke 650, a spring 652 and a latch mechanism 654, FIG. 26B. Spring 652 is preferably a torsion spring having one end thereof mounted to the housing 642 and the other end mounted to the deployment yoke 650. In the predeployment position shown in FIG. 26B, torsion spring 652 is maintained in an energized state by a latch mechanism 654.

Cannula assembly 646 includes a rigid cannula 656 having a proximal end thereof coupled to the deployment yoke 650 and a flexible cannula 658 having a sealing portion 660 through which the rigid cannula 656 extends. Latch assembly 654 may be a mechanical latch or an electrically-activated latch formed, for example, from a shape memory alloy or polymer which contracts upon the application of an electrical charge thereto.

Upon activation of the latch mechanism 654, spring 652 is released and begins to deenergize. As it deenergizes, it drives deployment yoke 650, along with cannula assembly 646 in the direction indicated by arrow 662. This causes the cannula assembly to be driven out from the housing 642 through exit port 664 and into the skin of the person, FIG. 26C. As the spring 652 continues to deenergize by rotating its end that is coupled to the yoke 650, after the rigid cannula 656 and flexible cannula 658 have been injected into the person, the spring 652 drives the yoke away from the exit port in the direction opposite that indicated by arrow 662, thereby retracting the rigid cannula 652, FIG. 26D. The flexible cannula 658 remains in the deployed position shown in FIGS. 26D and 26E with the aid of a retention device such as described above.

Figure 27A:
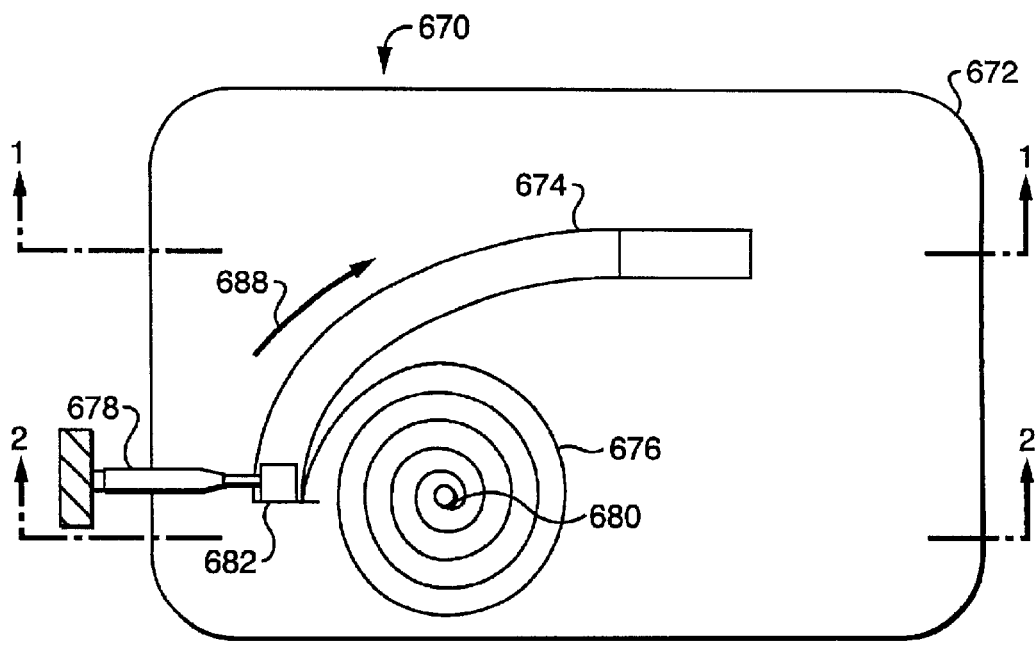
FIGS. 27A–27D are various views of another embodiment of a fluid delivery device in accordance with the present invention.
Figure 27B:
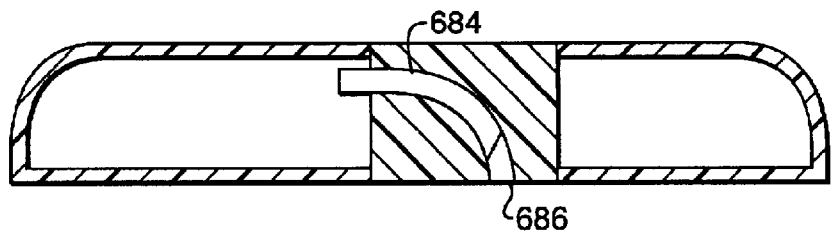
Figure 27C:
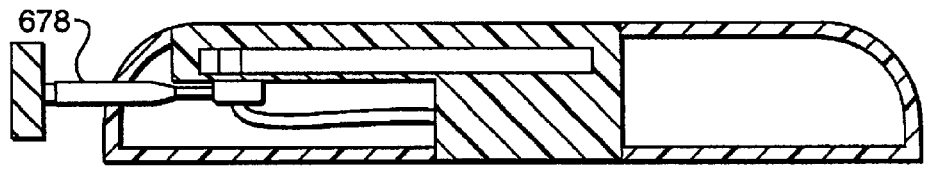
Figure 27D:
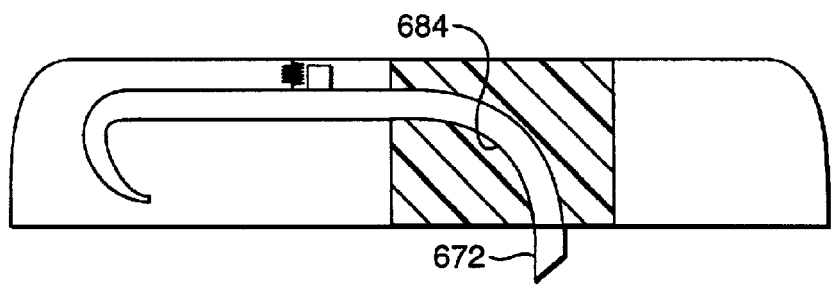

FIGS. 27A–27D show another embodiment 670 of the present invention. Fluid delivery device 670 includes a housing 672, a cannula assembly 674, a spring 676 and a latch mechanism 678. FIG. 27B is a cross-sectional view along line 1—1 of FIG. 27A, which shows that housing 672 includes a cannula guide portion 684 which guides the cannula assembly 674 out of the housing 672 via exit port 686. Spring 676 is preferably a torsion spring having one end 680 coupled to the housing and the other end 682 coupled to the cannula assembly 674. In the predeployment state shown in FIG. 27A, spring 676 is energized and cannula assembly 674 is maintained in its predeployment position by latch mechanism 678. Upon releasing latch mechanism 678 by pulling it from the housing 672, spring 676 is allowed to deenergize and drive cannula assembly 674 in the direction indicated by arrow 688 such that, with the aid of cannula guide portion 684, cannula assembly 674 is driven through exit port 686 and into the skin of the person. As shown in FIG. 27C, which is a cross-section view along line 2—2 of FIG. 27A, spring 676 is able to be mounted in a plane parallel to the skin of the person, which enables the size of the housing 672 to be reduced. Generally, the cannula assembly 674 is constructed to enable it to follow the arc of travel of end 682 of spring 676 as it deenergizes. FIG. 27D shows the cannula assembly 674 injected into the skin of the person through exit port 686 and cannula guide portion 684.

Figure 28:
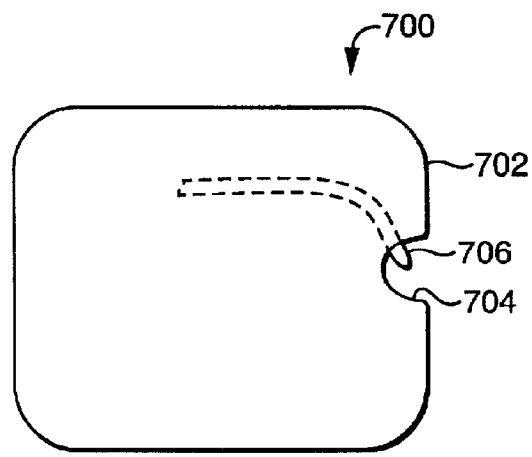
FIGS. 28 is a perspective view of another embodiment of a fluid delivery device in accordance with the present invention.
Figure 29:
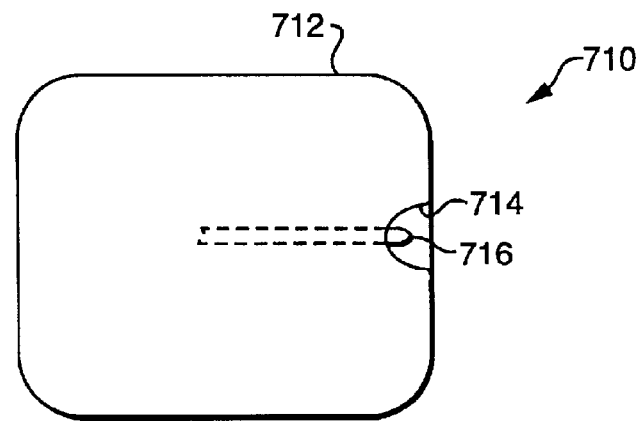
FIG. 29 is a perspective view of another embodiment of a fluid delivery device in accordance with the present invention.

In the fluid delivery devices of the present invention, it may be desirable to be able to view the site where the rigid cannula or the rigid and flexible cannulas have entered the skin of the person in order to inspect the site for infection or other concerns. Accordingly the housing of a fluid delivery device of the present invention may be modified to provide a viewing area. FIG. 28 shows an embodiment 700 which includes a housing 702 having a contour portion 704 and a cannula assembly 706. Contour portion 704 enables the cannula assembly 706 to be driven out of a side wall of the housing 702 and into the skin of the person, while providing protection for the injection site on three sides thereof. FIG. 29 shows an embodiment 710 which includes a housing 712 having a window portion 714 and a cannula assembly 716. Window portion 714 preferably is formed from a transparent material such as plastic, fits flush with the shape of the housing 712 and enables the person to view the injection site of the cannula assembly 716.

It will be understood that most or all of the embodiments of the fluid delivery device of the present invention which have been described herein may be used in connection with the housings 702 and 712 to provide a viewing area of the injection site.

Figure 30:
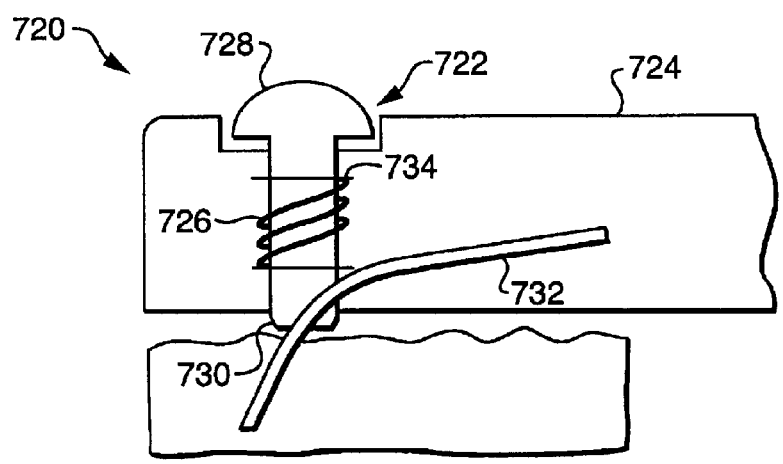
FIG. 30 is a cutaway view of another embodiment of a fluid delivery in accordance with the present invention.

FIG. 30 shows another embodiment 720 including a plunger device 722 mounted within a housing 724. This embodiment operates similar to the embodiment described with reference to FIGS. 3A–3C, wherein plunger device 722 includes a body portion 726, a head portion 728 and a cannula engagement portion 730 for engaging cannula 732. In the embodiment, however, plunger assembly is formed from a transparent material which enables the injection site to be seen therethrough. A spring 734 biases the plunger device 722 against the injection site to provide a clear view of the site through the plunger device 722. In one embodiment, plunger device 722 is constructed in such a way that the view of the injection site is magnified when viewed through the head portion 758 of the plunger device 722. In another embodiment, a light source (not shown) may be directed at the plunger device 722 to illuminate the injection site.

One advantage of the fluid delivery device of the present invention is that it requires only one small housing to be attached to the person. In contrast to prior art fluid delivery devices, which may have included multiple bulky parts, the present invention enables the person to be more active while wearing the fluid delivery device than would be the case with the prior art devices. However, it is important to maintain the cannula assembly in the proper deployed position throughout the period that the device is attached to the person, despite the movement and activity of the person. Since the fluid delivery devices of the present invention are typically attached to the abdominal area of the person, normal body motion and bending could cause a portion of the housing to flex away from the skin. Over time, a cannula which is rigidly fixed with respect to the housing may have the tendency to creep out of the injection site, which may result in the cannula completely pulling out of the injection site, or in a flexible cannula developing enough slack to cause kinking in the cannula. FIGS. 31–34 show embodiments of the present invention which enable the housing of the fluid delivery device to move independently of the cannula assembly, without affecting the position of the cannula within the person.

Figure 31:
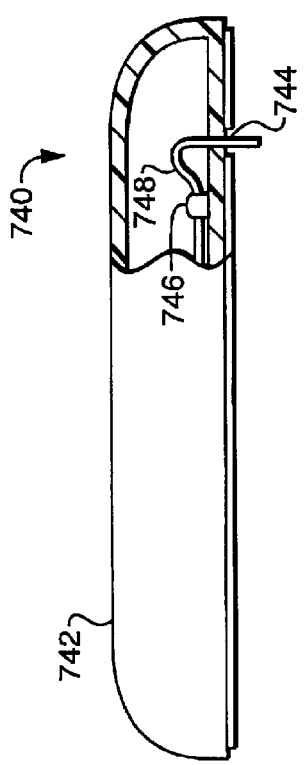
FIG. 31 is a cutaway view of another embodiment of a fluid delivery device in accordance with the present invention.

FIG. 31 shows an embodiment 740 of the present invention that includes a housing 742 and a cannula assembly 744. Cannula assembly 744 preferably includes a flexible cannula which is attached to the first wall of the housing 742 with a tie-down device 746. The cannula assembly is injected into the person in such a way that a loop 748 is present between the injection site and the tie-down 746. This loop provides the slack necessary to prevent any tugging on the portion of the cannula assembly injected into the person if the housing was to be moved away from the injection site.

Figure 32:
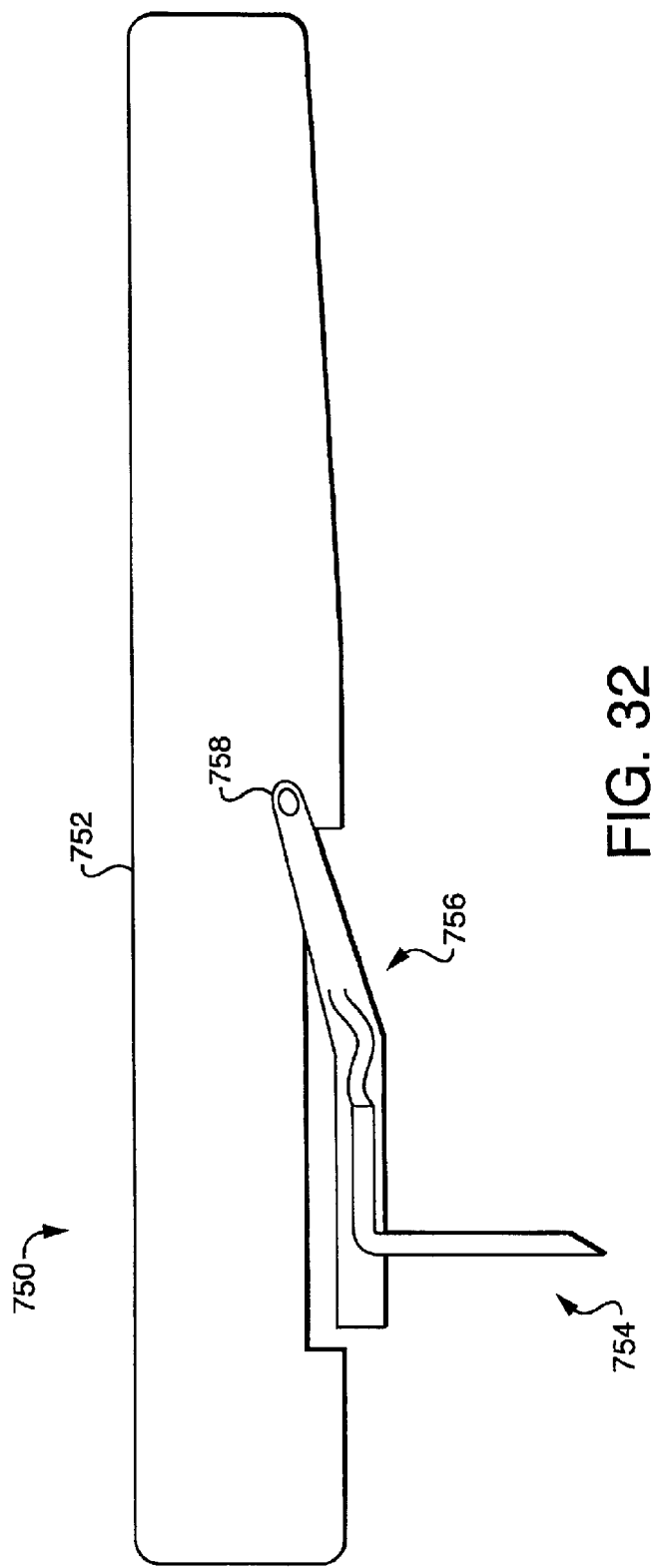
FIG. 32 is a cutaway view of another embodiment of a fluid delivery device in accordance with the present invention.

FIG. 32 shows an embodiment 750 including a housing 752 and a cannula assembly 754 attached to a strut assembly 756 which is pivotally attached to the housing 752 at point 758. Strut assembly 756 is biased toward the skin of the person, such that, upon any movement of the housing away from the skin, the strut assembly 756 maintains the cannula assembly in the deployed position shown in the figure.

FIG. 33 shows an embodiment 760 including a housing 762 and a cannula assembly 764 which is coupled to a floating member 766 which is biased against the skin of the person by spring 768. As the person moves, any the cannula assembly 764 and floating member 766 are maintained in contact with the skin, thus enabling the housing to move independently of the cannula assembly 764 in three dimensions, as shown by arrows 780 and 782.

FIG. 34 shows an embodiment 770 including a housing 772 and a cannula assembly 774 which is coupled to a floating member 766 which is biased against the skin of the person by spring 768. In this embodiment, the spring 778 is coupled between the cannula assembly 774 and the floating member 776 to enable the housing 772 to move independently of the cannula assembly in three dimensions.

Figure 35A:
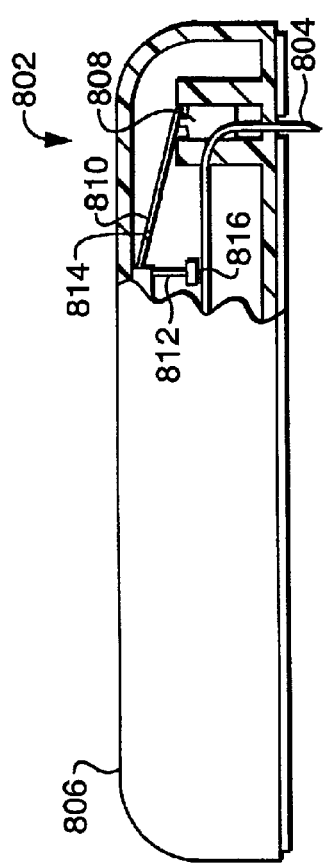
FIGS. 35A–35B are various views of another embodiment of a fluid delivery device in accordance with the present invention.
Figure 35B:
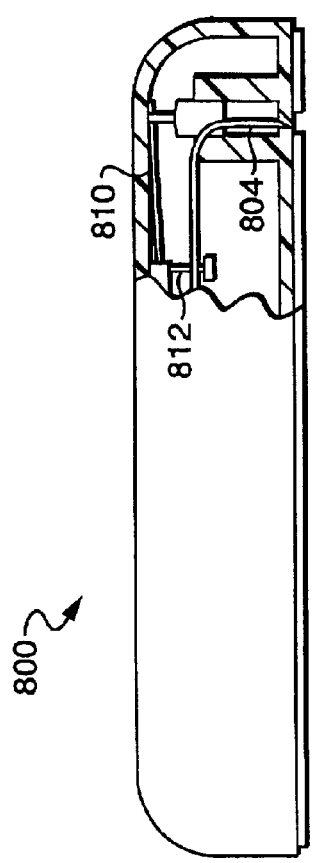

FIGS. 35A–B show an embodiment 800 which includes a housing 806 and a retraction mechanism 802 for retracting a cannula 804 when the fluid delivery device has completed the infusion and is ready to be removed from the skin of the patient. As shown in FIG. 35A, cannula 804 is injected into the skin of the person through an exit port of the fluid delivery device 800. Retraction mechanism 802 includes a retraction member 808 coupled to the cannula 804, a lever 810 coupled at one end to the retraction member 804 and at the other end to an actuator 812. Lever 810 is also coupled to a pivot point 814 of the housing 806. Actuator 812 preferably includes a shape memory alloy or polymer which contracts under the influence of an electrical charge coupled between the lever 810 and a portion 816 of housing 806. However, other devices may be utilized for the actuator 812, such as a piezo electric actuator and a solenoid.

Upon the application of an electrical charge to the actuator 812, by the local processor triggered by a command from the remote control or other means described above, actuator contracts causing lever 810 to pull retraction member 808 and consequently, cannula 804 away from the skin of the person, thus retracting the cannula 804 from the skin of the person, as shown in FIG. 35B. This retraction mechanism 802 may be combined with any of the fluid delivery devices described above having only injection mechanisms, to enable the device to both inject and retract the cannulas.

Figure 36A:
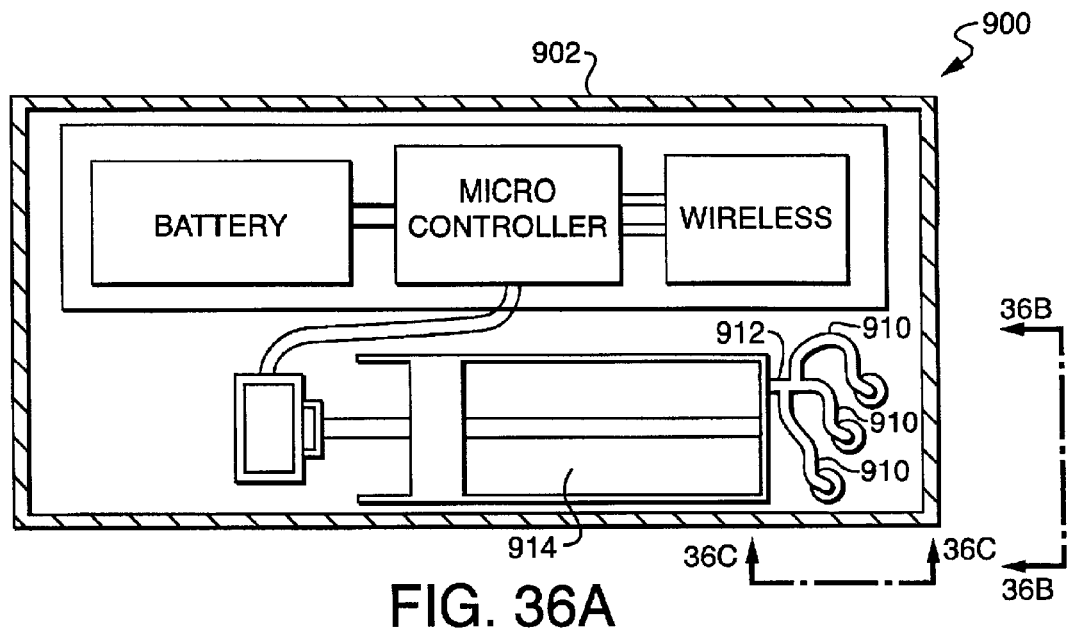
FIGS. 36A–36C are various views of another embodiment of a fluid delivery device in accordance with the present invention.
Figure 36B:
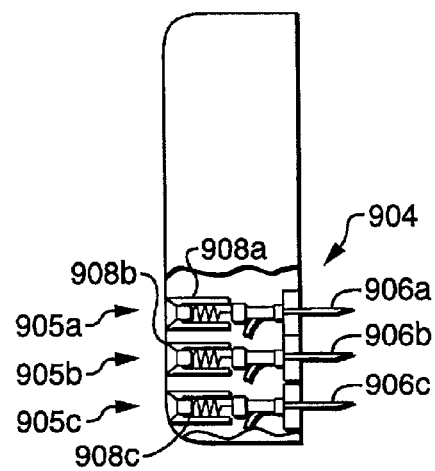
Figure 36C:
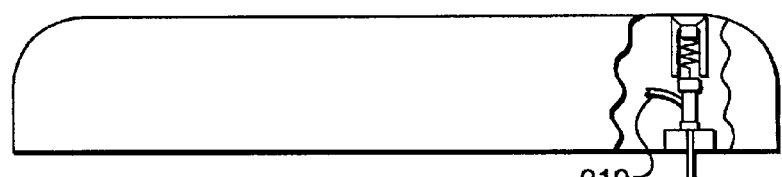

FIGS. 36A–36C show yet another embodiment 900 of the present invention. Fluid delivery device 900 includes a housing 902 for enclosing the electronics, control mechanism and fluid reservoir, as described above. Device 900 further includes a cannula assembly 904. As shown in FIG. 36A, which is a top view of the device 900, FIG. 36B, which is a side cutaway view of the device 900 as seen from line 36B—36B of FIG. 36A and FIG. 36C, which is a side cutaway view of the device 900 as seen from line 36C—36C of FIG. 36A, cannula assembly 904 includes three cannula devices, 905a, 905b and 905c, including cannulas 906a, 906b and 906c and injection actuators 908a, 908b and 908c, respectively. Injection and/or retraction actuators 908a–908c may be constructed according to any of the embodiments described above. Each cannula device 905 includes a fluid path 910 that branches from a main fluid path 912 which delivers fluid from the reservoir 914 to each cannula 906. The injection actuators are activated individually for a predetermined period of time before the next injection actuator is activated.

For example, in a case where the reservoir 914 is capable of containing nine days of the fluid medication, but, according to regulatory measures, a single cannula cannot be maintained in the skin of the person for more than three days, a fluid delivery device such as the embodiment 900 may be utilized as follows. In the predeployment state, all the cannula devices are retracted within the housing and are not actively connected to their respective fluid paths 910. After the housing has been attached to the skin of the person, one of the three cannula devices is activated. The activation may be effected by any of the activation devices described in this application. When a cannula device is activated and the cannula 906 is driven into the skin of the person, a valve (not shown) within the injection actuator is opened, thus enabling fluid to flow from the reservoir 914 through the cannula to the person. At the end of the three day period, the person can retract the cannula, which shuts the valve, and activate a second cannula device, thereby enabling fluid to flow from the reservoir to the person through the second cannula device. This process is repeated until all of the cannula devices have been activated and then retracted. Although not specifically shown, each cannula device includes a mechanism that prevents the activation of an injection actuator that has already been activated. It will be understood that, although three cannula devices are shown in FIGS. 36A–36C, any number of cannula devices may be included in the fluid delivery device 900.

Accordingly, the present invention provides a fluid delivery device that enables a person to conveniently and comfortably self-administer a drug regimen by allowing the person to maintain a constant flow of a fluid drug for a period of time without having to carry multiple pieces of equipment. The fluid delivery device of the present invention is inexpensive to manufacture and is either disposable or semi-disposable.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A device for delivering fluid to a person comprising:
   a reservoir for containing a fluid to be delivered to the person;
   a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device;
   a housing containing said reservoir and said fluid transport device, said housing including an exit port for receiving said distal end of said fluid transport device upon injection of said distal end into said person and means for securing a first wall of said housing to the skin of the person; and
   an injection activation device including a driving mechanism contacting said fluid transport device for driving said penetrating member from a first position within said housing, through said exit port to a second position, external to said housing and into the skin of said person;
   wherein said driving mechanism of said injection activation device comprises a plunger having a body portion extending through an aperture in a second wall of said housing and coupled to said distal end of said fluid transport device, such that the application of a force to said plunger drives said penetrating member from said first position to said second position.

2. The device of claim 1 wherein said housing includes a transparent portion disposed proximate said exit port, for providing a view of an entry site of said fluid transport device in the person's skin.

3. The device of claim 1, said plunger including a friction member disposed on said body portion, said friction member causing said body portion of said plunger to have a width dimension which is slightly larger than a width dimension of said aperture of said housing, thus requiring a specific force to be applied to said plunger to enable said friction member to pass through said aperture, said specific force being translated to said distal end of said fluid transport device.

4. The device of claim 3 wherein said friction member is an annular flange.

5. The device of claim 3, said plunger further comprising a head portion for stopping travel of said plunger by contacting said housing.

6. The device of claim 5 wherein said plunger is removable from said housing after said penetrating member is driven to said second position.

7. A device for delivering fluid to a person comprising:
   a reservoir for containing a fluid to be delivered to the person;
   a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device;

a housing containing said reservoir and said fluid transport device, said housing including an exit port for receiving said distal end of said fluid transport device upon injection of said distal end into said person and means for securing a first wall of said housing to the skin of the person; and an injection activation device including a driving mechanism contacting said fluid transport device for driving said penetrating member from a first position within said housing, through said exit port to a second position, external to said housing and into the skin of said person wherein said driving mechanism of said injection activation device comprises a plunger contained within said housing, said plunger having a first end including a lateral protrusion and a second end coupled to said distal end of said fluid transport device, said injection activation device further including a biasing spring for biasing said plunger for driving said penetrating member from said first position to said second position, and said lateral protrusion being in contact with an internal ridge of said housing, with said penetrating member in said first position, thereby preventing said plunger from driving said penetrating member from said first position to said second position;

said housing including an actuator for urging said lateral protrusion from said internal ridge, thereby causing said plunger to drive said penetrating member from said first position to said second position.

8. The device of claim 7 wherein said actuator comprises a finger coupled to an inside surface of a flexible wall portion of said housing, a distal end of said finger being in contact with said lateral protrusion such that an application of pressure to said flexible wall portion causes said finger to urge said lateral protrusion from said ridge, thereby causing said plunger to drive said penetrating member from said first position to said second position.

9. The device of claim 8 wherein said distal end of said finger, upon the application of pressure to said flexible wall portion, moves in same the direction as the flexible wall portion.

10. The device of claim 8 wherein said distal end of said finger, upon the application of pressure to said flexible wall portion, moves in a substantially opposite direction as the flexible wall portion.

11. The device of claim 10 wherein said finger includes a pivot which causes the distal end of the finger to move in a direction substantially opposite that of the flexible wall portion.

12. A device for delivering fluid to a person comprising:

a reservoir for containing a fluid to be delivered to the person;

a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device;

a housing containing said reservoir and said fluid transport device, said housing including an exit port for receiving said distal end of said fluid transport device upon injection of said distal end into said person and means for securing a first wall of said housing to the skin of the person; and an injection activation device including a driving mechanism contacting said fluid transport device for driving said penetrating member from a first position within said housing, through said exit port to a second position, external to said housing and into the skin of said person wherein said driving mechanism of said injection activation device comprises a pivoting arm and said injection activation device further includes a latch assembly, said pivoting arm having a proximal end pivotally coupled to an inside surface of a wall of said housing and a distal end in contact with said latch assembly integral with a side wall of said housing, said fluid transport device being coupled to said arm such that when said distal end of said arm is in contact with said latch assembly, said penetrating member is in said first position;

said injection activation device further includes a biasing spring attached between said proximal and distal ends of said arm and a wall of said housing, said biasing spring urging said arm to drive said penetrating member to said second position; and said latch assembly includes a latch for contacting said distal end of said pivoting arm to prevent said pivoting arm from driving said penetrating member from said first position to said second position under the influence of said biasing spring and a latch release mechanism for moving said latch out of contact with said distal end of said pivoting arm, thereby enabling said pivoting arm to drive said penetrating member from said first position to said second position under the influence of said biasing spring.

13. The device of claim 12 wherein said latch release mechanism includes an electrically driven actuator coupled between said latch and said side wall of said housing, such that, upon the application of a charge to said electrically driven actuator, said electrically driven actuator moves said latch out of contact with said distal end of said pivoting arm.

14. The device of claim 13 wherein said electrically driven actuator comprises one of a shape memory alloy, a shape memory polymer, a piezo electric actuator and a solenoid.

15. The device of claim 13 further comprising a local processor connected to the latch release mechanism and programmed to apply a charge to said electrically driven actuator based on injection instructions; and a wireless receiver connected to the local processor for receiving injection instructions from a separate, remote control device and delivering the injection instructions to the local processor.

16. The device of claim 15 wherein said housing is free of user input components for providing injection instructions to the local processor.

17. The device of claim 15 further comprising a remote control device separate from the fluid delivery device and including:

a remote processor;

user interface components connected to the remote processor for transmitting the injection instructions to the remote processor; and a transmitter connected to the remote processor for transmitting the injection instructions to the receiver of the fluid delivery device.

18. The device of claim 12 wherein said latch release mechanism includes a mechanical lever coupled to said latch and protruding through said side wall, such that, upon said lever being pulled away from said housing, said latch is pulled out of contact with said distal end of said pivoting arm.

19. The device of claim 1 wherein said injection activation device includes a discrete secondary housing, said plunger including a first end having a lateral protrusion and a second end in frictional contact with said distal end of said fluid transport device, said second end of said plunger extending from within said secondary housing, out of a distal end thereof into said aperture of said housing and into frictional contact with said distal end of said fluid transport device;

said injection activation device further comprising a biasing spring coupled between said first end of said plunger and a proximal end of said secondary housing within said secondary housing for biasing said plunger for driving said penetrating member from said first position to said second position, said lateral protrusion being in contact with an internal ridge of said secondary housing, with said penetrating member in said first position, thereby preventing said plunger from driving said penetrating member from said first position to said second position;

said secondary housing including an actuator for urging said lateral protrusion from said internal ridge, thereby causing said plunger to drive said penetrating member from said first position to said second position.

20. The device of claim 1 wherein said injection activation device includes a discrete secondary housing, said plunger including a first end having a lateral protrusion and a second end in frictional contact with said distal end of said fluid transport device, said second end of said plunger extending from within said secondary housing, out of a distal end thereof into said aperture of said housing and into frictional contact with said distal end of said fluid transport device;

said injection activation device further comprising a biasing spring coupled between said first end of said plunger and a proximal end of said secondary housing within said secondary housing for biasing said plunger for driving said penetrating member from said first position to said second position, said lateral protrusion being in contact with a latch assembly of said secondary housing, with said penetrating member in said first position, thereby preventing said plunger from driving said penetrating member from said first position to said second position;

said latch assembly includes a latch for contacting said lateral protrusion of said plunger to prevent said plunger from driving said penetrating member from said first position to said second position under the influence of said biasing spring and a latch release mechanism coupled to said housing for moving said latch out of contact with said lateral protrusion, thereby enabling said plunger to drive said penetrating member from said first position to said second position under the influence of said biasing spring.

21. The device of claim 18 wherein said latch release mechanism includes an electrically driven actuator coupled between said latch and said side wall of said housing, such that, upon the application of a charge to said electrically driven actuator, said electrically driven actuator activates to pull said latch out of contact with said distal end of said pivoting arm.

22. The device of claim 21 wherein said electrically driven actuator comprises one of a shape memory alloy, a shape memory polymer, a piezo electric actuator and a solenoid.

23. The device of claim 21 further comprising a local processor housed in said secondary housing, said local processor being connected to the latch release mechanism and programmed to apply a charge to said electrically driven actuator based on injection instructions; and a wireless receiver connected to the local processor for receiving injection instructions from a separate, remote control device and delivering the injection instructions to the local processor.

24. The device of claim 23 wherein said housing is free of user input components for providing injection instructions to the local processor.

25. The device of claim 23 further comprising a remote control device separate from the fluid delivery device and including:

a remote processor;

user interface components connected to the remote processor for transmitting the injection instructions to the remote processor; and a transmitter connected to the remote processor for transmitting the injection instructions to the receiver of the fluid delivery device.

26. The device of claim 20 wherein said latch release mechanism includes a mechanical lever coupled to said latch and protruding through said side wall, such that, upon an application of force to said lever, said latch is moved out of contact with said distal end of said pivoting arm.

27. A device for delivering fluid to a person comprising:

a reservoir for containing a fluid to be delivered to the person;

a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device;

a housing containing said reservoir and said fluid transport device, said housing including an exit port for receiving said distal end of said fluid transport device upon injection of said distal end into said person and means for securing a first wall of said housing to the skin of the person;

an injection activation device including a driving mechanism contacting said fluid transport device for driving said penetrating member from a first position within said housing, through said exit port to a second position, external to said housing and into the skin of said person;

said driving mechanism comprising a plunger having a first end coupled to said distal end of said fluid transport device, said plunger being biased to drive said penetrating member from said first position to said second position, said injection activation device further comprising a latch for contacting said plunger to maintain said penetrating member in said first position, said latch including an electrically driven actuator coupled to said latch, such that, upon the application of a charge to said electrically driven actuator, said electrically driven actuator releases said plunger to drive said penetrating means from said first position to said second position.

28. The device of claim 27 wherein said electrically driven actuator comprises one of a shape memory alloy, a shape memory polymer, a piezo electric actuator and a solenoid.

29. The device of claim 27 further comprising a local processor connected to the latch release mechanism and programmed to apply a charge to said electrically driven actuator based on injection instructions; and a wireless receiver connected to the local processor for receiving injection instructions from a separate, remote control device and delivering the injection instructions to the local processor.

30. A device for delivering fluid to a person comprising:

a reservoir for containing a fluid to be delivered to the person;

a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device, said proximal end being connected to said distal end by a medial portion of said fluid transport device;

a housing containing said reservoir and said fluid transport device, said housing including an exit port for receiving said distal end of said fluid transport device upon injection of said penetrating member into said person and means for securing a first wall of said housing to the skin of the person; and an injection activation device including a driving mechanism contacting said fluid transport device for driving said penetrating member from a first position within said housing, through said exit port to a second position, external to said housing and into the skin of said person;

wherein said medial portion is disposed substantially parallel to said first wall of said housing and includes a lateral protrusion which, with said penetrating member in said first position, is biased against a latch assembly of said injection activation device by a biasing spring of said injection activation device, which is coupled between said lateral protrusion and an internal ridge of said housing, said biasing spring being in an energized state such that, upon activating said latch assembly, said biasing spring drives said fluid transport device in a direction of travel substantially parallel to said first wall, resulting in said penetrating member being driven from said first position to said second position.

31. The device of claim 30 wherein said distal end of said fluid transport device is flexible; and said housing includes a deflecting device in the path of travel of said fluid transport device;

wherein, upon activating said latch assembly, said distal end of said fluid transport device contacts said deflecting device which causes said distal end of said fluid transport device to be deflected from said direction of travel substantially parallel to said first wall of said housing to a second direction of travel at an angle of at least 15°.

32. The device of claim 31 wherein said second direction of travel is up to 90°.

33. The device of claim 31 wherein said latch assembly includes a latch for contacting said lateral protrusion of said fluid transport device to prevent said biasing spring from driving said penetrating member from said first position to said second position and a latch release mechanism coupled to said housing for moving said latch out of contact with said lateral protrusion, thereby enabling said biasing spring to drive said penetrating member from said first position to said second position.

34. The device of claim 33 wherein said latch release mechanism includes an electrically driven actuator coupled between said latch and said housing, such that, upon the application of a charge to said electrically driven actuator, said shape memory allow wire contracts, pulling said latch out of contact with said lateral protrusion of said fluid transport device.

35. The device of claim 34 wherein said electrically driven actuator comprises one of a shape memory alloy, a shape memory polymer, a piezo electric actuator and a solenoid.

36. The device of claim 34 further comprising a local processor connected to the latch release mechanism and programmed to apply a charge to said electrically driven actuator based on injection instructions; and a wireless receiver connected to the local processor for receiving injection instructions from a separate, remote control device and delivering the injection instructions to the local processor.

37. The device of claim 36 wherein said housing is free of user input components for providing injection instructions to the local processor.

38. The device of claim 36 further comprising a remote control device separate from the fluid delivery device and including:

a remote processor;

user interface components connected to the remote processor for transmitting the injection instructions to the remote processor; and a transmitter connected to the remote processor for transmitting the injection instructions to the receiver of the fluid delivery device.

39. The device of claim 33 wherein said latch release mechanism includes a mechanical lever coupled to said latch and protruding through said side wall, such that, upon an application of force to said lever, said latch is moved out of contact with said distal end of said pivoting arm.

40. The device of claim 30 wherein said biasing spring comprises one of a torsional spring, a coil spring, a helical spring, a compression spring, an extension spring, an air spring, a wave spring, a conical spring, a constant force spring, a belleville spring and a beehive spring.

41. A device for delivering fluid to a person comprising:

a reservoir for containing a fluid to be delivered to the person;

a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device;

a housing containing said reservoir and said fluid transport device, said housing including an exit port for receiving said distal end of said fluid transport device upon injection of said distal end into said person and means for securing a first wall of said housing to the skin of the person; and an injection activation device including a driving mechanism contacting said fluid transport device for driving said penetrating member from a first position within said housing, through said exit port to a second position, external to said housing and into the skin of said person;

wherein said driving mechanism includes a lever having a first portion coupled to a drive axle and a second portion, opposite said first portion, contacting said fluid transport device;

said injection activation device further comprising driving means operatively coupled to said drive axle for rotating said drive axle upon activation of said driving means, said second portion of said lever driving said penetrating member from said first position to said second position upon rotation of said drive axle.

42. The device of claim 41 wherein said lever comprises a disk.

43. The device of claim 41 wherein said driving means comprises a motor.

44. The device of claim 41 wherein said driving means comprises an energized coil spring disposed about said drive axle which, when deenergized, causes said drive axle to rotate.

45. A device for delivering fluid to a person comprising:
a reservoir for containing a fluid to be delivered to the person;
a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device, said proximal end being connected to said distal end by a medial portion of said fluid transport device;
a housing containing said reservoir and said fluid transport device, said housing including an exit port for receiving said distal end of said fluid transport device upon injection of said distal end into said person and means for securing a first wall of said housing to the skin of the person; and
an injection activation device including a driving mechanism contacting said fluid transport device for driving said penetrating member from a first position within said housing, through said exit port to a second position, external to said housing and into the skin of said person;
wherein said medical portion is disposed substantially parallel to said first wall of said housing and includes a lateral protrusion;
said driving mechanism including an urging device disposed on one side of said lateral protrusion, said urging device being movable into contact with said lateral protrusion to urge said lateral protrusion downward, relative to said urging device, causing said penetrating member to be driven from said first position to said second position.

46. A device for delivering fluid to a person comprising:
a reservoir for containing a fluid to be delivered to the person;
a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device;
a housing containing said reservoir and said fluid transport device, said housing including an exit port for receiving said distal end of said fluid transport device upon injection of said distal end into said person and means for securing a first wall of said housing to the skin of the person; and an injection activation device contacting said fluid transport device for driving said penetrating member from a first position within said housing, through said exit port to a second position, external to said housing and into the skin of the person;
said fluid transport device comprising a needle housed within a flexible cannula, said penetrating member being disposed at a distal end of said needle, said flexible cannula including a bellows portion proximate a distal end thereof, wherein, when said fluid transport device is in said first position, said bellows portion of said soft cannula is in a compressed state and said penetrating member extends beyond said distal end of said flexible cannula;
said injection activation device comprising a plunger having a body portion coupled to said fluid transport device between said proximal end and said bellows portion of said flexible cannula, such that the application of a first force in a first direction to said plunger drives said fluid transport device from said first position to said second position, wherein said penetrating member of said needle and said distal end of said flexible cannula extend through said exit port and into the skin of the person.

47. The device of claim 46 wherein, upon application of a second force to said plunger in a second direction substantially opposite said first direction, said penetrating member of said needle is retracted to a third position, and said bellows portion of said flexible cannula is extended, thereby enabling said distal end of said flexible cannula to remain in said second position.

48. The device of claim 47 wherein said plunger extends through a second wall of said housing and includes a head portion exterior to said housing, said first force being applied directly to said head portion by a person to drive said fluid transport device from said first position to said second position.

49. The device of claim 48 wherein said second force is applied directly to said head portion by a person to move said penetrating member of said needle to said third position.

50. The device of claim 48 wherein said injection activation device includes a spring coupled between said plunger and an interior wall of said housing, said spring being in a deenergized state when said fluid transport device is in said first position and in an energized state when said fluid transport device is in said second position, wherein, upon a termination of the application of said first force, said spring applies said second force to said plunger, thereby causing said penetrating member to move to said third position.

51. The device of claim 47 wherein said plunger includes a lateral protrusion and said injection activation device includes a first spring in an energized state and positioned relative to said lateral protrusion to impart said first force upon releasing its energy and a second spring in an energized state and positioned relative to said lateral protrusion to impart said second force upon releasing its energy and said injection activation device includes a latch assembly for maintaining said first spring in its energized state and said second spring in its energized state.

52. The device of claim 51 wherein said latch assembly includes a first latch arm movable between a closed position, in which said first spring is maintained in said energized state and an open position, in which said first spring is released from said energized state, thereby imparting said first force to said lateral protrusion to drive said fluid transport device from said first position to said second position.

53. The device of claim 52 wherein said first latch arm is held in said closed position by contact with said first spring and wherein said first latch arm is moved to said open state by a first latch activation device.

54. The device of claim 53 wherein said first latch activation device comprises a first electrically driven actuator coupled to said latch arm, such that, upon the application of a charge to said first electrically driven actuator, said first electrically driven actuator activates, causing said latch arm to move from said closed position to said open position.

55. The device of claim 54 wherein said first electrically driven actuator comprises one of a shape memory alloy, a shape memory polymer, a piezo electric actuator and a solenoid.

56. The device of claim 54 wherein said latch assembly includes a second latch arm movable between a closed position, in which said second spring is maintained in said energized state and an open position, in which said second spring is released from said energized state, thereby imparting said second force to said lateral protrusion to drive said fluid transport device from said second position to said third position.

57. The device of claim 56 wherein said second latch arm is held in said closed position by contact with said second spring and wherein said second latch arm is moved to said open state by a second latch activation device.

58. The device of claim 57 wherein said second latch activation device comprises a second electrically driven actuator coupled between said second latch arm and said housing, such that, upon the application of a charge to said second electrically driven actuator, said second electrically driven actuator activates, causing said second latch arm to move from said closed position to said open position.

59. The device of claim 58 wherein said second electrically driven actuator comprises one of a shape memory alloy, a shape memory polymer, a piezo electric actuator and a solenoid.

60. The device of claim 54 further comprising a local processor connected to the first latch activation device and programmed to apply a charge to said electrically driven actuator based on first injection instructions; and a wireless receiver connected to the local processor for receiving said first injection instructions from a separate, remote control device and delivering said first injection instructions to the local processor.

61. The device of claim 60 wherein said housing is free of user input components for providing injection instructions to the local processor.

62. The device of claim 60 further comprising a remote control device separate from the fluid delivery device and including:

a remote processor;

user interface components connected to the remote processor for transmitting the first injection instructions to the remote processor; and a transmitter connected to the remote processor for transmitting the first injection instructions to the receiver of the fluid delivery device.

63. The device of claim 60 wherein said local processor is further connected to the second latch activation device and programmed to apply a charge to said second electrically driven actuator based on second injection instructions; and a wireless receiver connected to the local processor for receiving said second injection instructions from a separate, remote control device and delivering said second injection instructions to the local processor.

64. The device of claim 63 said remote control device further including:

user interface components connected to the remote processor for transmitting the second injection instructions to the remote processor; and wherein said transmitter transmits said second injection instructions to the receiver of the fluid delivery device.

65. The device of claim 47 wherein said third position is said first position.

66. The device of claim 47 wherein said third position is within said housing and further away from said exit port than said first position.

67. The device of claim 47 wherein said third position is between said first and second positions, such that said penetrating member is located between said distal end of said flexible cannula and said exit port of said housing.

68. The device of claim 46 wherein said fluid transport device is constructed and arranged such that, upon activation of said first force, a medial portion of said needle, between said proximal and distal ends, travels in a direction substantially parallel to said first wall.

69. The device of claim 68 wherein said housing further includes a deflector located along a path of travel of said fluid transport device for imparting a bend of at least 15° to said distal end of said fluid transport device, thereby directing said distal end through said exit port as said fluid transport device is driven from said first position to said second position.

70. The device of claim 57 wherein said second latch activation device comprises an urging device disposed on said lateral protrusion wherein, upon said first spring imparting said first force on said lateral protrusion, said urging device contacts said second latch arm and urges said second latch arm into its open position, thereby imparting said second force to said lateral protrusion.

71. A device for delivering fluid to a person comprising:

a reservoir for containing a fluid to be delivered to the person;

a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device;

a housing containing said reservoir and said fluid transport device, said housing including an exit port for receiving said distal end of said fluid transport device upon injection of said distal end into said person and means for securing a first wall of said housing to the skin of the person; and an injection activation device contacting said fluid transport device for driving said penetrating member from a first position within said housing, through said exit port to a second position, external to said housing and into the skin of the person;

said fluid transport device comprising a needle housed within a flexible cannula, said penetrating member being disposed at a distal end of said needle, said flexible cannula including a retraction prevention mechanism proximate a distal end thereof, wherein, when said fluid transport device is in said first position, said retraction prevention mechanism of said soft cannula is within said housing and said penetrating member extends beyond said distal end of said flexible cannula;

said injection activation device comprising a plunger having a body portion coupled to said fluid transport device, such that the application of a first force in a first direction to said plunger drives said fluid transport device from said first position to said second position, wherein said penetrating member of said needle and said distal end of said flexible cannula extend through said exit port and into the skin of the person and said retraction prevention mechanism of said flexible cannula is in contact with said exit port of said housing.

72. The device of claim 71 wherein said retraction prevention mechanism comprises a protrusion disposed on said flexible cannula, said protrusion causing said flexible cannula to have a width dimension greater than a width dimension of said exit port.

73. The device of claim 72 wherein said retraction prevention mechanism comprises an annular ring disposed on said flexible cannula and having a greater diameter than a diameter of said exit port.

74. The device of claim 71 wherein said retraction prevention mechanism comprises an externally roughened portion of said flexible cannula.

75. The device of claim 71 wherein said retraction prevention mechanism comprises one or more barbs disposed on an exterior surface of said flexible cannula.

76. The device of claim 71 wherein, upon application of a second force to said plunger in a second direction substantially opposite said first direction, said penetrating member of said needle is retracted to a third position, and said retraction prevention mechanism of said flexible cannula remains in contact with said exit port, thereby forcing said distal end of said flexible cannula to remain in said second position.

77. The device of claim 76 wherein said plunger extends through a second wall of said housing and includes a head portion exterior to said housing, said first force being applied directly to said head portion by a person to drive said fluid transport device from said first position to said second position.

78. The device of claim 77 wherein said second force is applied directly to said head portion by a person to move said penetrating member of said needle to said third position.

79. The device of claim 77 wherein said injection activation device includes a spring coupled between said plunger and an interior wall of said housing, said spring being in a deenergized state when said fluid transport device is in said first position and in an energized state when said fluid transport device is in said second position, wherein, upon a termination of the application of said first force, said spring applies said second force to said plunger, thereby causing said penetrating member to move to said third position.

80. The device of claim 76 wherein said plunger includes a lateral protrusion and said injection activation device includes a first spring in an energized state and positioned relative to said lateral protrusion to impart said first force upon releasing its energy and a second spring in an energized state and positioned relative to said lateral protrusion to impart said second force upon releasing its energy and said injection activation device includes a latch assembly for maintaining said first spring in its energized state and said second spring in its energized state.

81. The device of claim 80 wherein said latch assembly includes a first latch arm movable between a closed position, in which said first spring is maintained in said energized state and an open position, in which said first spring is released from said energized state, thereby imparting said first force to said lateral protrusion to drive said fluid transport device from said first position to said second position.

82. The device of claim 81 wherein said first latch arm is held in said closed position by contact with said first spring and wherein said first latch arm is moved to said open state by a first latch activation device.

83. The device of claim 82 wherein said first latch activation device comprises a first electrically driven actuator coupled between said latch arm and said housing, such that, upon the application of a charge to said first electrically driven actuator, said first electrically driven actuator activates, causing said latch arm to move from said closed position to said open position.

84. The device of claim 83 wherein said first electrically driven actuator comprises one of a shape memory alloy, a shape memory polymer, a piezo electric actuator and a solenoid.

85. The device of claim 83 wherein said latch assembly includes a second latch arm movable between a closed position, in which said second spring is maintained in said energized state and an open position, in which said second spring is released from said energized state, thereby imparting said second force to said lateral protrusion to drive said fluid transport device from said second position to said third position.

86. The device of claim 85 wherein said second latch arm is held in said closed position by contact with said second spring and wherein said second latch arm is moved to said open state by a second latch activation device.

87. The device of claim 86 wherein said second latch activation device comprises a second electrically driven actuator coupled between said second latch arm and said housing, such that, upon the application of a charge to said second electrically driven actuator, said second electrically driven actuator activates, causing said second latch arm to move from said closed position to said open position.

88. The device of claim 87 wherein said first electrically driven actuator comprises one of a shape memory alloy, a shape memory polymer, a piezo electric actuator and a solenoid.

89. The device of claim 83 further comprising a local processor connected to the first latch activation device and programmed to apply a charge to said electrically driven actuator based on first injection instructions; and
a wireless receiver connected to the local processor for receiving said first injection instructions from a separate, remote control device and delivering said first injection instructions to the local processor.

90. The device of claim 89 wherein said housing is free of user input components for providing injection instructions to the local processor.

91. The device of claim 89 further comprising a remote control device separate from the fluid delivery device and including:
a remote processor;
user interface components connected to the remote processor for transmitting the first injection instructions to the remote processor; and
a transmitter connected to the remote processor for transmitting the first injection instructions to the receiver of the fluid delivery device.

92. The device of claim 81 wherein said local processor is further connected to the second latch activation device and programmed to apply a charge to said second electrically driven actuator based on second injection instructions; and
a wireless receiver connected to the local processor for receiving said second injection instructions from a separate, remote control device and delivering said second injection instructions to the local processor.

93. The device of claim 92 said remote control device further including:
user interface components connected to the remote processor for transmitting the second injection instructions to the remote processor; and
wherein said transmitter transmits said second injection instructions to the receiver of the fluid delivery device.

94. The device of claim 76 wherein said third position is said first position.

95. The device of claim 76 wherein said third position is within said housing and further away from said exit port than said first position.

96. The device of claim 76 wherein said third position is between said first and second positions, such that said penetrating member is located between said distal end of said flexible cannula and said exit port of said housing.

97. The device of claim 76 wherein said fluid transport device is constructed and arranged such that, upon activation of said first force, a medial portion of said needle, between said proximal and distal ends, travels in a direction substantially parallel to said first wall.

98. The device of claim 92 wherein said housing further includes a deflector located along a path of travel of said fluid transport device for imparting a bend of at least 15° to said distal end of said fluid transport device, thereby directing said distal end through said exit port as said fluid transport device is driven from said first position to said second position.

99. The device of claim 82 wherein said second latch activation device comprises an urging device disposed on said lateral protrusion wherein, upon said first spring imparting said first force on said lateral protrusion, said urging device contacts said second latch arm and urges said second latch arm into its open position, thereby imparting said second force to said lateral protrusion.

100. A device for delivering fluid to a person comprising:
a reservoir for containing a fluid to be delivered to the person;
a fluid transport device for dispensing fluid from said reservoir to the person, said fluid transport device including at least two cannulas, each of said at least two cannulas having a proximal end capable of being in fluid communication with said reservoir and a distal end having a penetrating member for piercing the skin of the person to facilitate the delivery of fluid to the person through the cannula;
a housing containing said reservoir and said fluid transport device, said housing including at least one exit port for receiving said distal end of each of said at least two cannulas upon injection of each distal end into the skin of the person; and
an injection activation device for separately injecting each of said at least two cannulas into the skin of the person, wherein, when a cannula is injected into the skin of the person, the injected cannula is in fluid communication with said reservoir and other, non-injected cannulas are not in fluid communication with said reservoir.

101. A device for delivering fluid to a person comprising:
a reservoir for containing a fluid to be deliver to the person;
a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device;
a housing containing said reservoir and said fluid transport device, said housing including an exit port for receiving said distal end of said fluid transport device upon injection of said distal end into said person, means for securing a first wall of said housing to the skin of the person and a retraction prevention mechanism proximate said exit port; and
an injection activation device contacting said fluid transport device for driving said penetrating member from a first position within said housing, through said exit port to a second position, external to said housing and into the skin of the person;
said fluid transport device comprising a needle housed within a flexible cannula, said penetrating member being disposed at a distal end of said needle;
said injection activation device comprising a plunger having a body portion coupled to said fluid transport device, such that the application of a first force in a first direction to said plunger drives said fluid transport device from said first position to said second position, wherein said penetrating member of said needle and said distal end of said flexible cannula extend through said exit port and into the skin of the person, said distal end of said flexible cannula being in frictional contact with said retraction prevention mechanism of said housing.

102. The device of claim 101 wherein, upon application of a second force to said plunger in a second direction substantially opposite said first direction, said penetrating member of said needle is retracted to a third position, and said retraction prevention mechanism of said housing maintains said distal end of said flexible cannula in said second position.

103. The device of claim 102 wherein said retraction prevention mechanism comprises an externally roughened portion of said exit port.

104. The device of claim 102 wherein said retraction prevention mechanism comprises one or more barbs disposed on a cannula-contacting surface of said exit port.

105. A device for delivering fluid to a person comprising:
a reservoir for containing a fluid to be delivered to the person;
a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device;
a housing containing said reservoir and said fluid transport device, said housing including an exit port for receiving said distal end of said fluid transport device upon injection of said distal end into said person and means for securing a first wall of said housing to the skin of the person; and
an injection activation device contacting said fluid transport device for driving said penetrating member from a first position within said housing, through said exit port to a second position, external to said housing and into the skin of the person;
said fluid transport device comprising a needle housed within a flexible cannula, said penetrating member being disposed at a distal end of said needle, beyond a distal end of said flexible cannula, said flexible cannula having a length that is less than a length of said needle, wherein a proximal end of said flexible cannula, opposite said distal end of said needle, is constructed and arranged to provide a frictional seal between said flexible cannula and said needle, said frictional seal preventing an escape of said fluid from between said distal end of said cannula and said needle, while allowing said distal end of said cannula to slide along said needle;

said injection activation device comprising a plunger coupled to said fluid transport device, such that the application of a first force in a first direction to said plunger drives said fluid transport device from said first position to said second position, wherein said penetrating member of said needle and said distal end of said flexible cannula extend through said exit port and into the skin of the person.

106. The device of claim 105 wherein said plunger comprises a first body portion coupled to said flexible cannula and a second body portion coupled to said needle and in contact with said first body portion;

wherein, upon the application of said first force, said second body portion drives said needle, said first body portion and said flexible cannula from said first position to said second position.

107. The device of claim 106 wherein, upon the application of a second force to said second body portion, in a direction substantially opposite said first direction, said second body portion and said needle are retracted to a third position.

108. The device of claim 107, said injection activation device further comprising a retention member for contacting said flexible cannula to retain said cannula in said second position prior to the application of said second force, thereby enabling said needle to be driven to said third position independent of said flexible cannula.

109. The device of claim 108 said injection activation device further comprising a first latch mechanism for maintaining said fluid transport device in said first position prior to the application of said first force.

110. A device for delivering fluid to a person comprising:

a reservoir for containing a fluid to be delivered to the person;

a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device;

a housing containing said reservoir and said fluid transport device, said housing including an exit port for receiving said distal end of said fluid transport device upon injection of said distal end into said person and means for securing a first wall of said housing to the skin of the person; and an injection activation device including a driving mechanism contacting said fluid transport device for driving said penetrating member from a first position within said housing, through said exit port to a second position, external to said housing and into the skin of said person;

said fluid transport device comprising a needle housed within a flexible cannula, said penetrating member being disposed at a distal end of said needle, said flexible cannula including a retraction prevention mechanism proximate a distal end thereof, wherein, when said fluid transport device is in said first position, said retraction prevention mechanism of said soft cannula is within said housing and said penetrating member extends beyond said distal end of said flexible cannula; and wherein said driving mechanism includes a rotational-to-linear motion converter coupled between rotational driving means of said injection activation device and said fluid transport device for converting rotational motion imparted on a drive shaft of said rotational-to-linear motion converter by said rotational drive means to linear motion which causes said driving mechanism to drive said penetrating member from said first position to said second position during a first portion of rotational travel of said drive shaft.

111. The device of claim 110 wherein said rotational-to-linear motion converter is operative for retracting said penetrating member to a third position during a second portion of rotational travel of said drive shaft.

112. The device of claim 110 wherein said rotational-to-linear motion converter further includes a crank coupled to said drive shaft, said crank including an urging rod; and said injection activation device including a force translating coupled to said fluid transport device, said force translator having a longitudinal slot for receiving said urging rod such that, upon rotation of said drive shaft and crank, said force translator converts rotational motion of said urging rod to a linear motion imparted on said fluid transport device to drive said penetrating member from said first position to said second and third positions.

113. The device of claim 110 wherein said driving means comprises a motor.

114. The device of claim 110 wherein said driving means comprises a spring in an energized state disposed about said drive axle which, when deenergized, causes said drive axle to rotate.

115. The device of claim 114 said injection activation device further comprising a latch arm movable between a closed position, maintaining said spring in said energized state, and an open position, in which said spring is released from said energized state, thereby causing said drive axle to rotate.

116. The device of claim 115 wherein said latch arm is held in said closed position by contact with said crank and wherein said latch arm is moved to said open state by a latch activation device.

117. The device of claim 116 wherein said latch activation device comprises an electrically driven actuator coupled to said latch arm such that, upon the application of a charge to said first electrically driven actuator, said first electrically driven actuator activates, causing said latch arm to move from said closed position to said open position.

118. The device of claim 117 wherein said electrically driven actuator comprises one of a shape memory alloy, a shape memory polymer, a piezo electric actuator and a solenoid.

119. The device of claim 116 further comprising a local processor connected to the latch activation device and programmed to apply a charge to said electrically driven actuator based on first injection instructions; and a wireless receiver connected to the local processor for receiving said first injection instructions from a separate, remote control device and delivering said first injection instructions to the local processor.

120. The device of claim 119 wherein said housing is free of user input components for providing injection instructions to the local processor.

121. The device of claim 119 further comprising a remote control device separate from the fluid delivery device and including:
- a remote processor;
- user interface components connected to the remote processor for transmitting the first injection instructions to the remote processor; and
- a transmitter connected to the remote processor for transmitting the first injection instructions to the receiver of the fluid delivery device.

122. The device of claim 111 wherein said third position is said first position.

123. The device of claim 111 wherein said third position within said housing and further away from said exit port than said first position.

124. The device of claim 111 wherein said third position is between said first and second positions, such that said penetrating member is located between said distal end of said flexible cannula and said exit port of said housing.

125. A device for delivering fluid to a person comprising:
- a reservoir for containing a fluid to be delivered to the person;
- a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device;
- a housing containing said reservoir and said fluid transport device, said housing including an exit port for receiving said distal end of said fluid transport device upon injection of said distal end into said person and means for securing a first wall of said housing to the skin of the person; and
- an injection activation device contacting said fluid transport device for driving said penetrating member from a first position within said housing, through said exit port to a second position, external to said housing and into the skin of the person;
- said fluid transport device comprising a needle housed within a flexible cannula, said penetrating member being disposed at a distal end of said needle, said flexible cannula including a retraction prevention mechanism proximate a distal end thereof, wherein, when said fluid transport device is in said first position, said retraction prevention mechanism of said soft cannula is within said housing and said penetrating member extends beyond said distal end of said flexible cannula;
- said injection activation device comprising a latch arm for maintaining said fluid transport device in said first position when said latch arm is in a closed state and a first spring in an energized state coupled to said fluid transport device, such that, upon releasing said latch arm, said first spring deenergizes causing said penetrating member to be driven from said first position to said second position, wherein said penetrating member of said needle and said distal end of said flexible cannula extend through said exit port and into the skin of the person and said retraction prevention mechanism of said flexible cannula is in contact with said exit port of said housing.

126. The device of claim 125, said first spring comprising a leaf spring having a distal end in contact with said fluid transport device which, upon said penetrating member being driven to said second position, falls out of contact with said fluid transport device.

127. The device of claim 125 said injection activation device further comprising a second spring coupled to said fluid transport device which is in a deenergized state when said penetrating member is in said first position and which becomes energized as said penetrating member is driven from said first position to said second position upon release of said latch arm, such that, when said penetrating member reaches said second position, said second spring is energized such that, when said first spring falls out of contact with said fluid transport device, said second spring retracts said penetrating member to a third position, while said retraction prevention mechanism of said flexible cannula remains in contact with said exit port, thereby forcing said distal end of said flexible cannula to remain in said second position.

128. The device of claim 125 wherein said latch arm is maintained in said closed position by contact with said fluid transport device and wherein said latch is released by a latch activation device.

129. The device of claim 128 wherein said latch activation device comprises an electrically driven actuator coupled to said latch arm such that, upon the application of a charge to said first electrically driven actuator, said first electrically driven actuator activates, causing said latch arm to move from said closed state to said open state.

130. The device of claim 129 wherein said electrically driven actuator comprises one of a shape memory alloy, a shape memory polymer, a piezo electric actuator and a solenoid.

131. The device of claim 128 further comprising a local processor connected to the latch activation device and programmed to apply a charge to said electrically driven actuator based on first injection instructions; and
- a wireless receiver connected to the local processor for receiving said first injection instructions from a separate, remote control device and delivering said first injection instructions to the local processor.

132. The device of claim 131 wherein said housing is free of user input components for providing injection instructions to the local processor.

133. The device of claim 131 further comprising a remote control device separate from the fluid delivery device and including:
- a remote processor;
- user interface components connected to the remote processor for transmitting the first injection instructions to the remote processor; and
- a transmitter connected to the remote processor for transmitting the first injection instructions to the receiver of the fluid delivery device.

134. The device of claim 1 wherein said driving mechanism comprises a sliding device disposed in a ramp portion of said injection activation device and in contact with said fluid transport device, said ramp portion being disposed relative to said fluid transport device such that, as said sliding device is moved along said ramp portion, an urging member of said sliding device slides between said ramp portion and said fluid transport device, causing said fluid transport device to be driven from said first position to said second position.

135. The device of claim 134 wherein said sliding device further comprises a handle portion external of said housing, for enabling a user of said device to manually slide said urging member along said ramp portion to drive said fluid transport device from said first position to said second position.

136. The device of claim 105 wherein said plunger comprises a body portion coupled to said needle and in contact with said proximal end of said flexible cannula, wherein upon the application of said first force in said first direction, said body portion drives said needle and said flexible cannula from said first position to said second position.

137. The device of claim 136 wherein, upon the application of a second force to said second body portion, in a direction substantially opposite said first direction, said body portion and said needle are retracted to a third position.

138. The device of claim 137, said injection activation device further comprising a retention member for contacting said flexible cannula to retain said cannula in said second position prior to the application of said second force, thereby enabling said needle to be driven to said third position independent of said flexible cannula.

139. The device of claim 138 wherein said injection activation further comprises a spring which is in an energized state while said fluid transport device is in said first position.

140. The device of claim 139 wherein, when said spring is deenergized, said spring applies said first force to said plunger during a first portion of deenergization, driving said fluid transport device from said first position to said second position.

141. The device of claim 140 wherein, during a second portion of said deenergization, said spring drives said plunger in said second direction, substantially opposite said first direction, thereby retracting said body portion and said needle to said third position.

142. The device of claim 139, said injection activation device further comprising a latch arm which, when in a closed state, maintains said fluid transport device in said first position and said spring in said energized state.

143. The device of claim 142 wherein said latch arm is maintained in said closed position by contact with said fluid transport device and wherein said latch is released by a latch activation device.

144. The device of claim 143 wherein said latch activation device comprises an electrically driven actuator coupled to said latch arm such that, upon the application of a charge to said first electrically driven actuator, said first electrically driven actuator activates, causing said latch arm to move from said closed state to said open state.

145. The device of claim 144 wherein said electrically driven actuator comprises one of a shape memory alloy, a shape memory polymer, a piezo electric actuator and a solenoid.

146. The device of claim 144 further comprising a local processor connected to the latch activation device and programmed to apply a charge to said electrically driven actuator based on first injection instructions; and
 a wireless receiver connected to the local processor for receiving said first injection instructions from a separate, remote control device and delivering said first injection instructions to the local processor.

147. The device of claim 146 wherein said housing is free of user input components for providing injection instructions to the local processor.

148. The device of claim 146 further comprising a remote control device separate from the fluid delivery device and including:
 a remote processor;
 user interface components connected to the remote processor for transmitting the first injection instructions to the remote processor; and
 a transmitter connected to the remote processor for transmitting the first injection instructions to the receiver of the fluid delivery device.

149. A device for delivering fluid to a person comprising:
 a reservoir for containing a fluid to be delivered to the person;
 a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device;
 a housing containing said reservoir and said fluid transport device, said housing including an exit port for receiving said distal end of said fluid transport device upon injection of said distal end into said person and means for securing a first wall of said housing to the skin of the person; and
 an injection activation device contacting said fluid transport device for driving said penetrating member from a first position within said housing, through said exit port to a second position, external to said housing and into the skin of the person;
 said fluid transport device comprising a needle housed within a flexible cannula, said penetrating member being disposed at a distal end of said needle, said flexible cannula including a retraction prevention mechanism proximate a distal end thereof, wherein, when said fluid transport device is in said first position, said retraction prevention mechanism of said soft cannula is within said housing and said penetrating member extends beyond said distal end of said flexible cannula;
 said injection activation device comprising:
  a cam and a follower portion slidably coupled to said fluid transport device, said cam including a first cam portion and a second cam portion, said fluid transport device being in said first position when said follower portion is in contact with said first cam portion and in said second position when said follower portion is in contact with said second cam portion, wherein said penetrating member of said needle and said distal end of said flexible cannula extend through said exit port and into the skin of the person and said retraction prevention mechanism of said flexible cannula is in contact with said exit port of said housing; and
  driving means for driving said follower portion from said first cam portion to said second cam portion.

150. The device of claim 149, said injection activation device further comprising a third cam portion, said driving means driving said follower portion from said second cam portion to said third cam portion, such that, as said follower portion is driven from said second cam portion to said third cam portion, said needle is retracted to a third position.

151. The device of claim 150 wherein said driving means comprises a spring biased for driving said follower portion from said first cam portion through said second cam portion to said third cam portion.

152. The device of claim 151 wherein, when said follower portion is in contact with said first cam portion, said spring is in an energized state.

153. The device of claim 152 said injection activation device further comprising a latch arm which, when in a closed state, maintains said spring in said energized state.

154. The device of claim 153 wherein said latch arm is maintained in said closed position by contact with said spring and wherein said latch is released by a latch activation device.

155. The device of claim 154 wherein said latch activation device comprises an electrically driven actuator coupled to said latch arm such that, upon the application of a charge to said first electrically driven actuator, said first electrically driven actuator activates, causing said latch arm to move from said closed state to said open state.

156. The device of claim 155 wherein said electrically driven actuator comprises one of a shape memory alloy, a shape memory polymer, a piezo electric actuator and a solenoid.

157. The device of claim 76 wherein said first force is imparted to said fluid transport device by a first spring and said second force is imparted to said fluid transport device by a second spring;
said first spring having a proximal end coupled to said needle and in contact with said flexible cannula and a distal end coupled to a distal end of said second spring;
said second spring having a proximal end which is in a fixed position with respect to said housing;
said first and second springs being in an energized state when said fluid transport device is in said first position.

158. The device of claim 157 wherein said injection activation device further comprises a unitary control mechanism which contacts said first and second springs to maintain them in said energized states, said control mechanism having a first finger contacting said proximal end of said first spring and a second finger contacting said distal end of said second spring, said first finger being shorter than said second finger.

159. The device of claim 158 wherein, upon moving said control mechanism away from said first and second springs, said first finger releases said proximal end of said first spring, causing said fluid transport device to be driven from said first position to said second position by said first force; and
after the application of said first force, said second finger releases said distal end of said second spring, causing said needle to be retracted from said second position to said third position by said second force.

160. A device for delivering fluid to a person comprising:
a reservoir for containing a fluid to be delivered to the person;
a fluid transport device for dispensing fluid from said reservoir to the person, said fluid transport device including a proximal end in fluid communication with said reservoir and a distal end having a means for facilitating the delivery of fluid to the person through the fluid transport device when inserted into the skin of the person;
a housing containing said reservoir and said fluid transport device, said housing including an exit port for receiving said distal end of said fluid transport device upon injection of said distal end into said person and means for securing a first wall of said housing to the skin of the person; and
a motion isolation device for isolating motion of said housing from said fluid transport device when said penetrating member is external to said housing and within the skin of the person.

161. The device of claim 160 wherein said motion isolation device comprises a spring mechanism coupled between said fluid transport device and said housing, said spring mechanism enabling said housing to move independently of said fluid transport device.

162. The device of claim 160 wherein said fluid transport device comprises a fluid cannula and said motion isolation device comprises a loop in said flexible cannula between said distal end of said flexible cannula and a medial portion of said flexible cannula which is fixed to said housing, said loop portion enabling said housing to move independently of said flexible cannula.

163. The device of claim 1 wherein said plunger is formed from a transparent material for providing a view of an injection site of said penetrating member.

164. The device of claim 163 wherein said plunger provides a magnified view of said injection site.

165. The device of claim 163 further comprising illumination means for directing light to said injection site through said plunger.

166. A device for delivering fluid to a person comprising:
a reservoir for containing a fluid to be delivered to the person;
a fluid transport device for dispensing fluid from said reservoir to the person, said fluid transport device including a proximal end in fluid communication with said reservoir and a distal end having a penetrating member for piercing the skin of the person to facilitate the delivery of fluid to the person through the fluid transport device;
a housing containing said reservoir and said fluid transport device, said housing including an exit port for receiving said distal end of said fluid transport device upon injection of said distal end into the skin of the person; and
an injection activation device contacting said fluid transport device for driving said penetrating member from a first position within said housing, through said exit port to a second position, external to said housing and into the skin of the person;
said fluid transport device comprising a needle housed within a flexible cannula, said penetrating member being disposed at a distal end of said needle, wherein, when said fluid transport device is in said first position, said penetrating member extends beyond said distal end of said flexible cannula;
said injection activation device comprising:
a plunger device coupled to said fluid transport device;
a latch mechanism comprising a first latch arm for maintaining a first spring in an energized state and a second latch arm for maintaining a second spring in an energized state;
wherein, upon releasing said first latch arm, said first spring deenergizes and forces said plunger device and said fluid transport device from said first position to said second position and, upon said plunger and fluid transport device reaching said second position, said second latch arm is released, causing said second spring to deenergize and to force said plunger device from said second position to a third position.

167. The device of claim 166 wherein said latch mechanism comprises an electrically driven actuator coupled to said first latch arm such that, upon the application of a charge to said electrically driven actuator, said electrically driven actuator activates, causing said first latch arm to be released.

168. The device of claim 167 wherein said plunger device includes means for releasing said second latch arm, said releasing means contacting said second latch arm as said plunger device reaches said second position, thereby causing said second latch arm to be released.

169. The device of claim 168 wherein said electrically driven actuator comprises one of a shape memory alloy, a shape memory polymer, a piezo electric actuator and a solenoid.

170. The device of claim 166 wherein said third position is said first position.

171. The device of claim 166 wherein said third position is within said housing and further away from said exit port than said first position.

172. The device of claim 166 wherein said third position is between said first and second positions, such that said penetrating member is located between said distal end of said flexible cannula and said exit port of said housing.

* * * * *